United States Patent
Medina et al.

(10) Patent No.: US 8,084,209 B2
(45) Date of Patent: Dec. 27, 2011

(54) HMGCR ISOFORMS IN PREDICTION OF EFFICACY AND IDENTIFICATION OF CHOLESTEROL-MODULATING COMPOUNDS

(75) Inventors: Marisa Lin Wong Medina, Hercules, CA (US); Ronald M. Krauss, Berkeley, CA (US)

(73) Assignee: Children's Hospital & Research Center Oakland, Oakland, CA (US)

( * ) Notice: Subject to any disclaimer, the term of this patent is extended or adjusted under 35 U.S.C. 154(b) by 752 days.

(21) Appl. No.: 11/994,495

(22) PCT Filed: Jul. 21, 2006

(86) PCT No.: PCT/US2006/028619
§ 371 (c)(1),
(2), (4) Date: May 29, 2008

(87) PCT Pub. No.: WO2007/014132
PCT Pub. Date: Feb. 1, 2007

(65) Prior Publication Data
US 2008/0293054 A1    Nov. 27, 2008

Related U.S. Application Data

(60) Provisional application No. 60/701,888, filed on Jul. 22, 2005.

(51) Int. Cl.
*C12Q 1/68* (2006.01)
*G01N 33/53* (2006.01)

(52) U.S. Cl. ............... 435/6.11; 435/6.13; 435/6.18; 435/7.1

(58) Field of Classification Search .................. None
See application file for complete search history.

(56) References Cited

U.S. PATENT DOCUMENTS

2003/0215819 A1   11/2003   Frudakis
2005/0069881 A1    3/2005   Poirier et al.

FOREIGN PATENT DOCUMENTS

WO   WO0079003 A1   12/2000
WO   WO03102209 A2  12/2003

OTHER PUBLICATIONS

Aboushadi, N., et al. Characterization of peroxisomal 3-hydroxy-3-methylglutaryl coenzyme A reductase in UT2 cells: sterol biosynthesis, phosphorylation, degradation, and statin inhibition. Biochemistry. 2000, vol. 39, No. 1, pp. 237-247.
Breitling, R., et al. A second gene for peroxisomal HMG-CoA reductase? A genomic reassessment. Journal of Lipid Research. 2002, vol. 43, pp. 2031-2036.
Chasman, D., et al. Pharmacogenetic study of statin therapy and cholesterol reduction. JAMA. 2004, vol. 291, No. 23, pp. 2821-2827.
Clarke, C., et al. Regulation of 3-hydroxy-3-methylglutaryl coenzyme A reducatse m-RNA levels in rat liver. Proc Nat Acad Sci USA. 1983, vol. 80, pp. 3305-3308.
Johnson, J., et al. Genome-wide survey of human alternative pre-mRNA splicing with exon junction microarrays. Science. 2003, vol. 302, No. 5653, pp. 2141-2144.
Keller, G., et al. 3-Hydroxy-3-methylglutaryl coenzyme A reductase localization in rat liver peroxisomes and microsomes of control and cholestyramine-treated animals: quantitative biochemical and immunoelectron microscopical analyses. J Cell Biol. 1986, vol. 103, No. 3, pp. 875-886.

*Primary Examiner* — James Martinell
(74) *Attorney, Agent, or Firm* — Carol L. Francis; Bozicevic, Field & Francis LLP

(57) ABSTRACT

The present invention provides methods for assessing a subject's responsiveness to a HMGCR inhibitor therapy, and selection of a HMGCR inhibitor therapy based upon such methods. The invention further provides methods for identifying agents that modulate HMGCR activity, e.g., through modulating HMGCR mRNA splicing, while avoiding elevation of the statin-resistant isoform of HMGCR.

23 Claims, 16 Drawing Sheets

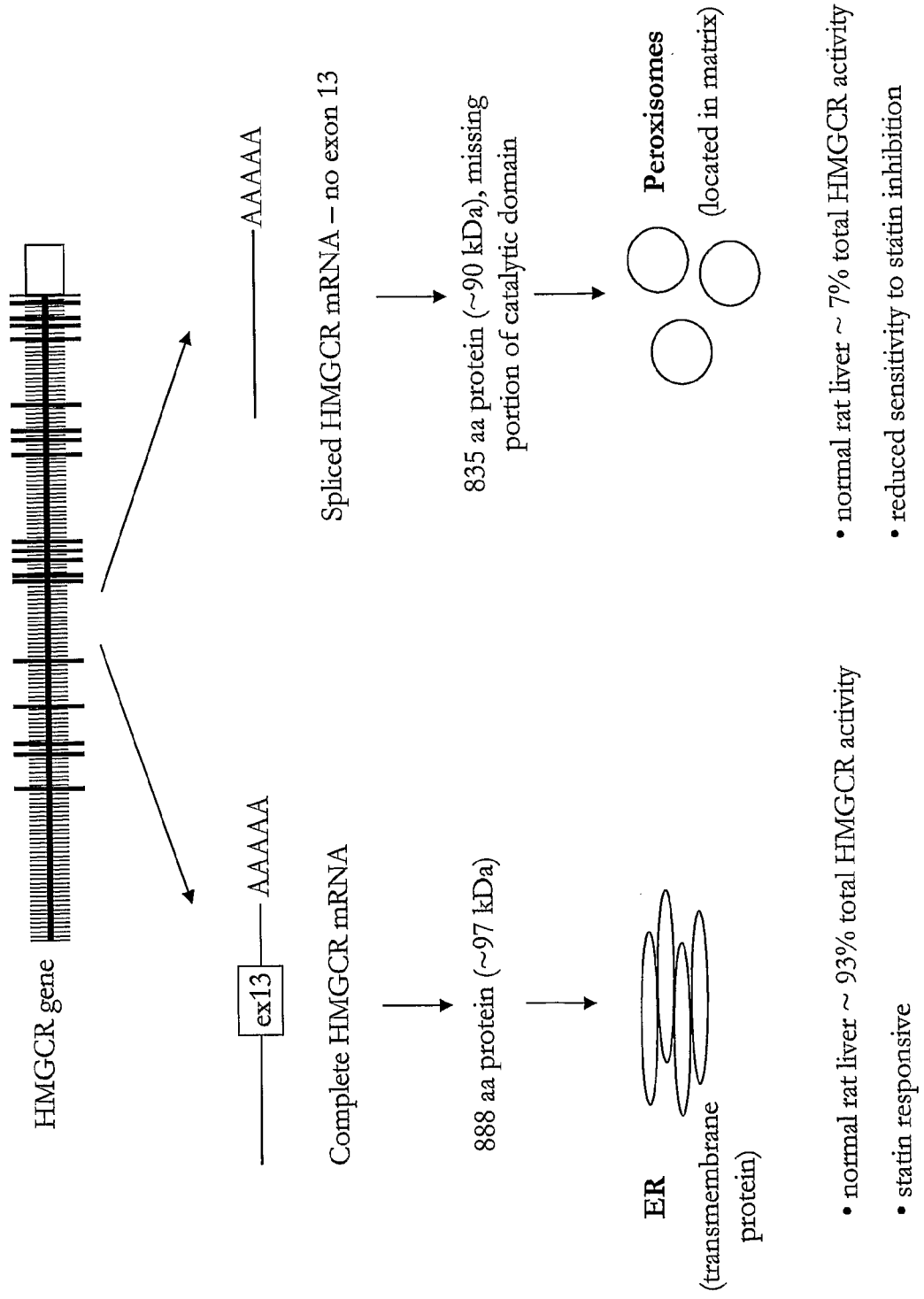

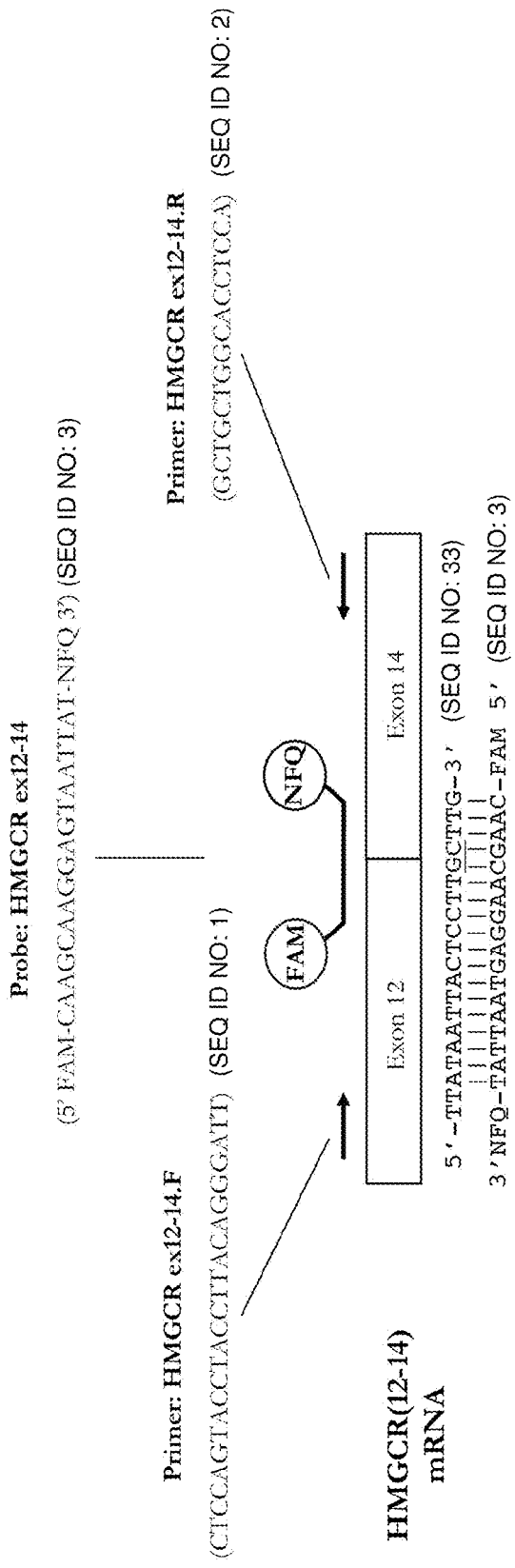

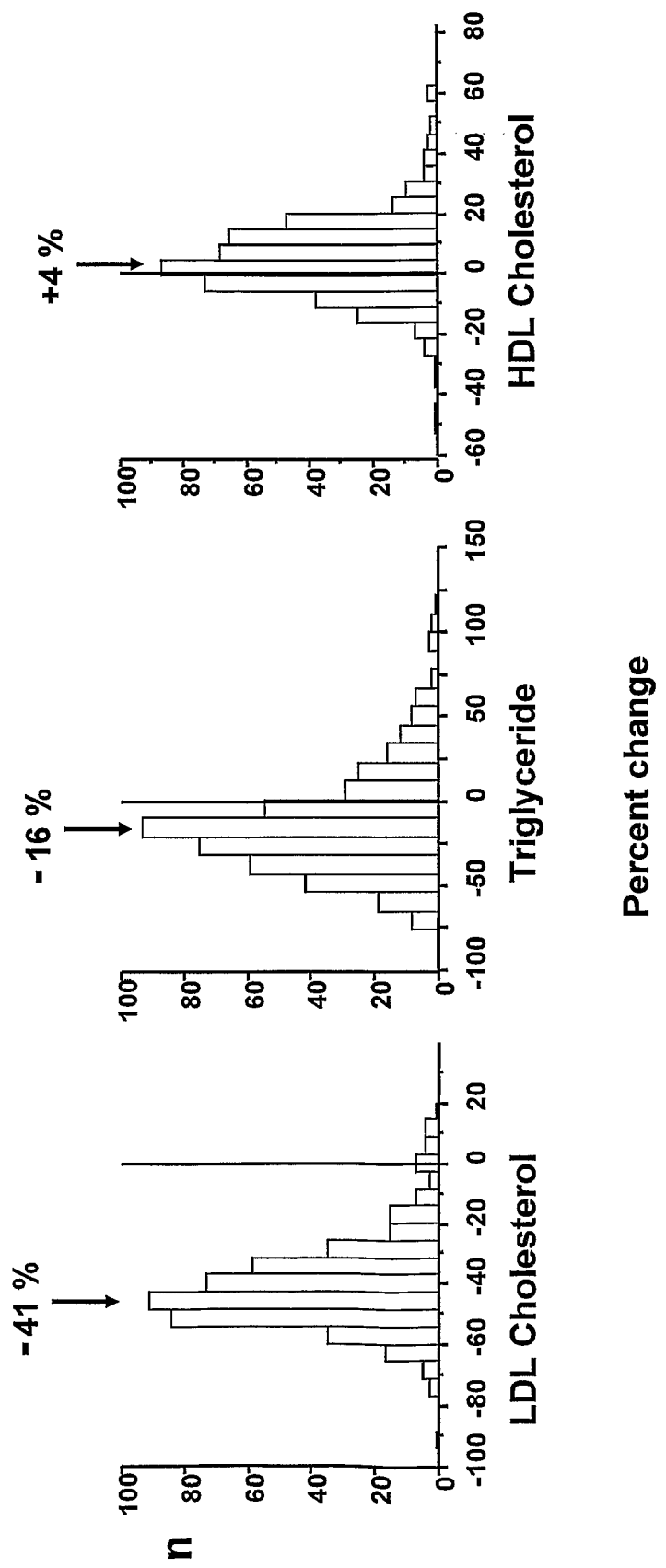

FIG. 4B
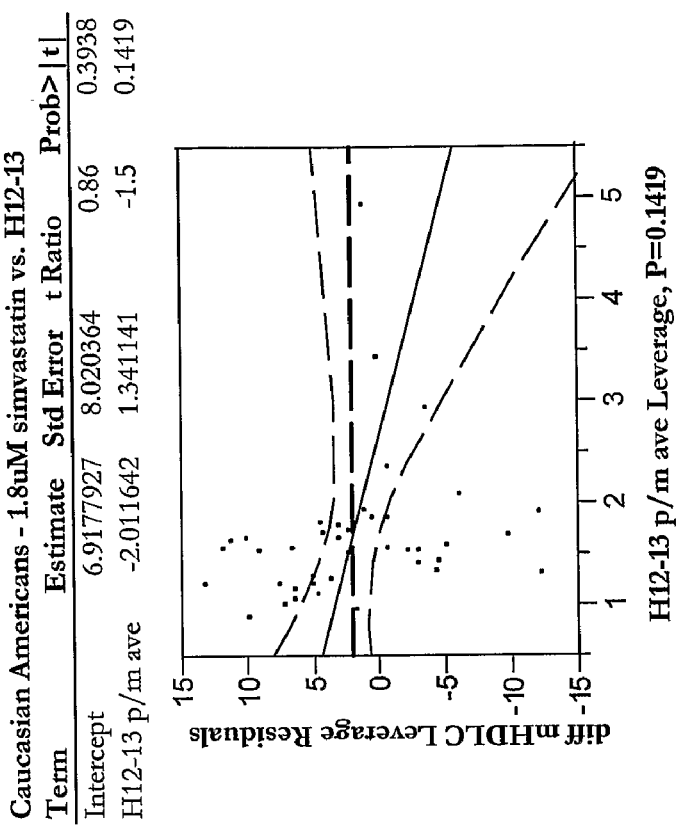
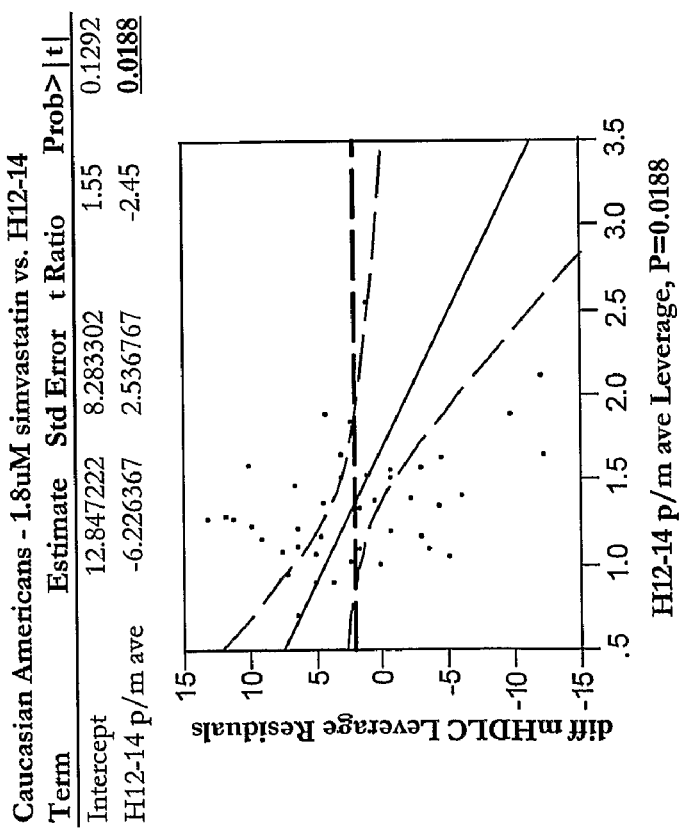

FIG. 10A
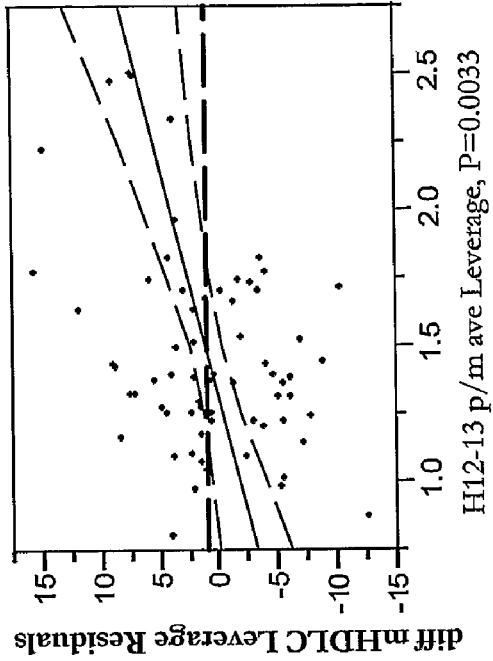
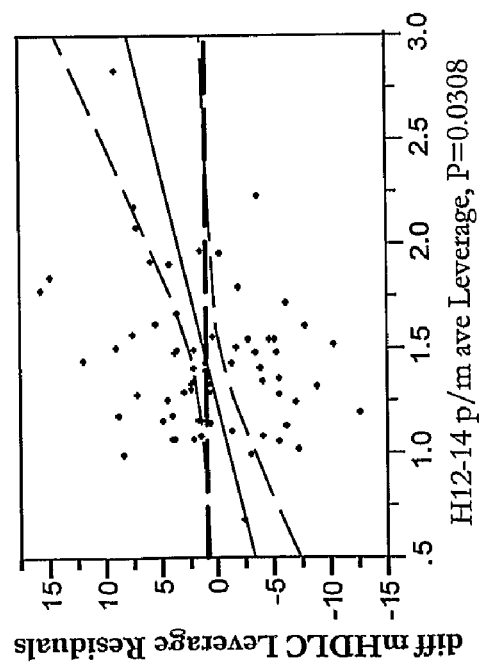

FIG. 10B
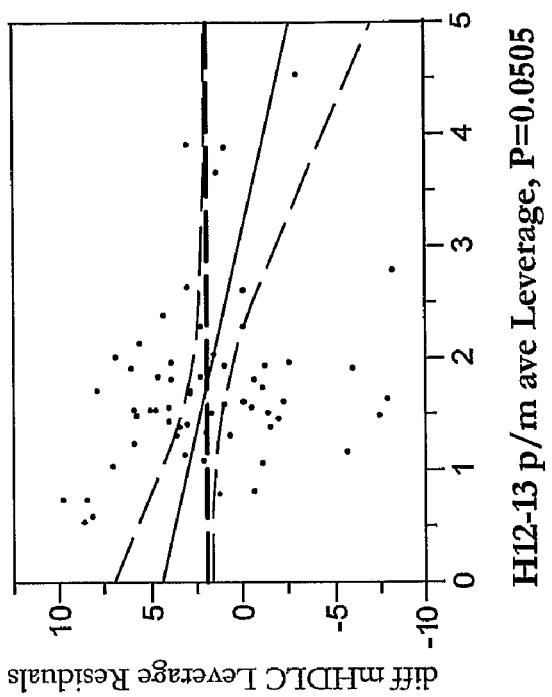
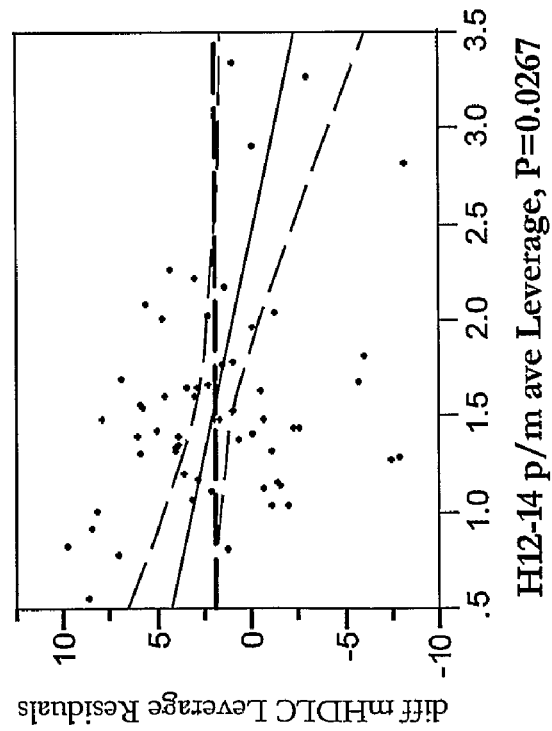

US 8,084,209 B2

HMGCR ISOFORMS IN PREDICTION OF EFFICACY AND IDENTIFICATION OF CHOLESTEROL-MODULATING COMPOUNDS

CROSS-REFERENCE TO RELATED APPLICATION

This application claims priority benefit of U.S. provisional application Ser. No. 60/701,888, filed Jul. 22, 2005, which application is incorporated by reference herein in its entirety.

STATEMENT REGARDING FEDERALLY SPONSORED RESEARCH

This invention was made with government support under grants no. U01 HL69757 awarded by the National Institutes of Health. The government has certain rights in the invention.

FIELD OF THE INVENTION

This invention relates to methods of assessing sensitivity to cholesterol-modulating drugs and methods of identifying same.

BACKGROUND OF THE INVENTION

Elevated cholesterol levels are an important risk factor for cardiovascular disease, which is a leading cause of death in the industrialized world. Controlling the risk factors for cardiovascular disease is a key preventive and therapeutic target in reducing this high mortality rate. Well-established risk factors for cardiovascular disease include elevated plasma levels of cholesterol (hypercholesterolemia), triglycerides, homocysteine, and certain lipoproteins, such as low-density lipoprotein (LDL) cholesterol.

In particular, an elevated level of LDL cholesterol is an independent risk factor for premature coronary heart disease (CHD), with a value of 160 mg/dl or greater designated as high-risk by the National Cholesterol Education Program Adult Treatment Panels I, II and III. Current goals of therapy for all patients with elevated LDL cholesterol include reducing levels to: (i) less than 160 mg/dl in those with at least one or more CHD risk factors; (ii) less than 130 mg/dl in those with 2 or more CHD risk factors; and (iii) less than 100 mg/dl in patients with established CHD or CHD risk equivalents, one of which is diabetes.

Elevated intermediate-density lipoprotein (IDL) levels are another independent risk factor for cardiovascular disease. (see, e.g., Chapman et al. Clin Cardiol. (2003) 26(1 Suppl 1):I7-10; Shoji et al. J Am Soc Nephrol (1998) 9:1277-84; Nordestgaard et al. Eur J Epidemiol. 1992 May; 8 Suppl 1:92-8. Levels of apoB (the main protein component of LDL) and apoAI (the main protein component of HDL) represent additional risk factors for cardiovascular disease. See, e.g., Walldius et al. J Intern Med. (2006) 259(5):493-519; Charlton-Menys et al. J Intern Med. (2006) 259(5):462-72; Walldius et al. Clin Chem Lab Med. (2004) 42(12):1355-63. Stated simply, LDL and IDL are known to have atherogenic properties in patients. In contrast, HDL and ApoA1 are known to have anti-atherogenic properties.

The discovery of drugs that inhibit 3-hydroxy-3-methylglutaryl coenzyme A reductase (HMGCR) was a major advance in the treatment of patients with elevated plasma concentrations of LDL cholesterol. The efficacy of HMGCR inhibitors (statins) in LDL-lowering and CHD risk reduction has clearly been demonstrated in a number of primary and secondary intervention trials. (For a review, see, e.g., Brousseau, IDrugs. (2003) 6(5):458-63).

HMGCR catalyzes the conversion of 3-hydroxy-3-methylglutaryl-CoA (HMG-CoA) to mevalonate in the rate limiting step of biosynthesis of isoprenoids, a class of compounds involved in sterol synthesis (e.g., cholesterol synthesis) as well as other cellular functions. Because of its role in cholesterol synthesis, HMGCR inhibitors have been of particular interest in controlling cholesterol levels. Statins, one of the most widely prescribed classes of drugs in the US, directly inhibit HMGCR activity, and the resulting reductions of blood levels of LDL cholesterol have been shown to substantially reduce risk for coronary heart disease.

At least four isoforms of HMGCR have been described (see, e.g., WO 03/102209, and Keller et al., 1986 *J Cell Biol* 103(3): 875-86). The classical isoform of the HMGCR enzyme is a transmembrane-protein anchored to the endoplasmic reticulum, sometimes referred to as the "ER HMGCR" or "full-length HMGCR", and is encoded by the complete transcript of the HMGCR gene in humans (see, e.g., GenBank Accession No. NM_000859). The HMGCR isoform found in peroxisomes has been reported to be resistant to statin inhibition (Aboushadi et al., 2000 *Biochemistry* 39(1): 237-47). The peroxisomal HMGCR, which the inventors suggest here is a splice variant of the ER HMGCR isoform in humans, lacks exon 13 (Johnson et al., 2003 *Science* 302 (5653): 2141-4; GenBank Accession no. BC033692). Peroxisomal HMGCR is involved in biosynthesis of cholesterol, plasmalogen and bile acids and oxidation of fatty acids. Patients having peroxisome deficiencies (PD) have a reduced rate of cholesterol synthesis (approximately 16-20% of normal) and abnormally low plasma cholesterol concentrations. PD patients also exhibit reduced uptake of LDL-cholesterol due to abnormal LDL synthesis. Furthermore, there is reduced LDLR recognition of LDL produced by PD patients.

The wide range of inter-individual efficacy of HMGCR inhibitor drugs (statins) is a major issue in treatment of patients in need of cholesterol-lowering therapy. Studies have reported that the decrease in LDL-cholesterol in similar individuals taking the same type and dose of statin, adjusted for compliance, range from less than 5% to greater than 60%. (1998. Influence of pravastatin and plasma lipids on clinical events in the West of Scotland Coronary Preventive Study (WOSCOPS). Circulation 97:1440-1445; Sacks et al. Circulation 97:1446-1452) Reduced statin responsiveness likely contributes to the observation from clinical trials that 70-80% of clinical events are not prevented by statin treatment. (1998. Influence of pravastatin and plasma lipids on clinical events in the West of Scotland Coronary Preventive Study (WOSCOPS). Circulation 97:1440-1445 MRC/BHF Heart Protection Study of cholesterol lowering with simvastatin in 20 536 high-risk individuals: a randomised placebo controlled. Trial. Heart Protection Study Collaborative Group. Lancet 2002; 360: 7-22).

Several investigators have attempted to explain the variability in statin response by evaluation of genetic markers such as single nucleotide polymorphisms (SNPs) in the HMGCR gene (Chasman et al., (2004) *JAMA* 291(23): 2821-2827; US 2003/0215819; WO 00/79003). However, SNPs that are known to be associated with statin pharmacogenetics are relatively rare, and therefore only useful for predicting efficacy in a small percentage of the population.

Thus, there is a need for a test to evaluate an individual's sensitivity to HMGCR inhibitors, such as statins. A test to identify those patients most likely to benefit from such a treatment would represent a substantial improvement in the ability to reduce cardiovascular risk in the population, while avoiding unnecessary and even counterproductive administration of drugs that do not provide the desired therapeutic result. There is also a need for methods for identifying drugs that can modulate cholesterol levels (e.g., decrease LDL cholesterol levels, decrease IDL cholesterol levels, and/or raise HDL-cholesterol levels), either when administered alone or in conjunction with a statin, with improved efficacy, particularly in patients who fail to reach the desired therapeutic targets with statin treatment. The present invention addresses each of these needs.

LITERATURE

Aboushadi, et al. (2000). "Characterization of peroxisomal 3-hydroxy-3-methylglutaryl coenzyme A reductase in UT2 cells: sterol biosynthesis, phosphorylation, degradation, and statin inhibition." *Biochemistry* 39(1): 237-47; Chasman et al. (2004). "Pharmacogenetic study of statin therapy and cholesterol reduction." *JAMA* 291(23): 2821-2827; Johnson et al. "Genome-wide survey of human alternative pre-mRNA splicing with exon junction microarrays." *Science* 302(5653): 2141-4; Keller et al. (1986). "3-Hydroxy-3-methylglutaryl coenzyme A reductase localization in rat liver peroxisomes and microsomes of control and cholestyramine-treated animals: quantitative biochemical and immunoelectron microscopical analyses." *J Cell Biol* 103(3): 875-86; Clarke et al. (1983) "Regulation of 3-hydroxy-3-methylglutaryl coenzyme A reductase m-RNA levels in rat liver" *Proc. Nat. Acad. Sic. USA* 80:3305-3308.

U.S. Published Application 2003/0215819 "Compositions and methods for inferring a response to statin";

PCT Publication No. WO 03/102209.

SUMMARY OF THE INVENTION

The present invention generally provides methods for assessing a subject's responsiveness to a HMGCR inhibitor therapy, and selection of a HMGCR inhibitor therapy based upon such methods. The invention further provides methods for identifying agents that modulate HMGCR activity, e.g., through modulating HMGCR mRNA splicing, while avoiding elevation of the statin resistant isoform of HMGCR.

Accordingly, in one aspect the invention features a method for determining responsiveness of a subject to HMGCR inhibitor therapy by contacting a cell of a subject with an HMGCR inhibitor and assessing expression of a HMGCR (12-14) isoform in the cell of the subject, where wherein the expression level of the HMGCR(12-14) in the presence of the HMGCR inhibitor compared to a baseline expression level of the HMGCR(12-14) isoform in the absence of the HMGCR inhibitor is indicative of the subject's responsiveness to the HMGCR inhibitor.

In related embodiments, expression of the HMGCR(12-14) isoform in the cell in the presence of the HMGCR inhibitor which is increased relative to a baseline expression level in the absence of the HMGCR inhibitor indicates the subject will have an overall reduced therapeutic response to the HMGCR inhibitor. In related embodiments, and when HMGCR(112-14) expression levels are to be used to determine response of the subject to the HMGCR inhibitor as assessed by a change in one of total cholesterol, LDL, IDL, ApoA1 or ApoB, the expression level of the HMGCR(12-14) in the presence of the HMGCR inhibitor is measured as $$\frac{\Delta HMGCR(12\text{-}14)}{\Delta tHMGCR}$$

where ΔHMGCR(12-14 is a change of the expression level of HMGCR(12-14) in the presence of the HMGCR inhibitor relative to the baseline expression level in the absence of the HMGCR inhibitor, and ΔtHMGCR is to a change of expression level of total HMGCR in the presence of the HMGCR inhibitor relative to a baseline total HMGCR expression level in the absence of the HMGCR inhibitor.

In further related embodiments, an increase in HMGCR (12-14) isoform expression in the presence of the HMGCR inhibitor compared to the baseline expression level is assessed, where the increase in HMGCR(12-14) expression is inversely correlated with an expected reduction in total cholesterol, low density lipoprotein (LDL) cholesterol, intermediate density lipoprotein (IDL) cholesterol, and/or apoB in the subject following administration of the HMGCR inhibitor.

In another embodiment, a fold change in HMGCR(12-14) isoform expression in the presence of the HMGCR inhibitor over the baseline expression level is correlated with a change in high density lipoprotein (HDL) cholesterol in the subject following administration of the HMGCR inhibitor at a selected dose, wherein when the subject is Caucasian, the fold change in HMGCR(12-14) is inversely correlated with an expected increased in HDL cholesterol in the subject and when the subject is an African American the fold change in HMGCR(12-14) is directly correlated with an expected increase in HDL cholesterol in the subject.

In other related embodiments, HMGCR(112-14) expression is assessed by detection of mRNA encoding the HMGCR (12-14) isoform. The subject's cell can be contacted with the HMGCR inhibitor either in vitro (in culture) or in vivo.

In another aspect, the invention features methods for treating a subject having or suspected of having a lipid disorder by contacting a cell from the subject with an HMGCR inhibitor, assessing expression of a HMGCR(12-14) isoform in the cell of the subject, wherein the expression level of HMGCR(12-14) in the presence of the HMGCR inhibitor compared to a baseline expression level of HMGCR(12-14) in the absence of the HMGCR inhibitor is indicative of the subject's responsiveness to the HMGCR inhibitor, and selecting a therapy for the lipid disorder for the subject so as to provide for at least one of a reduction in total cholesterol, reduction in LDL cholesterol, reduction in apoB, reduction in IDL cholesterol, an increase in HDL cholesterol, or an increase in apoAI.

In related embodiments, a level of expression of the HMGCR(12-14) isoform in the cell in the presence of the HMGCR inhibitor which is increased relative to a baseline expression level in the absence of the HMGCR inhibitor indicates the subject will have overall decreased therapeutic responsiveness to the HMGCR inhibitor. In further related embodiments a fold increase in HMGCR(12-14) isoform expression is assessed, where the fold increase in HMGCR (12-14) expression in the presence of the HMGCR inhibitor over the baseline expression level is inversely correlated with an expected reduction in total cholesterol, an expected reduction in low density lipoprotein (LDL) cholesterol, and an expected reduction in apoB, and is directly correlated with a change in apoAI following administration of the HMGCR inhibitor to the subject.

In further embodiments, a fold increase in HMGCR(12-14) isoform expression in the presence of the HMGCR inhibitor over the baseline expression level is correlated with a change in high density lipoprotein (HDL) cholesterol in the subject following administration of the HMGCR inhibitor at a selected dose, wherein when the subject is Caucasian, the fold increase in HMGCR(12-14) is inversely correlated with an expected increased in HDL cholesterol in the subject and when the subject is an African American the fold change in HMGCR(12-14) is directly correlated with an expected increased in HDL cholesterol in the subject.

In further embodiments, HMGCR(12-14) isoform expression is assessed by detection of mRNA encoding an HMGCR (12-14) isoform. The subject's cell can be contacted with the HMGCR inhibitor either in vitro (in culture) or in vivo.

In yet another aspect the invention features a method of classifying a subject according to sensitivity or resistance to a HMGCR inhibitor therapy by determining an expression level of a HMGCR(12-14) isoform in the cell of the subject, wherein the expression level of the HMGCR(12-14) isoform in the presence of the HMGCR inhibitor compared to an expression level of the HMGCR(12-14) isoform in the absence of the HMGCR inhibitor is indicative of the subject's responsiveness to the HMGCR inhibitor. The subject is then assigned to a classification according to HMGCR inhibitor responsiveness.

In another aspect the invention features a method for determining a subject's suitability for participation in a clinical trial for a cholesterol modulating therapy by determining an expression level of a 3-hydroxy-3-methylglutaryl coenzyme A reductase (HMGCR) isoform in the cell of the subject, wherein the HMGCR isoform is a HMGCR(12-14) isoform, wherein the expression level of the HMGCR(12-14) in the presence of the HMGCR inhibitor compared to an expression level of the HMGCR(12-14) isoform in the absence of the HMGCR inhibitor is indicative of the subject's responsiveness to the HMGCR inhibitor. The expression level of the HMGCR(12-14) isoform is indicative of the subject's suitability for participation in the clinical trial.

In a further aspect, the invention features a method for screening a candidate agent by contacting a mammalian cell with a candidate agent, and determining an expression level of a HMGCR(12-14) isoform in the cell, where a candidate agent that facilitates inhibition of HMGCR activity without a substantial increase in HMGCR(12-14) isoform expression is identified. In related embodiments, the cell is contacted with the candidate agent in the presence of a HMGCR inhibitor. In further related embodiments, a candidate agent that provides for decreased HMGCR(12-14) isoform expression in the presence of a HMGCR inhibitor is a candidate for combination therapy with the HMGCR inhibitor. In further related embodiments, a candidate agent is identified that, in the absence of an HMGCR inhibitor, provides for increased HMGCR(12-14) expression.

In another aspect the invention features methods for screening a candidate agent by contacting a mammalian cell with a candidate agent, and determining an expression level of a HMGCR(12-14) isoform in the cell, where wherein a candidate agent that facilitates an increase in HMGCR(12-14) isoform in the presence of a HMGCR inhibitor is identified as an agent that can facilitate an increase in apoAI. In related embodiments, the cell is contacted with the candidate agent in the presence of a HMGCR inhibitor.

In another aspect, the invention features methods for screening a candidate agent by contacting a mammalian cell with a candidate agent; and determining an expression level of a HMGCR(12-14) isoform, a HMGCR(12-13) isoform or total HMGCR, wherein a candidate agent that facilitates a change in an expression level of at least one of HMGCR(12-14) isoform, HMGCR(12-13) isoform or total HMGCR is identified as an agent that can facilitate change in HDL cholesterol. In related embodiments, the assay is conducted in the presence of a HMGCR inhibitor.

In another aspect, the invention features methods for determining responsiveness of HDL cholesterol levels in a subject to a HMGCR inhibitor therapy by contacting a cell of a subject with a selected dose of an HMGCR inhibitor, and assessing expression of a HMGCR expression marker in the cell of the subject, where the marker is HMGCR(12-13) isoform, HMGCR(12-14) isoform or total HMGCR, wherein a fold change in expression of the HMGCR(12-13) or the HMGCR(12-14) isoform in the presence of the HMGCR inhibitor compared to a baseline expression level in the absence of the HMGCR inhibitor is indicative of the subject's responsiveness to the HMGCR inhibitor as assessed by HDL cholesterol levels and wherein, when the subject is a Caucasian American, a fold change in expression of total HMGCR compared to a baseline expression level in the absence of the HMGCR inhibitor is indicative of the subject's responsiveness to the HMGCR inhibitor as assessed by HDL cholesterol levels.

In another aspect, the invention features methods for modulating HDL cholesterol levels in a subject by contacting a cell from a subject with a HMGCR inhibitor, assessing expression of a HMGCR expression marker in the cell of the subject, where the marker is HMGCR(12-13) isoform, HMGCR(12-14) isoform or total HMGCR, and administering a therapy to modulate HDL cholesterol levels in the subject, wherein the therapy is selected based on the results of said assessing, wherein said administering provides of modulation of HDL cholesterol levels in the subject.

The invention thus provides methods for assessing whether a subject is likely to exhibit a clinically meaningful response to a cholesterol-lowering therapy, particularly an LDL-lowering therapy.

The methods of the invention can facilitate selection of a cholesterol-lowering therapy that is more likely to provide the desired effects. For example, the present invention can direct a clinician to change the selection of cholesterol-lowering drug, rather than to increase the dose of an HMGCR inhibitor. As a result, clinicians can better treat their patients so as to provide for a more effective reduction in the risks associated with elevated cholesterol, particularly elevated LDL cholesterol. The methods of the invention serve to avoid the expense, frustration, and risks associated with administration of cholesterol-lowering therapies that would not achieve the desired effect.

The invention can also provide a more cost effective means of determining response to HMGCR inhibitor therapy than the current practice of treating a patient for number of weeks and then measuring lipid response. The method can provide further cost-savings determining if increased dosage of a statin is likely to have the desired effect, thus avoiding unnecessary costs where such increased dosage would likely not be effective.

With respect to methods of screening using patient cells in vitro, the invention provides methods for assessing whether a subject is likely to exhibit a clinically meaningful response to a cholesterol-lowering therapy, particularly an LDL-lowering therapy, without the need to administer drug to the subject.

By identifying patients whose poor response to HMGCR inhibitor is correlated with an HMGCR expression profile, the clinician can avoid attempts to administer increasing doses of the drug. By avoiding administration of higher HMGCR inhibitor doses, the incidence of statin-induced myopathy or other adverse effects such as those on the liver or nervous system can be reduced. For example, currently if a patient did not have the optimal or desired effects on cholesterol with statin treatment (such as lowering LDL-cholesterol), then a clinician might increase the dose of statin drug. This may result in increased risk of statin-induced myopathy and/or other undesired side effects. This invention would allow a clinician to determine if the suboptimal response is likely to be remedied by increasing dosage without subjecting the patient to increased risk of dangerous side effects.

Unlike other genetic markers such as SNPs, the tests of the invention to predict responsiveness to a HMGCR inhibitor by using HMGCR isoform expression as a marker is applicable to patients regardless of genetic status and is not limited to a subset of carriers with rare genetic mutations, with the proviso that where responsiveness in terms of HDL cholesterol levels is to be assessed, care should be taken to assess HMGCR isoform expression in Caucasians and African Americans according to the race-based phenomenon described herein, and to be mindful of the dose-effect upon HMGCR isoform expression profile. If a serum cholesterol parameter other than HDL cholesterol is to be assessed, then responsiveness to therapy can be assessed independent of race.

The discovery that statins or other drugs that elevate expression of an HMGCR(12-14) isoform mRNA or protein that make statins less effective in the inhibition of HMGCR activity upon which the methods described herein is based can be exploited in a drug screening assay to identify drugs that provide a more favorable expression ratio of the normal to statin-resistant HMGCR isoforms.

The drug screening methods described herein can be used to discover at least two new types of drugs—drugs which increase statin efficacy by altering regulation of the HMGCR gene (specifically alternative splicing), as well as drugs which alter regulation of HMGCR splicing and thus may lower LDL cholesterol or raise HDL cholesterol independent of statin treatment.

The methods of the invention, including diagnostic and prognostic methods evaluating a patient's likelihood of response to a HMGCR inhibitor, methods of identifying agents that provide for a desired HMGCR isoform expression profile, methods of treatment (e.g., modulating a cholesterol parameter such as at least one or more of total cholesterol, LDL cholesterol, IDL cholesterol, HDL cholesterol, ApoB, and/or ApoA1), find particular application in the context of patients who have failed prior HMGCR inhibitor therapy (referred to as "treatment failure patients" (or "treatment failures")). "Treatment failure patients" include those who have not exhibited a clinically significant response to prior HMGCR inhibitor therapy ("non-responders"), or who have exhibited a clinically significant response to prior HMGCR inhibitor therapy, but in whom such a clinically significant response has not been maintained (sometimes referred to as "relapse"). Such patients can particularly benefit from the methods disclosed herein, since identification of their HMGCR isoform status can provide direction to the clinician in selecting therapy, and thus avoid further unnecessary and/or unsuccessful treatment regimen with drugs to which the patient is not likely to respond. In addition, these patients represent those who are in needed of drugs that provide for a desired HMGCR isoform expression profile.

Other features, embodiments and various advantages of the invention will be readily apparent to the ordinarily skilled artisan upon reading the disclosure herein.

BRIEF DESCRIPTION OF THE DRAWINGS

FIG. 2 is a schematic illustrating various aspect of the ER and peroxisome (or statin-resistant) HMGCR transcripts and isoforms.

FIG. 3B is a schematic for a HMGCR(12-14) variant isoform assay useful in the invention.

FIG. 3C is a set of graphs showing the distribution of changes in major plasma lipids with simvastatin 40 mg/d (n=944).

FIGS. 4A and 4B are a collection of tables and graphs showing the association of change in HDL cholesterol with the change in HMGCR isoform transcripts (HMGCR(12-13) and HMGCR(12-14)) in Caucasians and African American populations at a "low dose" of simvastatin (1.8 uM).

FIGS. 10A and 10B are a collection of tables and graphs showing the association of fold change in HDL cholesterol with a fold change in the spliced HMGCR transcript excluding exon 13 ("12-14 fold change", indicative of the fold change in HMGCR(12-14) mRNA (as measured in vitro) and unspliced HMGCR transcript (HMGCR(12-13)) in cells of African Americans, where the cells are exposed to a "high dose" of simvastatin (14.5 uM).

Figure 1:
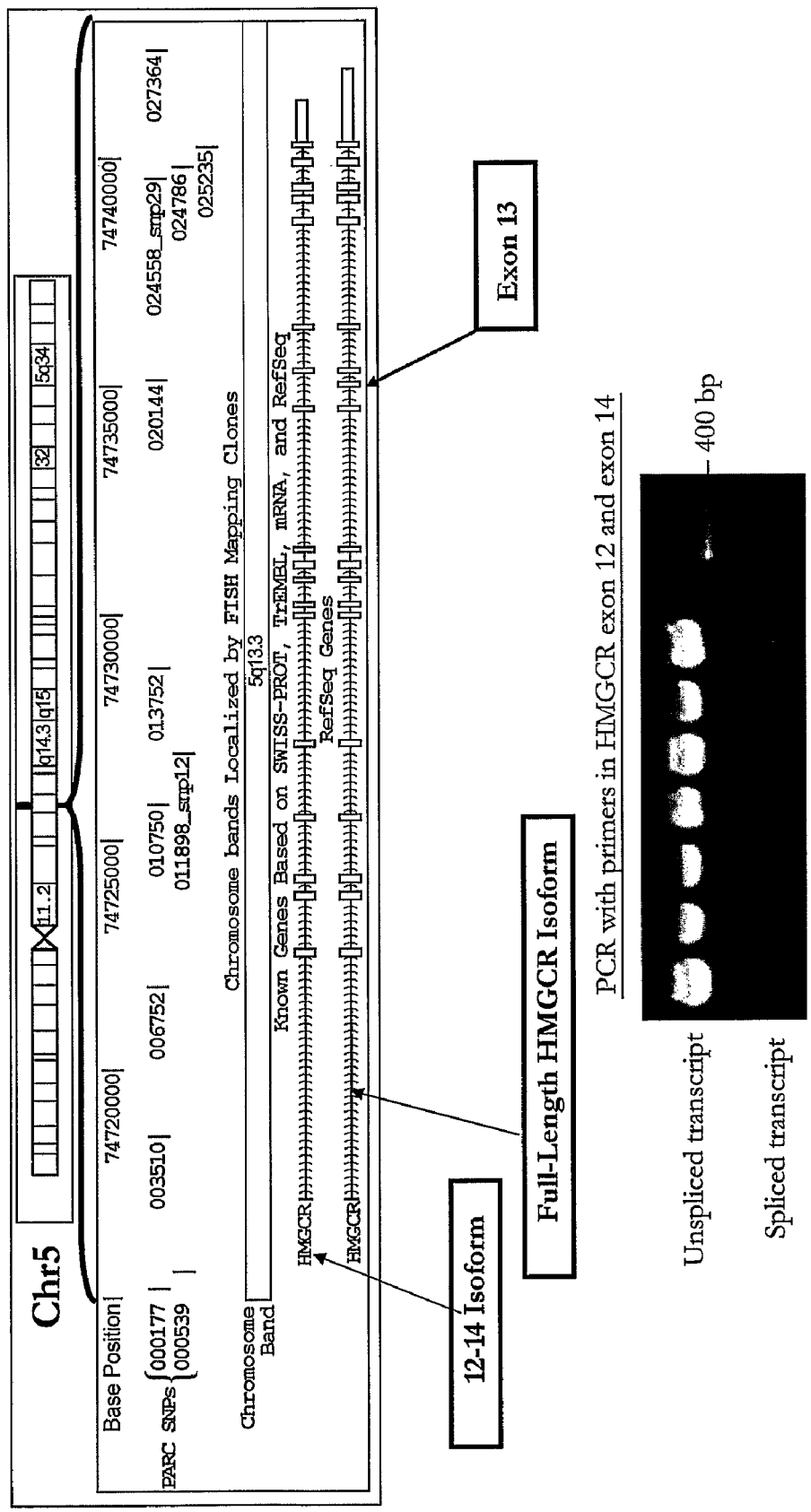
FIG. 1 provides a schematic showing the human HMGCR mRNAs encoding the full-length HMGCR isoform ("unspliced" or "normal" HMGCR isoform) and 12-14 HMGCR isoform ("spliced", also referred to herein as HMGCR(12-14)), and illustrating the presence of Exon 13 in the normal, but not in the 12-14 HMGCR isoform, as well as a photograph of a gel showing RT-PCR products amplified from lymphocyte RNA using primers in exon 12 and exon 14 thus demonstrating that both the normal and HMGCR(12-14) mRNAs are expressed in this cell type.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a HMGCR inhibitor" includes a plurality of such inhibitors and reference to "the sample" includes reference to one or more samples and equivalents thereof known to those skilled in the art, and so forth.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention is based on the discovery that variation in the extent of expression of the HMGCR(12-14) transcript in response to HMGCR inhibitor treatment (e.g., statin) is associated with the drug's widely varying efficacy in its ability to reduce total cholesterol, as well as to reduce LDL-cholesterol and raise HDL-cholesterol.

In addition, the inventors have discovered that expression of the HMGCR(12-14) splice variant and the HMGCR(12-13) full-length gene are indicators of modulation of HDL cholesterol levels following administration of a HMGCR inhibitor, such as a statin.

The invention thus contemplates a test to predict effectiveness of an HMGCR inhibitor (e.g., statin) in reducing total cholesterol (TC), reducing LDL cholesterol, reducing IDL-cholesterol, reducing apoB, and/or increasing HDL cholesterol and increasing apoA1 in a patient.

The methods of the invention provide the means to identify a new drug class that can increase HDL cholesterol and/or apoA1. Such methods have much commercial potential since low HDL cholesterol and low apoA1 are strong independent predictors of cardiovascular disease risk and there are currently few drugs available for raising HDL-cholesterol or apoA1.

The invention also contemplates methods for identifying agents that, either alone or in combination with a known HMGCR inhibitor, provide for lowering of total cholesterol levels, lowering IDL cholesterol levels, lowering LDL cholesterol levels, and/or enhancing HDL cholesterol levels. Such agents include those that inhibit HMGCR activity without increasing expression of a statin-resistant HMGCR isoform, or that inhibit expression or activity of a statin-resistant HMGCR isoform.

DEFINITIONS

"HMGCR" as used herein refers to 3-hydroxy-3-methyl-glutaryl coenzyme A reductase and its isoforms, particularly human HMGCR and its isoforms. "ER HMGCR" refers to the HMGCR isoform found in the endoplasmic reticulum; "peroxisomal HMGCR" refers to the HMGCR isoform found in peroxisomes. Human peroxisomal HMGCR and ER HMGCR, and naturally-occurring allelic variants thereof, are of particular interest.

"HMGCR(12-13)" refers to a HMGCR mRNA having a 12-13 exon splice junction, and includes the full-length (or "normal" or "unspliced") HMGCR transcript. The unspliced HMGCR transcript is likely the major transcript having the 12-13 splice junction in most relevant cells, and is thought to be present primarily in the ER. In some contexts, which will be readily apparent to the ordinarily skilled artisan, HMGCR (12-13) refers to the polypeptide encoded by HMGCR(12-13) mRNA or is used generically to refer to both the mRNA and corresponding polypeptide.

"HMGCR(12-14)" refers to a HMGCR mRNA having a 12-14 exon splice junction, i.e., a splice variant of HMGCR lacking exon 13. The HMGCR(12-14) isoform is also referred to herein as a "statin-resistant HMGCR". HMGCR (12-14) is also referred to herein as a statin-resistant HMGCR isoform. In some contexts, which will be readily apparent to the ordinarily skilled artisan, HMGCR(12-14) refers to the polypeptide encoded by HMGCR(12-14) mRNA or is used generically to refer to both the mRNA and corresponding polypeptide.

"HMGCR(6-7)" refers to all HMGCR mRNAs having exons 6 and 7 and includes the full-length (or "normal" or "unspliced") HMGCR transcript, the transcript containing exon 13 (HMGCR(12-13)), and all known spliced HMGCR transcripts, including HMGCR(12-14). In some cases it is used to represent total HMGCR transcripts. In some contexts, which will be readily apparent to the ordinarily skilled artisan, HMGCR(6-7) refers to the polypeptide encoded by HMGCR(6-7) mRNA or is used generically to refer to both the mRNA and corresponding polypeptide.

"HMGCR isoform" as used herein refers to HMGCR isoform mRNA transcripts, as well HMGCR polypeptides that are encoded by mRNA transcripts produced from the HMGCR gene, but which differ in amino acid sequence due to maintenance or removal of different exons as a result of variation in splicing. "HMGCR isoform" is also used to refer to DNA encoding a HMGCR isoform polypeptide, which can be generated from a HMGCR isoform mRNA transcript (e.g., by reverse transcription). HMGCR isoform as used herein thus includes an HMGCR protein encoded by the full-length transcript from a HMGCR gene, as well as splice variants encoded by mRNAs that differ in sequence from the full-length HMGCR transcript. Thus, HMGCR(12-13) and HMGCR(12-14) are HMGCR isoforms of particular interest.

"Splice variant" as used herein refers to RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule from the same genomic sequence, where the different mRNA molecules may each encode different amino acid sequences. The term splice variant also refers to the proteins encoded by such alternatively spliced RNAs, as well as to cDNA molecules produced from such RNA transcripts.

"HMGCR inhibitor" as used herein refers to an agent that inhibits HMGCR activity, particularly activity of full length HMGCR, e.g., to facilitate a reduction in serum cholesterol, particularly serum LDL cholesterol, in a subject.

"Statin" as used refers to group of HMGCR inhibitors that inhibit HMGCR activity, usually thought to be the activity of ER HMGCR, and include, for example, lovastatin, simvastatin, pravastatin, fluvastatin, atorvastatin, and rosuvastatin.

"HMGCR isoform expression profile" as used herein refers to relative levels of expression of one or more HMGCR isoforms, usually at least a HMGCR(12-14) isoform, optionally an HMGCR(12-13) isoform, optionally total HMGCR expression. For example, a cell exhibits a first HMGCR expression profile in the absence of HMGCR inhibitor, and a second HMGCR isoform expression profile in the presence of HMGCR inhibitor, in which at least HMGCR(12-14) expression is elevated in the second HMGCR expression profile.

"Total HMGCR expression" or "tHMGCR" or "total HMGCR" refers to a combined measure of expression of at least the HMGCR(12-14) and HMGCR(12-13) isoforms.

"Fold change" as used in the context of gene product expression generally refers to a level of expression calculated as a level of HMGCR isoform expression in the presence of an HMGCR inhibitor relative to a level of HMGCR isoform expression in the absence of a HMGCR inhibitor (e.g., in a control cell, which may be a different cell of the same type as the test cell or the treated cell prior to treatment), which expression levels are normalized by expression levels of a control gene that is not significantly affected by the presence of the HMGCR inhibitor. "Fold increase" and "fold decrease" indicate an increased fold change and decreased fold change, respectively.

Where HMGCR isoform expression is presented as ratio of expression levels, the ratio is calculated a fold change in a selected HMGCR isoform expression level divided by a fold change in total HMGCR expression. This can be represented by the formula:

$$\frac{\Delta HMGCR \text{ isoform}}{\Delta tHMGCR}$$

where $\Delta HMGCR$ isoform represents a change of the expression level of a selected hm isoform (e.g., HMGCR(12-14) or HMGCR(12-13)) in the presence of a HMGCR inhibitor relative to a baseline expression level in the absence of the HMGCR inhibitor (in a control cell), and $\Delta tHMGCR$ (also referred to as $\Delta$ total HMGCR) is a change of expression level of total HMGCR in the presence of the HMGCR inhibitor relative to a baseline total HMGCR expression level in the absence of the HMGCR inhibitor (in a control cell). Dividing the fold change in expression level of a selected HMGCR isoform by the fold change in total HMGCR provides a second round of normalization (the first being normalization against a control gene, as described above for "fold change") and separates the effects on total gene transcription from alternative splicing.

A "cholesterol level" herein, such as "total cholesterol level", "LDL cholesterol level", "IDL cholesterol level" and "HDL cholesterol level", generally refers to levels of total cholesterol, LDL cholesterol, IDL cholesterol, or HDL cholesterol in serum of a subject, unless specifically indicated otherwise.

A "serum cholesterol parameter" refers to a direct or indirect measure of serum cholesterol, usually at least one of a total cholesterol level, an LDL cholesterol level, an IDL cholesterol level, a HDL cholesterol level, an ApoB level and an ApoA1 level.

The term "infer" or "inferring", when used in reference to a HMGCR inhibitor (e.g., statin) response, means estimating the probability of a subject's likelihood of response to a HMGCR inhibitor (e.g., statin) based on the evaluation of HMGCR(12-14) expression in response to exposure of the subject's cells to a HMGCR inhibitor of interest.

"Response to a HMGCR inhibitor" as used herein generally means, after administration of a normally effective amount of a HMGCR inhibitor, a subject responds in at least one serum cholesterol parameter such as reduction in total cholesterol, reduction in LDL cholesterol, or increase in HDL cholesterol, usually at least a reduction in LDL cholesterol. It will be readily appreciated by the ordinarily skilled artisan that "responsiveness" with respect to a HMGCR inhibitor therapy is relative and should be viewed in the context of, for example, the subject's pre-therapy (baseline) total cholesterol, LDL cholesterol, and/or HDL cholesterol levels, as well as parameters relating to the patient's health, particularly with respect to other risk factors for coronary heart disease. Thus a response to a HMGCR inhibitor in a given subject can be viewed with respect to the value of an incremental improvement in reduction of total cholesterol, an incremental improvement in reduction of LDL cholesterol, and/or an incremental improvement in an increase in HDL cholesterol.

"Clinically significant response" as used herein refers to a subject's response, after administration of a HMGCR inhibitor and/or other drug, in at least one serum cholesterol parameter such as reduction in total cholesterol, reduction in LDL cholesterol, or increase in HD-L cholesterol, usually at least a reduction in LDL cholesterol, such that the subject receives an acceptable therapeutic benefit, e.g., reduction of LDL cholesterol to an acceptable level, particularly in light of any additional coronary heart disease (CHD) risk factors.

"Overall therapeutic response" refers to a response of a subject to a selected therapy in terms of two or more combined serum cholesterol parameters, such as total cholesterol, IDL cholesterol, LDL cholesterol, or HDL cholesterol, usually at least LDL cholesterol, such the parameters are indicative of whether the subject has had a clinically significant response or not following therapy.

A "therapeutically effective amount" is meant to refer to an amount of a therapeutic agent, or a regimen of delivery of a therapeutic agent, effective to facilitate a desired therapeutic effect, e.g., reduction of total cholesterol levels, reduction of LDL cholesterol levels, increase in HDL cholesterol levels, and the like. The precise desired therapeutic effect will vary according to the condition to be treated, the formulation to be administered, and a variety of other factors that are appreciated by those of ordinary skill in the art.

By "selected dose", as used in the context of a dose of a HMGCR inhibitor, is meant a dose that provides the desired effect on one or more serum cholesterol parameters.

By "isolated" is meant that a compound is separated from all or some of the components that accompany it in nature. "Isolated" can also refer to the state of a compound separated from all or some of the components that accompany it during manufacture (e.g., chemical synthesis).

By "purified" is meant a compound of interest that has been separated from components that accompany it in nature. "Purified" can also be used to refer to a compound of interest separated from components that can accompany it during manufacture (e.g., in chemical synthesis). Typically, a compound is substantially pure when it is at least 50% to 60%, by weight, free from organic molecules with which it is naturally associated or with which it is associated during manufacture. Generally, the preparation is at least 75%, more preferably at least 90%, and most preferably at least 99%, by weight, of the compound of interest. A substantially pure compound can be obtained, for example, by extraction from a natural source, by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, HPLC analysis, etc.

"Enriched" means that a substance in a composition is manipulated by an experimentalist or a clinician so that it is present in at least a three-fold greater concentration by total weight, preferably at least 10-fold greater concentration, more preferably at least 100-fold greater concentration, and most preferably at least 1.000-fold greater concentration than the concentration of that antigen in the strain from which the antigen composition was obtained.

"Pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers.

As used herein the term "treating" in reference to a disorder means a reduction in severity of one or more symptoms associated with a particular condition. Therefore, treating a condition does not necessarily mean a reduction in severity of all symptoms associated with a condition and does not necessarily mean a complete reduction in the severity of one or more symptoms associated with a condition. "Treatment", as used in this context, covers any treatment of a symptomatic condition in a mammal, particularly in a human, and includes: (a) diagnosing and then preventing the condition from occurring in a subject who may be predisposed but has not yet been diagnosed as having it; (b) inhibiting the condition, i.e., arresting its development; and (c) relieving the condition, i.e., causing regression of the condition. Similarly, the term "preventing" means prevention of the occurrence or onset of one or more symptoms associated with a particular condition and does not necessarily mean the complete prevention of the condition.

The terms "individual," "subject," and "patient," used interchangeably herein, generally refer to a human subject, unless indicated otherwise (e.g., in the context of a non-human mammal useful in an in vivo model (e.g., for testing drug toxicity), which generally refers to murines, simians, canines, felines, ungulates and the like (e.g., mice, rats, other rodents, rabbits, dogs, cats, swine, cattle, sheep, horses, primates).

As used herein, the term "target nucleic acid region" or "target nucleic acid" or "target molecules" refers to a nucleic acid molecule with a "target sequence" to be detected (e.g., by amplification). The target nucleic acid in the present invention is usually a HMGCR transcript, usually a splice variant encoding a statin-resistant isoform of HMGCR, specifically HMGCR(12-14). The target sequence normally is one that defines an HMGCR isoform transcript from other HMGCR isoforms encoded by the same gene, e.g., by detection of a particular splice junction present in the HMGCR isoform of interest, e.g., detection of the exon 12-14 splice junction to detect a statin-resistant HMGCR isoform transcript. Where detection is by amplification, other sequences in addition to the target sequence may or may not be amplified with the target sequence.

The term "target sequence" or "target nucleic acid sequence" refers to the particular nucleotide sequence of the target nucleic acid to be detected (e.g., through amplification). The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is originally single-stranded, the term "target sequence" also refers to the sequence complementary to the "target sequence" as present in the target nucleic acid, e.g., present in an amplification product generated from a mRNA encoding an HMGCR isoform transcript of interest. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence.

The term "primer" or "oligonucleotide primer" as used herein, refers to an oligonucleotide that acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products; This denaturation step is typically affected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeably herein, refers to a structure comprised of a polynucleotide, as defined above, that contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with its use in specific detection of all or a portion of a target sequence of a target nucleic acid, and are usually are in the range of between 8 to 100 nucleotides in length, such as 8 to 75, 10 to 74, 12 to 72, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. The typical probe is in the range of between 10-50 nucleotides long, such as 15-45, 18-40, 20-30, 21-28, 22-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Probes contemplated herein include probes that include a detectable label. For example, when an "oligonucleotide probe" is to be used in a 5' nuclease assay, such as the TaqMan™ assay, the probe includes at least one fluorescer and at least one quencher, where the probe is digested by a 5' endonuclease activity so as to provide for a detectable signal as a result of specific binding of probe to any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range.

The terms "hybridize" and "hybridization" refer to the formation of complexes between nucleotide sequences that are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent.

By "selectively bind" is meant that the molecule binds preferentially to the target of interest or binds with greater affinity to the target than to other molecules. For example, a DNA molecule will bind to a substantially complementary sequence and not to unrelated sequences.

The term "stringent conditions" refers to conditions under which a primer will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes between complementary binding members, e.g., between probes and complementary targets in a sample, e.g., duplexes of nucleic acid probes, such as DNA probes, and their corresponding nucleic acid targets that are present in the sample, e.g., their corresponding mRNA analytes present in the sample.

"Stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mnM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a probe. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55. ° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37. ° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

A $T_m$ is the temperature in degrees Celsius at which 50% of a polynucleotide duplex made of complementary strands hydrogen bonded in anti-parallel direction by Watson-Crick base pairing dissociates into single strands under conditions of the experiment. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25° C. below the $T_m$. $T_m$ may be predicted according to a standard formula, such as:

$$T_m = 81.5 + 16.6 \log [X^+] + 0.41(\% \, G/C) - 0.61(\% \, F) - 600/L$$

where $[X^+]$ is the cation concentration (usually sodium ion, $Na^+$) in mol/L; (% G/C) is the number of G and C residues as a percentage of total residues in the duplex; (% F) is the percent formamide in solution (wt/vol); and L is the number of nucleotides in each strand of the duplex.

As used herein, a "biological sample" refers to a sample of tissue or fluid isolated from a subject, which, depending on the context in which the term is used, generally refers to samples appropriate for in vitro analysis of serum cholesterol levels or samples containing cells suitable for analysis of HMGCR isoform expression, particularly HMGCR(12-14) isoform expression. Typical samples of interest include, but are not necessarily limited to, blood, plasma, serum, and blood cells (e.g., lymphocytes, and the like). Where the samples involve cells for analysis, the samples can be provided as in vitro cell culture constituents including but not limited to conditioned media resulting from the growth of cells and tissues in culture medium.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Overview

The present invention is based on the discovery that expression of a specific HMGCR mRNA splice variant (HMGCR (12-14)) in response to statin treatment is correlated with the drug's efficacy in its ability to reduce total cholesterol, to reduce LDL-cholesterol, to reduce IDL-cholesterol, and to raise HDL-cholesterol. In short, an increase in HMGCR(12-14) expression in a patient's cells following exposure of the cells to a statin indicates the patient is likely to have reduced efficacy to statin therapy with respect to lowering total cholesterol and/or lowering IDL, LDL and apoB levels (e.g., a patient with greater up-regulation of HMGCR(12-14) is likely to have lower reduction of total cholesterol, IDL cholesterol, LDL cholesterol, and apoB). An increase in HMGCR (12-14) expression is also associated with greater statin-induced increases in apoA1, suggesting that patients with increased HMGCR(12-14) expression are likely to respond to statin in this manner.

The magnitude of the increase in HMGCR(12-14) mRNA expression was significantly correlated with the absolute differences in plasma LDL-cholesterol that had been observed in these subjects with statin treatment in vivo. The inventors found that the greater the up-regulation of HMGCR(12-14) expression in patient cells treated in vitro with a statin, the smaller the decrease in total cholesterol, IDL cholesterol and LDL-cholesterol.

The inventors also found an association of HMGCR(12-14) expression, HMGCR(12-13) expression and total HMGCR expression (the latter being in a subject other than an African American subject) with modulation of HDL cholesterol levels in response to HMGCR inhibitor therapy is both race-dependent and sensitive to HMGCR inhibitor dose.

The invention thus contemplates a test to predict efficacy of an HMGCR inhibitor (e.g., statin) in reducing total cholesterol (TC), reducing IDL cholesterol, reducing LDL cholesterol, and/or increasing HDL cholesterol in a patient. The methods of the invention in this aspect can be used to infer whether a patient's cholesterol levels are more likely to be reduced by statin treatment, and to select or adjust cholesterol-lowering therapy accordingly.

Since conventional HMGCR inhibitors show reduced inhibition of enzymatic activity of the HMGCR(12-14) isoform, any agent that acts through a mechanism that reduces or prevents creation of HMGCR(12-14) can serve to increase statin efficacy with regard to LDL cholesterol reduction. Thus the invention also contemplates methods for identifying agents that, either alone or in combination with a known HMGCR inhibitor, provide for lowering of TC levels, lowering LDL cholesterol levels, lowering IDL cholesterol levels, lowering apoB levels, and/or enhancing HDL cholesterol levels and/or enhancing apoA1 levels. Such agents include those that inhibit HMGCR activity without increasing HMGCR (12-14) expression, or that inhibit HMGCR(12-14) expression or activity. The invention further contemplates identification of a therapeutic dose of a HMGCR inhibitor, that provides for a desirable HMGCR expression profile in cells of a subject to be treated.

The ability to identify a new drug class that can increase HDL cholesterol and/or apoA1 has much commercial potential since low HDL cholesterol and low apoA1 are strong predictors of cardiovascular disease risk and there are currently few drugs available for raising HDL-cholesterol and apoA1.

Detection of HMGCR Isoform Expression

An aspect of the present invention is to provide diagnostic assays for evaluating expression of an HMGCR isoform (i.e., a HMGCR(12-14) isoform and/or, in some embodiments, evaluating expression of HMGCR(12-13) and/or total HMGCR expression) in a sample (e.g., a nucleic acid sample from a patient cell). As noted above, the nucleotide sequence of the human HMGCR, which is encoded by the complete transcript of the HMGCR gene, is found at GenBank Accession No. NM_000859. The nucleotide sequence of the human HMGCR(12-14), which is a splice variant lacking exon 13 of the human HMGCR gene, is found at GenBank Accession no. BC033692.

In general, HMGCR isoform expression is assessed in any suitable cell, in which expression can vary according to the assay to be conducted. For example, where the HMGCR isoform expression is to be assessed to evaluate a subject's sensitivity to a HMGCR inhibitor therapy, the cell is any suitable cell from the patient in which HMGCR(12-14) isoforms are normally expressed. Cells of particular interest include, but are not necessarily limited to lymphocytes, monocytes, adipocytes, myocytes (muscle cells), fibroblasts and epithelial cells (e.g., mucosal epithelial cells, dermal cells), and other such cells which express HMGCR(12-14). Blood-derived cells such as lymphocytes and monocytes are of particular interest due to, for example, the ease with which they can be obtained from a patient in a sufficient number for conducting an assay. Where the assay is to assess the effect of a candidate agent upon HMGCR isoform expression, as in a drug screening assay, the cell can be any suitable cell in which at least the HMGCR(12-14) isoform is expressed, such as a human cell (e.g., a patient-derived cell) or can be a recombinant cell.

Analysis of HMGCR isoform expression can be accomplished in a variety of ways using methods that are well known in the art. In general, isoform expression can be assessed by analysis gene products of the genes encoding the isoforms, e.g., analysis at the RNA or protein levels, with RNA analysis being generally of more interest. Nucleic acid-based and protein-based methods of analysis are described in more detail below.

Analysis of HMGCR Isoform Transcripts

In one embodiment of particular interest, HMGCR isoform expression levels are assessed by analysis of HMGCR transcription levels. Any biological sample that comprises a cell that is capable of expressing HMGCR isoforms, usually at least a HMGCR(12-14) isoform and a HMGCR(12-13) isoform, is suitable for use in the methods of the invention. Exemplary cells suitable for analysis are described below and will vary with the goal of the assay to be performed. For example, where one wishes to assess whether a subject will respond to a HMGCR inhibitor therapy, the cells are cells from the subject, usually cells obtained from a blood sample, such as lymphocytes. Where one wishes to assess the activity of a candidate agent in modulating HMGCR(12-14) expression and, optionally HMGCR(12-13), the cells can be any suitable cell, usually a mammalian cell more usually a human cell, in which drug screening is suitable and desired.

After exposure of the cell to drug or candidate agent, the sample may be processed so as to isolate the polynucleotides therein. Methods for isolating mRNA and for preparing cDNA from mRNA are well known in the art, and kits for carrying out such methods are commercially available. Alternatively, whole cells may be used without isolation of the polynucleotides contained therein. For example, in some embodiments HMGCR isoform expression is assessed by in situ hybridization. Where in situ hybridization is used, HMGCR isoform expression can involve not only assessing relative differences in HMGCR(12-14) expression levels (and/or HMGCR(12-13) expression levels), and but also involves analysis of the effect of drug upon trafficking of the transcripts to various intracellular organs (e.g., ER versus peroxisome).

In one embodiment, a sample of RNA is obtained from a cell (e.g., in the presence and absence of a HMGCR inhibitor, a candidate agent, or both) and prepared in accordance with conventional methods, e.g., lysing cells, removing cellular debris, and separating the RNA from other cellular components as needed, etc. See, e.g., Molecular Cloning, A Laboratory Manual, 2nd ed. (eds. Sambrook et al.) CSH Laboratory Press, Cold Spring Harbor, N.Y. 1989.

The level of expression of an HMGCR isoform can be detected at several levels. Using standard methodology well known in the art, assays for the qualitative and/or quantitative detection of an HMGCR isoform, particularly a HMGCR(12-14) isoform transcript can be designed. Exemplary methods include, but are not necessarily limited to hybridization analysis (e.g., Northern hybridization assays to detect RNA directly, or hybridization analysis of cDNAs generated from RNA in the sample), in situ hybridization assays (detection of transcripts in cells), PCR assays (e.g., involving amplification of nucleic acid having a target sequence with specific primers), denaturing gradient gel electrophoresis, and other assays which will be readily appreciated by the ordinarily skilled artisan. See, for example, Maniatis, Fitsch and Sambrook, *Molecular Cloning A Laboratory Manual*, (1982) or *DNA Cloning*, Volumes I and II (D. N. Glover ed. 1985), or *Current Protocols in Molecular Biology*, Ausubel, F. M. et al., (Eds), Wiley & Sons, Inc.

Primers and/or probes used in nucleic acid-based detection methods can be designed based on target regions, which contain sequences unique to the HMGCR isoform sequence to be detected. For example, a target region of a human HMGCR(12-14) sequence contains the 12-14 splice junction, while a target region of a human unspliced or other HMGCR sequence contains the 12-13 splice junction.

In particular embodiments, the primer(s) and/or probe(s) can be detectably labeled. Exemplary detectable labels are described below. While particular detectable labels and methods of detectably labeling primers and probes are provided below in various contexts, the ordinarily skilled artisan will readily recognize that such exemplified detectable labels and methods may not be specific for use in the particular assays in which they are provided as examples, and instead can be applied to different nucleic acid-based detection methods described herein.

Detection Using PCR-Based Methods

For example, where detection involves a PCR-based method, nucleic acid can be amplified with primers that only amplify a target region unique to an isoform(s) of interest, such as the 12-14 exon splice junction in the HMGCR(12-14) isoform or the 12-13 exon splice junction in HMGCR(12-13). If the target region is not present, amplification of the nucleic acid will not take place. In this regard, PCR may be used to detect a particular HMGCR isoform. The use of the polymerase chain reaction is described in a variety of publications, including, e.g., "PCR Protocols (Methods in Molecular Biology)" (2000) J. M. S. Bartlett and D. Stirling, eds, Humana Press; and "PCR Applications: Protocols for Functional Genomics" (1999) Irmis, Gelfand, and Sninsky, eds., Academic Press. Such PCR-based methods may involve isolating template nucleic acid (mRNA or, where the mRNA is reverse transcribed, cDNA) from the sample, contacting the nucleic acid with one or more primers that specifically hybridize with a nucleic acid encoding a HMGCR isoform of interest (usually at least a HMGCR(12-14) isoform) under conditions such that hybridization and amplification of the template nucleic acid molecules in the sample occurs, and detecting the presence, absence, and/or relative amount of an amplification product, that can be compared to that of a control sample.

Detection of an amplification product of the expected size will be an indication that a HMGCR isoform-encoding nucleic acid of interest is present in the test nucleic acid sample. Parameters such as hybridization conditions and primer length, and position of the sequence unique to the HMGCR isoform of interest may be chosen such that hybridization and/or primer extension will not occur unless a nucleic acid having a sequence complementary to that of the primer(s) is also present in the sample nucleic acid. Those of ordinary skill in the art are well aware of how to select and vary such parameters. See, e.g., Saiki et al. (1986) Nature 324:163; and Saiki et al (1989) Proc. Natl. Acad. Sci. USA 86:6230. The primers can further be designed such that the length of the amplification products will be indicative of the HMGCR isoform encoded.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification may be labeled, so as to incorporate the label into the amplification product.

In one embodiment, PCR is used in combination with matrix assisted laser desorption/ionization time-of-flight mass spectrometry (MALDI-TOF) to determine the presence of a HMGCR(12-14) isoform-encoding nucleic acid. See, e.g., Tang et al., Journal of Proteome Research (2004) 3:218-227 and Storm et al., Methods Mol Biol (2003) 212:241-262. By way of illustration and not limitation, the MassARRAY Homogenous MassEXTEND™ Assay commercially available from Sequenom Inc. (San Diego, Calif.) can be used to determine, for example, the presence of the 12-14 splice junction target of a nucleic acid encoding the HMGCR(12-14), the presence of the 12-13 splice junction, and/or the presence of a splice junction shared by both HMGCR isoforms (e.g. to assess total HMGCR expression).

Real Time PCR-Based Methods

In one embodiment of particular interest, the HMGCR isoform-encoding nucleic acid is detected using any of a variety of real time PCR methods, which methods allow for detection of PCR product created during the exponential phase of amplification to facilitate determination of the amount of the amplified transcript present in the sample. In general, real time PCR (RT-PCR) involves use of amplification primers, and a detectably labeled probe. For example, in the present methods, the probe can be designed to specifically hybridize to a target region of a HMGCR isoform-encoding sequence, such as the 12-14 splice junction of the HMGCR (12-14) or the 12-13 splice junction of the HMGCR(12-13). Exemplary RT-PCR methods are described in, for example, U.S. Pat. No. 5,210,015; and U.S. Pat. No. 6,548,250.

Accordingly, in one embodiment, the invention features a probe suitable for use in RT-PCR, which probe specifically hybridizes to a HMGCR isoform target region (e.g., a 12-14 splice junction of a nucleic acid encoding HMGCR(12-14)). Such probes generally include a both a fluorophore and quenching agent attached to the probe. When the probe is intact, the fluorescence of the fluorophore is quenched by the quencher. If the probe specifically hybridizes to a target region, the probe is cleaved between the fluorophore and the quencher, allowing full emission of the fluorophore fluorescence. Quenching involves transfer of energy between the fluorophore and the quencher, the emission spectrum of the fluorophore and the absorption spectrum of the quencher overlap (e.g., as in where the fluorophore is rhodamine 590 and the quencher is crystal violet). In a related embodiment, the probe is cleaved when amplification from a primer positioned 5' of the probe occurs. Further exemplary embodiments of this aspect of the invention are described in, e.g., U.S. Pat. No. 5,210,015; and U.S. Pat. No. 6,548,250.

Hybridization Analysis

Hybridization with the variant sequence may also be used to determine the presence of a HMGCR isoform-encoding nucleic acid. Hybridization analysis can be carried out in a number of different ways; including, but not limited to: Southern blots, Northern blots, dot blots, microarrays, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. For instance, identification of a polymorphism in a nucleic acid sample can be performed by hybridizing both sample and control nucleic acids to high density arrays containing hundreds or thousands of oligonucleotide probes. Cronin et al. (1996) Human Mutation 7:244-255; and Kozal et al. (1996) Nature Med. 2:753-759.

Hybridization reactions can be performed under conditions of different stringency. Conditions that increase stringency of a hybridization reaction are widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. Examples of stringent conditions are hybridization and washing at 50° C. or higher and in 0.1×SSC (9 mM NaCl/0.9 mM sodium citrate).

Stringent conditions for both DNA/DNA and DNA/RNA hybridization are as described by Sambrook et al. Molecular Cloning, A Laboratory Manual, 2nd Ed., Cold Spring Harbor Laboratory Press, Cold Spring Harbor, N.Y., 1989, herein incorporated by reference. For example, see page 7.52 of Sambrook et al. Alternatively, various methods are known in the art that utilize oligonucleotide ligation as a means of detecting polymorphisms. See, e.g., Riley et al. (1990)

Nucleic Acids Res. 18:2887-2890; and Delahunty et al. (1996) Am. J. Hum. Genet. 58:1239-1246.

The hybridizaton probes may be coupled to labels for detection. As with primers, several methods and compositions for derivitizing oligonucleotides with reactive functionalities that permit the addition of a label are known in the art. For example, several approaches are available for biotinylating probes so that radioactive, fluorescent, chemiluminescent, enzymatic, or electron dense labels can be attached via avidin. See, e.g., Broken et al., Nucl. Acids Res. (1978) 5:363-384 which discloses the use of ferritin-avidin-biotin labels; and Chollet et al. Nucl. Acids Res. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) Nucl. Acids Res. 15:3131-3139, Gibson et al. (1987) Nucl. Acids Res. 15:6455-6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) Nuc. Acids Res. 13:4485-4502 and Spoat et al. (1987) Nucl. Acids Res. 15:4837-4848. A comprehensive review of methodologies for labeling DNA fragments is provided in Matthews et al., Anal. Biochem. (1988) 169:1-25.

For example, probes may be fluorescently labeled by linking a fluorescent molecule to the non-ligating terminus of the probe. Guidance for selecting appropriate fluorescent labels can be found in Smith et al., Meth. Enzymol. (1987) 155:260-301; Karger et al., Nucl. Acids Res. (1991) 19:4955-4962; Haugland (1989) Handbook of Fluorescent Probes and Research Chemicals (Molecular Probes, Inc., Eugene, Oreg.). Preferred fluorescent labels include fluorescein and derivatives thereof, such as disclosed in U.S. Pat. No. 4,318,846 and Lee et al., Cytometry (1989) 10:151-164, and 6-FAM, JOE, TAMRA, ROX, HEX-1, HEX-2, ZOE, TET-1 or NAN-2, and the like.

Additionally, probes can be labeled with an acridinium ester (AE). Current technologies allow the AE label to be placed at any location within the probe. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

In some embodiments, hybridization of the target nucleic acid (e.g., encoding a HMGCR isoform of interest) is accomplished using a support, usually a solid support, having probe bound to a surface, e.g., to capture amplicons of target nucleic acid by hybridization of the target to the probe. Examples of preferred types of supports for immobilization of the probe include controlled pore glass, glass plates, polystyrene, avidin-coated polystyrene beads, cellulose, nylon, acrylamide gel and activated dextran.

Where a support is used, the probe may be attached to the support in a variety of manners. For example, the probe may be attached to the support through a 3' or 5' terminal nucleotide of the probe. In some embodiments, the probe is attached to the support by a linker that serves to distance the probe from the support surface. The linker is usually at least 15-30 atoms in length, more preferably at least 15-50 atoms in length. The required length of the linker will depend on the particular solid support used. For example, a six atom linker is generally sufficient when high cross-linked polystyrene is used as the solid support.

A wide variety of linkers are known in the art which may be used to attach the probe to the support. The linker may be formed of any compound which does not significantly interfere with the hybridization of the target sequence to the probe attached to the support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred. The linkages between the support, the linker and the probe are normally not cleaved during removal of base protecting groups under basic conditions at high temperature. Examples of preferred linkages include carbamate and amide linkages.

Arrays

The methods of the invention may further include the use of an array of oligonucleotides (i.e., "probes"), where oligonucleotide probes at discrete positions on the array are complementary to one or more of the HMGCR isoform-encoding nucleic acid to be detected. Such an array may comprise a series of oligonucleotides, each of which can specifically hybridize to a different HMGCR isoform-encoding sequence. For examples of arrays, see, e.g., Ramsay (1998) Nature Biotech. 16:40-44; Hacia et al. (1996) Nature Genetics 14:441-447; Lockhart et al. (1996) Nature Biotechnol. 14:1675-1680; and De Risi et al. (1996) Nature Genetics 14:457-460.

Accordingly, an array to be used in accordance with the methods of the invention may include nucleic acids that specifically hybridize to a HMGCR(12-14) isoform-encoding sequence (e.g., a probe that is complementary to a 12-14 splice junction target region), as well as to a HMGCR(12-13) isoform-encoding nucleic acid (e.g., a probe that is complementary to a 12-13 splice junction target region), and optionally to an internal standard (e.g., a probe that is complementary to a nucleic acid encoding a control gene, usually one encoding a transcript for which expression is not significantly affected by HMGCR inhibitor). Arrays of interest may be addressable and may further comprise other genetic sequences of interest. The oligonucleotide probe sequence on the array should generally be at least about 5 to about 12 nt in length, at least about 15 nt, at least about 18 nt, at least about 20 nt, or at least about 25 nt, or may be the length of a desired target region, or may extend into the flanking regions to generate fragments of 100 to 200 nt in length.

A number of methods are available for creating microarrays of biological samples and the probes to be used therewith, such as arrays of DNA samples to be used in DNA hybridization assays. Exemplary are PCT Application Serial No. WO95/35505, published Dec. 28, 1995; U.S. Pat. No. 5,445,934, issued Aug. 29, 1995; and Drmanac et al. (1993) Science 260:1649-1652. Yershov et al. (1996) Genetics 93:4913-4918 describe an alternative construction of an oligonucleotide array. The construction and use of oligonucleotide arrays is reviewed by Ramsay (1998) supra.

Methods of using high density oligonucleotide arrays are known in the art. For example, Milosavljevic et al. (1996)

Genomics 37:77-86 describe DNA sequence recognition by hybridization to short oligomers. See also, Drmanac et al. (1998) Nature Biotech. 16:54-58; and Drmanac and Drmanac (1999) Methods Enzymol. 303:165-178; The use of arrays for identification of unknown mutations is proposed by Ginot (1997) Human Mutation 10:1-10. Methods of producing large arrays of oligonucleotides are described in U.S. Pat. No. 5,134,854 (Pirrung et al.), and U.S. Pat. No. 5,445,934 (Fodor et al.) using light-directed synthesis techniques. Alternatively, microarrays are generated by deposition of pre-synthesized oligonucleotides onto a solid substrate, for example as described in WO 95/35505.

Quantitative monitoring of gene expression patterns with a complementary DNA microarray is described in Schena et al. (1995) Science 270:467. Further discussion of use of arrays in gene expression analysis is provided in DeRisi et al. (1997) Science 270:680-686; and Wodicka et al. (1997) Nat. Biotech. 15:1-15.

In one particular embodiment of the invention, a sample from a subject is obtained and processed according to techniques well known in the art so as to isolate the nucleic acid in the sample. The nucleic acids of the sample may or may not be cleaved. The nucleic acid samples are then denatured and labeled. Labeling can be performed according to methods well known in the art, using any method that provides for a detectable signal either directly or indirectly from the nucleic acid fragment. In a preferred embodiment, the fragments are end-labeled, in order to minimize the steric effects of the label. For example, terminal transferase may be used to conjugate a labeled nucleotide to the nucleic acid fragments.

Suitable labels include biotin and other binding moieties; fluorochromes, e.g. fluorescein isothiocyanate (FITC), rhodamine, Texas Red, phycoerythrin, allophycocyanin, 6-carboxyfluorescein (6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), and the like. Where the label is a binding moiety, the detectable label is conjugated to a second stage reagent, e.g. avidin, streptavidin, etc. that specifically binds to the binding moiety, for example a fluorescent probe attached to streptavidin. Incorporation of a fluorescent label using enzymes such as reverse transcriptase or DNA polymerase, prior to any fragmentation of the sample, is also possible.

Oligonucleotide probes encoding the sequence to be tested are fabricated into an array on a substrate. The labeled sample is washed across the array of oligonucleotide probes and hybridization is allowed to occur. Hybridization of the labeled sequences is accomplished according to methods well known in the art. As set forth above, hybridization can be carried out under conditions varying in stringency, preferably under conditions of high stringency, e.g. 6×SSPE, at 65° C., to allow for hybridization of any complementary sequences having extensive homology to the probe on the array, usually having no more than one or two mismatches in a probe of 25 nucleotides in length, i.e. at least 95% to 100% sequence identity. It is understood that the above is for purposes of illustrations. The length of oligonucleotide probes on the array is an important factor in how sensitive hybridization will be to the presence of a mismatch. Usually oligonucleotides will be at least about 12 nt in length, more usually at least about 15 nt in length, preferably at least about 20 nt in length and more preferably at least about 25 nt in length, and will be not longer than about 35 nt in length, usually not more than about 30 nt in length.

Microarrays can be scanned to detect hybridization of the labeled genomic samples. Methods and devices for detecting fluorescently marked targets on devices are known in the art. Generally such detection devices include a microscope and light source for directing light at a substrate. A photon counter detects fluorescence from the substrate, while an x-y translation stage varies the location of the substrate. A confocal detection device that may be used in the subject methods is described in U.S. Pat. No. 5,631,734. A scanning laser microscope is described in Shalon et al. (1996) Genome Res. 6:639. A scan, using the appropriate excitation line, is performed for each fluorophore used. The digital images generated from the scan are then combined for subsequent analysis. For any particular array element, the ratio of the fluorescent signal from one Nucleic acid sample is compared to the fluorescent signal from the other Nucleic acid sample, and the relative signal intensity determined.

Methods for analyzing the data collected by fluorescence detection are known in the art. Data analysis includes the steps of determining fluorescent intensity as a function of substrate position from the data collected, removing outliers (i.e. data deviating from a predetermined statistical distribution), and calculating the relative binding affinity of the targets from the remaining data. The resulting data may be displayed as an image with the intensity in each region varying according to the binding affinity between targets and probes.

Internal Controls for Nucleic Acid-Based Assays

In certain embodiments, an internal control (IC) or an internal standard is added to serve as a control to show that any negative result is not due to failure of the assay. The use of the IC permits the control of the separation process, the amplification process, and the detection system, and permits the monitoring of assay performance and quantification for the sample(s). The IC can be included at any suitable point, for example, in the lysis buffer. In one embodiment, the IC comprises phage nucleic acid. Where a support is used in the assay, the solid support may additionally include probes specific to the internal standard (IC probe), thereby facilitating capture when using the IC probe. The IC probe can optionally be coupled with a detectable label that is different from the detectable label for the target sequence. In embodiments where the detectable label is a fluorophore, the IC can be quantified spectrophotometrically and by limit of detection studies.

In another embodiment, an IC, as described herein, is combined with RNA isolated from the sample according to standard techniques known to those of skill in the art, and described herein. The RNA is then reverse-transcribed using a reverse transcriptase to provide copy DNA. The cDNA sequences can be optionally amplified (e.g., by PCR) using labeled primers. The amplification products are separated, typically by electrophoresis, and the amount of radioactivity (proportional to the amount of amplified product) is determined. The amount of mRNA in the sample can then calculated where desired by comparison with the signal produced by the known standards.

Polypeptide-Based Analysis of HMGCR Isoform Expression

The invention also explicitly contemplates detecting a HMGCR isoform polypeptide in the assays of the invention, e.g., as a means of predicting a subject's sensitivity to a HMGCR inhibitor or as a means of assessing the effect of a candidate agent upon HMGCR(12-14) expression levels). As discussed in detail supra, the HMGCR(12-14) and full-length HMGCR polypeptides differ in that the HMGCR(12-14) lacks the amino acid sequence encoded by exon 13. Accordingly, antibodies that specifically bind a HMGCR(12-14) (as well as antibodies that specifically bind to HMGCR(12-13), if such is desired) so as to distinguish the HMGCR isoform from other HMGCR isoforms (e.g., so as to distinguish a HMGCR(12-14) polypeptide from an HMGCR polypeptide expressed from an unspliced transcript).

A number of methods are available for determining the expression level of a protein in a particular sample. For example, detection may utilize staining of cells or histological sections with labeled antibodies, performed in accordance with conventional methods. Cells can be permeabilized to stain intracellular molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. Alternatively, the secondary antibody conjugated to a fluorescent compound, e.g. fluorescein, rhodamine, Texas red, etc. The absence or presence of antibody binding may be determined by various methods, including flow cytometry of dissociated cells, microscopy, radiography, scintillation counting, etc.

Antibodies for detection of HMGCR(12-14) and/or HMGCR(12-13) can be produced according to methods well known in the art. As used herein, the term "antibodies" includes antibodies of any isotype, fragments of antibodies which retain specific binding to antigen, including, but not limited to, Fab, Fv, scFv, and Fd fragments, fusion proteins comprising such antibody fragments, detectably labeled antibodies, and chimeric antibodies and unless explicitly stated otherwise encompasses polyclonal antibodies and monoclonal antibodies. "Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies for a HMGCR(12-14) or HMGCR (12-13) isoform, particularly one that can distinguish between a HMGCR(12-13) isoform and a HMGCR(12-14) isoform. Antibodies useful in the invention may originate from any suitable animal including, but not limited to, rabbit, mouse, rat, and hamster.

Antibodies are prepared in accordance with conventional methods well known in the art. For preparing antibodies, a full-length HMGCR(12-14) polypeptide, a full-length HMGCR(12-13) polypeptide, or peptide of an HMGCR isoform which comprises a region specific to the HMGCR isoform (e.g., for the HMGCR(12-14) isoform, at least the amino acid sequence encoded at the 12-14 splice junction, or for the HMGCR(12-13) isoform, at least the amino acid sequence encoded at the 12-13 splice junction) is used as immunogen directly or conjugated to a known immunogenic carrier, e.g., KLH, pre-S HBsAg, other viral or eukaryotic proteins, or the like. In particular embodiment, various adjuvants may be employed, with a series of injections, as appropriate. In the case of monoclonal antibodies, after one or more booster injections, the spleen is isolated, the lymphocytes immortalized by cell fusion, and then screened for high affinity antibody binding. The immortalized cells, i.e., hybridomas, producing the desired antibodies may then be expanded. If desired, the mRNA encoding the monoclonal antibody heavy and light chains may be isolated and mutagenized by cloning in E. coli, and the heavy and light chains mixed to further enhance the affinity of the antibody. For further description, see Antibodies: A Laboratory Manual, Harlow and Lane eds., Cold Spring Harbor Laboratories, Cold Spring Harbor, N.Y., 1988.

Antibodies may be attached, directly or indirectly (e.g., via a linker molecule) to a solid support for use in a diagnostic assay to determine and/or measure the presence of a HMGCR isoform) polypeptide in a biological sample and/or to determine and/or measure the presence of the HMGCR isoform polypeptide in a biological sample. Attachment is generally covalent, although it need not be. Solid supports include, but are not limited to, beads (e.g., polystyrene beads, magnetic beads, and the like); plastic surfaces (e.g., polystyrene or polycarbonate multi-well plates typically used in an ELISA or radioimmunoassay (RIA), and the like); sheets, e.g., nylon, nitrocellulose, and the like; and chips, e.g., $SiO_2$ chips such as those used in microarrays. Accordingly, the invention further provides assay devices comprising antibodies specific for an HMGCR isoform (e.g., HMGCR(12-14)) polypeptide attached to a solid support.

A single antibody or a battery of different antibodies can then be used to create an assay device. Such an assay device can be prepared using conventional technology known to those skilled in the art. The antibody can be purified and isolated using known techniques- and bound to a support surface using known procedures. The resulting surface having antibody bound thereon can be used to assay a test sample, e.g., a biological sample, in vitro to detect a HMGCR(12-14) polypeptide. For example, antibodies which bind only to a HMGCR(12-14) polypeptide epitope (e.g., an amino acid sequence of the 12-14 splice junction) or which bind only to a HMGCR(12-13) polypeptide epitope (e.g., an amino acid sequence of the 12-13 splice junction) can be attached to the surface of a material. Alternatively, a plurality of specific antibodies, which may be arranged in an array, wherein antibodies specific for, for example, a HMGCR(12-14) and, optionally, a HMGCR(12-13) polypeptide, are attached to the solid support, can be used. A test sample is brought into contact with the antibodies bound to the surface of material. Specific binding can be detected using any known method. As one non-limiting example of how specific binding can be detected, once the test sample has been contacted with the antibodies bound to the solid support, a second, detectably-labeled antibody can be added, which recognizes a HMGCR isoform polypeptide epitope distinct from the epitope recognized by the solid support-bound antibody.

A variety of other reagents may be included in the assays to detect HMGCR(12-14) polypeptides. These include reagents such as salts, neutral proteins, e.g. albumin, detergents, etc., that are used to facilitate optimal protein-protein binding, and/or reduce non-specific or background interactions. Reagents that improve the efficiency of the assay, such as protease inhibitors, anti-microbial agents, etc. may be used. The components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

HMGCR Inhibitors

In one aspect the invention generally involves assessing whether administration of a HMGCR inhibitor to a patient will result in lowering total cholesterol levels, and particularly in lowering LDL cholesterol levels in the patient. The term "HMGCR inhibitor: is intended to include all pharmaceutically acceptable salts, esters, free acid and lactone forms of compounds which have HMGCR inhibitory activity and, therefore, such salts, esters, free acids and lactone forms is included within the scope of this invention. Methods for detecting HMGCR activity are well known in the art. See, e.g., Edwards et al. *J. Lipid Res.* (1979) 20:40-46.

HMGCR inhibitors of particular interest are drugs commonly referred to as "statins". Exemplary statins include, but are not limited to, lovastatin (MEVACOR™; see, U.S. Pat. No. 4,231,938); simvastatin (ZOCOR™; see, U.S. Pat. No. 4,444,784); pravastatin sodium (PRAVACHOL™; see, U.S. Pat. No. 4,346,227); fluvastatin sodium (LESCOL™; see, U.S. Pat. No. 5,354,772); atorvastatin (LIPITOR™; see, U.S. Pat. No. 5,273,995); rivastatin (also known as cerivastatin; see, U.S. Pat. No. 5,177,080); and rosuvastatin (CRESTOR). The structural formulas of these and additional HMG-CoA reductase inhibitors are described at page 87 of M. Yalpani, "Cholesterol Lowering Drugs," Chemistry & Industry, pp. 85-89 (Feb. 5, 1996).

In embodiments of particular interest, the HMG-CoA reductase inhibitor is simvastatin. Simvastatin is a lipid-lowering agent that is derived synthetically from fermentation product of *Aspergillus terreus*. After oral ingestion, simvastatin, in its inactive lactone form, is hydrolyzed to the corresponding beta-hydroxy acid form. The beta-hydroxy acid form is an inhibitor of HMGCR, and thus acts to inhibit conversion of HMG-CoA to mevalonate, which is an early and rate-limiting step in the biosynthesis of cholesterol.

Simvastatin is commercially available under the brand name ZOCOR™ for oral administration as 5 mg, 10 mg, 20 mg, 40 mg, and 80 mg tablets. It is generally used to reduce the risk of i) total mortality by reducing coronary death, ii) non-fatal myocardial infarction, iii) undergoing myocardial revascularization procedures, and iv) stroke or transient ischemic attack in patients with coronary heart disease and hypercholesterolemia. Package Insert ZOCOR™, 2002. Simvastatin is indicated for reducing total cholesterol (Total-C) low density lipoprotein cholesterol (LDL-C), apolipoprotein B and triglycerides, and increasing high density lipoprotein-cholesterol levels, in patients with primary hypercholesterolemia (heterozygous familial and nonfamilial) and mixed dyslipidemia (Fredrickson Type IIa and IIb). It is also used to treat patients with hypertriglyceridemia (Fredrickson Type IV hyperlipidemia) and patients with primary dysbetalipoproteinemia (Fredrickson Type III hyperlipidemia). Simvastatin is also used as an adjunct to other lipid lowering treatments (e.g., low density lipoprotein (apheresis).

Methods of Assessing Responsiveness to HMGCR Inhibitor Therapy

In one embodiment, the invention features methods for predicting the likely magnitude of a subject's response to a HMGCR inhibitor therapy, particularly a statin therapy. In general, such methods involve assessing HMGCR(12-14) expression in a cell from subject who is a candidate for, or undergoing, a HMGCR inhibitor therapy. In general, HMGCR(12-14) expression is assessed as a change in HMGCR(12-14) expression in the presence of a HMGCR inhibitor relative to HMGCR(12-14) expression in the absence of the HMGCR inhibitor.

Subjects

The methods of the invention are suitable for any subject for whom a HMGCR inhibitor therapy is proposed, or any subject who is undergoing HMGCR inhibitor therapy. For example, the subject can be one for whom a HMGCR inhibitor therapy is proposed due to presentation with one or more risk factors for a coronary artery disease, particularly a subject having an elevated serum total cholesterol level and/or elevated serum LDL cholesterol level, or a level of LDL cholesterol in a range that is considered to confer an increased risk of cardiovascular disease for that subject. The subject can also be one who is undergoing HMGCR inhibitor therapy, and assessment of response is desired. For example, where the subject is undergoing HMGCR inhibitor therapy, but is not responding to a desired degree, the methods of the invention can be used to determine whether adjusting HMGCR inhibitor therapy dosage (e.g., amount and/or frequency of dosing) would be beneficial, or whether the subject is not likely to respond as desired, and therapy should be changed entirely (e.g., by changing to a drug that lowers cholesterol by a different mechanism).

The table below provides a summary of serum levels of total cholesterol, LDL cholesterol, and HDL cholesterol level that are desired and that are considered to be indicative of disease or risk of disease in otherwise healthy humans.

|  | Desired Level | Disease Level |
| --- | --- | --- |
| Total Cholesterol | <200 mg/dl | >200 mg/dl |
| LDL Cholesterol | <130 mg/dl | >130 mg/dl |
| HDL Cholesterol | >40 mg.dl | <40 mg/dl |

An elevated level of LDL cholesterol is an independent risk factor for premature coronary heart disease (CHD), with a value of 160 mg/dl or greater designated as high-risk by the National Cholesterol Education Program Adult Treatment Panels I, II and III. Current goals of therapy for all patients with elevated LDL cholesterol include reducing levels to: (i) less than 160 mg/dl in those with at least one or more CHD risk factors; (ii) less than 130 mg/dl in those with 2 or more CHD risk factors; and (iii) less than 100 mg/dl in patients with established CHD or CHD risk equivalents, one of which is diabetes. Thus risk factors other than total and/or LDL cholesterol levels can be taken into account which may indicate the need for HMGCR inhibitor therapy for a subject, even where the total cholesterol and/or LDL cholesterol level alone may not be indicative of risk of disease.

Methods of identifying subjects for HMGCR inhibitor treatment are well known in the art. For example, determining cholesterol levels can be performed according to methods known in the art. It should be noted that since cholesterol is water insoluble, most serum cholesterol is carried by zlipoproteins (chylomicrons, VLDL, IDL, LDL, and HDL). The term "LDL" means LDL-cholesterol and "HDL" means HDL-cholesterol. The term "cholesterol" "total cholesterol" refers to (VLDL+IDL+LDL+HDL). LDL is sometimes referred to as "bad" cholesterol, because elevated levels of LDL correlate most directly with coronary heart disease. HDL is sometimes referred to as "good" cholesterol since high levels of HDL are associated with reduced risk for coronary heart disease.

Preferably, cholesterol is measured after a patient has fasted. In 2001, guidelines from the National Cholesterol Education Panel recommended that all lipid tests be performed fasting and should measure total cholesterol, HDL, LDL and triglycerides. The total cholesterol measurement, as with all lipid measurements, is typically reported in milligrams per deciliter (mg/dL). Typically, the higher the total cholesterol, the more at risk a subject is for heart disease. A value of less than 200 mg/dL is a "desirable" level and places the subject in a group at less risk for heart disease. Levels over 240 mg/dL may put a subject at almost twice the risk of heart disease as compared to someone with a level less than 200 mg/dL. High LDL cholesterol levels may be the best predictor of risk of heart disease.

The present methods can be used to determine whether a subject is likely to respond to HMGCR inhibitor therapy (e.g., statin therapy) with a clinically significant change in at least one of total cholesterol, LDL cholesterol, IDL cholesterol, and HDL cholesterol. For example, depending on the baseline cholesterol parameter, a reduction of total cholesterol, LDL cholesterol, and/or IDL cholesterol of at least 5%, at least 10%, at least 15%, at least 20% or more can be clinically relevant. Similarly, and again depending on the baseline parameter, an increase in HDL cholesterol of at least 5%, at least 10%, at least 15%, at least 20% or more can be clinically relevant. In general, patients within a population respond to a HMGCR inhibitor over a spectrum of response levels (see, e.g., FIG. 3C).

In one embodiment, the subject is one having, suspected of having, or at risk of a lipid disorder or a disorder associated with abnormally high levels of circulating lipids. Exemplary lipid disorders include from an elevated level of circulating total cholesterol, an elevated level of circulating LDL cholesterol, an elevated level of circulating IDL cholesterol, elevated ApoB/ApoA1, an elevated level of circulating free fatty acids, an elevated level of circulating triglycerides, and/or a low level of circulating HDL cholesterol. The lipid disorder can be associated with other disorders or syndromes, such as coronary artery disease, e.g., atherosclerosis.

Analysis of HMGCR Isoform Expression

In general, HMGCR isoform expression is detected in an appropriate cell obtained from the subject.

A biological sample containing a cell suitable for analysis of HMGCR isoform expression is obtained from a subject. Typical samples of interest include, but are not necessarily limited to, blood and blood cells (e.g., lymphocytes, and the like). Blood-derived cells such as lymphocytes are of particular interest due to, for example, the ease in which they can be obtained from a patient in a sufficient number for conducting an assay. Other suitable cells include monocytes, adipocytes, fibroblasts, muscle cells, mucosal epithelial cells and dermal cells.

Assessment of the effect of an HMGCR inhibitor is generally accomplished by exposing patient cells to a HMGCR inhibitor of interest (e.g., a statin), where exposure is usually for a period of time sufficient to provide for modulation of HMGCR isoform expression in a susceptible cell (e.g., for a time sufficient to provide for modulation of HMGCR isoform in a control cell susceptible to, for example, HMGCR(12-14) expression modulation by a HMGCR inhibitor such a simvastatin). In some embodiments it may be desirable to expose the cells to different concentrations of the HMGCR inhibitor, to provide for exposure for different time periods, to expose the cells to both a HMGCR inhibitor in combination with other drugs with which the patient is being treated or are proposed for treatment, and other such variables that will be readily apparent to the ordinarily skilled artisan. Usually, HMGCR isoform expression in the cells prior to exposure or HMGCR isoform expression in cells that are not exposed to the active HMGCR inhibitor serve as a control to provide a baseline of HMGCR isoform expression.

In other embodiments, the effect of HMGCR inhibitors is tested following exposure of patient cells in vivo. For example, a biological sample containing a cell suitable for analysis is obtained from a subject, and a statin drug is administered to a subject for a selected period of time, usually at least about 24-48 hours. After the selected period of drug administration, a second biological sample is obtained. The effect of the HMGCR inhibitor is assessed by comparing HMGCR isoform expression before (baseline, prior to treatment) and after HMGCR inhibitor therapy. This approach is less labor intensive than the approach described above, since it avoids the need to incubate patient cells in the presence of a HMGCR inhibitor. In addition, there is no need to isolate cells from the sample, as HMGCR expression can be assessed (e.g., using PCR-based methods) without the manipulation that might otherwise be required.

HMGCR isoform expression (e.g., expression of HMGCR12-14 expression, HMGCR12-13 expression, or both) can be accomplished by detection of a suitable gene product at the transcriptional (mRNA) or translational (protein) level. In an embodiment of particular interest, HMGCR isoform expression is assessed by detection of mRNA, usually through detection of cDNA generated from such mRNA.

The change in HMGCR isoform expression is then determined by comparing HMGCR isoform expression in a test cell (exposed to a HMGCR inhibitor) to a baseline of HMGCR isoform expression (e.g., HMGCR isoform expression in a control cell that was not exposed to the HMGCR inhibitor). The difference in HMGCR isoform expression in the test cell as compared to baseline is then used to assess the subject's likelihood to respond to therapy using the HMGCR inhibitor.

For example, a significant increase in HMGCR(12-14) expression over baseline HMGCR(12-14) expression indicates the subject has an increased likelihood of reduced response (insensitivity) to therapy using the HMGCR inhibitor, and has an increased likelihood that such therapy would not result in a desired reduction of total cholesterol and/or IDL cholesterol and/or desired reduction in LDL cholesterol. Where no significant increase in HMGCR(12-14) expression relative to baseline is observed, then the patient has a likelihood of a strong response to therapy using the HMGCR inhibitor, and a good likelihood of responding with satisfactory reductions of total cholesterol and/or LDL cholesterol and/or IDL cholesterol. Such a patient, however, if Caucasian, is likely to respond with a smaller increase in HDL cholesterol.

In general, HMGCR isoform expression levels can be expressed as either a fold change or as the ratio of $\Delta$HMGCR(12-14)/$\Delta$tHMGCR. Calculation of fold change and the ratio here are provided in more detail below. A fold change in HMGCR(12-14) expression of about 0.5, 0.6, 0.75, or 1.0 or less in the presence of drug as compared to the absence of drug indicates that the subject will be responsive to HMGCR inhibitor therapy, and will likely respond with decreased total cholesterol, decreased LDL cholesterol, and/or decreased IDL cholesterol and/or decreased ApoB. In general, a fold change in HMGCR(12-14) expression of at least about 1.25, 1.3, 1.35, 1.4, 1.45, 1.5, 1.75, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5 or more in the presence of drug as compared to the absence of drug indicates that the subject will likely be less responsive to HMGCR inhibitor therapy, and indicates an increased likelihood the patient will not respond to HMGCR inhibitor therapy with a clinically relevant modulation in at least one cholesterol parameter (e.g., decreased total cholesterol and/or decreased LDL cholesterol). However, such subjects will also be likely to respond to HMGCR inhibitor therapy with a greater increase in ApoA1. "Fold change" is generally calculated by dividing the HMGCR(12-14) expression in the presence of in the presence of the active drug by the HMGCR(12-

14) expression in the absence of the active drug, where each of the expression levels is normalized to a control gene having expression that is not significantly affected by a HMGCR inhibitor.

Where HMGCR(12-14) expression is assessed as the ratio of fold change in HMGCR(12-14) expression relative to fold change in total HMGCR expression, the calculation of the ratio value can be represented by the formula:

$$\frac{\Delta HMGCR \text{ isoform}}{\Delta tHMGCR}$$

where

ΔHMGCR isoform represents a change of the expression level of a selected HMGCR isoform (e.g., HMGCR(12-14) or HMGCR(12-13)) in the presence of a HMGCR inhibitor relative to a baseline expression level in the absence of the HMGCR inhibitor (in a control cell), and ΔtHMGCR (also referred to as Δtotal HMGCR) represents a change of expression level of total HMGCR in the presence of the HMGCR inhibitor relative to a baseline total HMGCR expression level in the absence of the HMGCR inhibitor (in a control cell). Total HMGCR can be detected by detection of a splice junction or other region common to all HMGCR isoforms of interest, e.g., detection of the 6-7 splice junction in HMGCR. The value calculated from the formula above is often referred to herein as a "ratio value", with "HMGCR(12-14) ratio value" referring to a value obtained by a calculation based on HMGCR(12-14) as the HMGCR isoform in the formula above and "HMGCR(12-13) ratio value" referring to a value obtained by a calculation based on HMGCR(12-14) as the HMGCR isoform in the formula above.

A ΔHMGCR(12-14)/ΔtHMGCR ratio value of 0.1, 0.2, 0.3, 0.4, 0.5, 0.6, 0.7, 0.8, 0.9 or 1.0 or lower indicates that the subject will be more responsive than average to HMGCR inhibitor therapy, and will likely respond with decreased total cholesterol, and/or decreased LDL cholesterol, and/or decreased IDL cholesterol and/or decreased ApoB. In general, a ratio value of greater than about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0, or more in the presence of drug as compared to the absence of drug indicates that the subject will likely be less responsive than average to HMGCR inhibitor therapy, and indicates an increased likelihood the patient will not respond to HMGCR inhibitor therapy with a clinically relevant modulation in at least one cholesterol parameter (e.g., decreased total cholesterol and/or decreased LDL cholesterol). However, such subjects will also be likely to respond to HMGCR inhibitor therapy with a greater increase in ApoA1.

Furthermore, the greater the fold increase in HMGCR(12-14) expression over baseline, or the higher the ratio of ΔHMGCR(12-14)/ΔtHMGCR, following exposure to a HMGCR inhibitor, the greater the expected level of resistance to HMGCR inhibitor therapy, i.e., the lower the expected reduction in total cholesterol and the lower the expected reduction LDL cholesterol, IDL cholesterol, apoB and apoA1. In addition, the greater the fold increase in HMGCR (12-14) expression over baseline, or the higher the ratio of ΔHMGCR(12-14)/ΔtHMGCR, following exposure to a HMGCR inhibitor the greater the expected increase in apoAI.

In the context of HDL cholesterol response, the fold change in HMGCR isoform expression is both race-dependent and dose-dependent. If the subject is African American and treated with the appropriate statin dose, the greater the fold increase in HMGCR(12-14) expression or HMGCR(12-13) expression over baseline following exposure to a HMGCR inhibitor, the greater the expected increase in HDL cholesterol. If the subject is Caucasian and treated with the appropriate statin dose, the lower the fold increase in HMGCR(12-14) expression or total HMGCR expression over baseline following exposure to a HMGCR inhibitor, the greater the expected increase in HDL cholesterol. As observed in the African American population in the Examples below, the relationship between HMGCR(12-14) expression and HMGCR(12-13) expression is affected by dose. At higher doses of a HMGCR inhibitor (e.g., statin), the greater the fold increase in HMGCR(12-14) expression and HMGCR (12-13) expression over baseline following exposure to a HMGCR inhibitor, the lower the expected increase in HDL cholesterol.

Stated differently, as shown in the Examples below, at a lower effective dose of a HMGCR inhibitor, a fold increase in HMGCR(12-14) expression or HMGCR(12-13) expression in a cell of a African American subject is indicative of a desirable HDL cholesterol response (i.e., a greater expected increase in HDL cholesterol). However, at a higher dose of a HMGCR inhibitor, a fold increase in HMGCR(12-14) or HMGCR(12-13) expression in a cell of a African American subject is indicative of a poor HDL cholesterol response (i.e., a lower expected increase in HDL cholesterol, which can include a decrease in HDL cholesterol). Thus, HMGCR isoform expression levels and correlation to predicted HDL cholesterol level response are affected by HMGCR inhibitor dose. The terms "effective dose" or "selected dose" as used in the context of modulation of HDL cholesterol levels in a subject and/or determining a dose of HMGCR inhibitor that provides a clinically significant HDL cholesterol response, is a dose that provides for a HMGCR isoform expression profile that is correlated with an expected increase in the subject, taking into account the ethnicity of the subject.

Algorithms for Assessing Likelihood of Clinically Relevant Response to HMGCR Inhibitor in a Subject In general, the inventors have found that the greater the HMGCR(12-14) expression in the presence of a HMGCR inhibitor (as compared to baseline HMGCR(12-14) expression in the absence of the drug), the smaller the decrease in LDL cholesterol, the smaller the decrease in IDL cholesterol, and the smaller the decrease in total cholesterol can be expected in the subject. In addition, the greater the HMGCR (12-14) expression in the presence of a HMGCR inhibitor (as compared to baseline HMGCR(12-14) expression in the absence of the drug), the greater the apoA1 increase that can be expected in the subject. In African Americans, the greater the HMGCR(12-13) expression level and/or the greater the HMGCR(12-14) expression level in the presence of a HMGCR inhibitor (as compared to baseline expression in the absence of the drug), the greater the expected HDL cholesterol increase in the subject upon administration of a selected dose. However, if the dose of the HMGCR inhibitor is too high, then elevated HMGCR(12-14) or HMGCR(12-13) expression levels are no longer associated with improved HDL cholesterol responses in the subject. In Caucasians, the greater the HMGCR(12-14) expression, HMGCR(12-13) expression, and/or total HMGCR expression, the lower the expected HDL cholesterol increase in the subject. Thus in Caucasians, a desirable HDL cholesterol response is indicated by the absence of an induction, or a reduction in, HMGCR(12-14) expression, HMGCR(12-13) expression, or total HMGCR expression.

The relationships between HMGCR isoform expression and response in a subject in total cholesterol, LDL cholesterol, IDL cholesterol, and HDL cholesterol can be expressed in one or more algorithms to facilitate prediction of response to a HMGCR inhibitor. In one embodiment, the methods of the invention relating to assessment of change in HMGCR (12-14) expression in response to a HMGCR inhibitor (e.g., statin) can be used to generate data, which in turn can be used to provide an algorithm for assessing likelihood of a response to a HMGCR inhibitor therapy, as well as the magnitude of the response that is likely to be observed upon HMGCR inhibitor therapy in a subject.

For example, as described in more detail in the Examples below, data generated using the methods of the invention to assess changes in HMGCR(12-14) and unspliced HMGCR expression in patient cells (n=169) following exposure to a HMGCR inhibitor (e.g., simvastatin) were compiled and analyzed to provide the following exemplary algorithms for determining change in total cholesterol, IDL cholesterol, LDL cholesterol, and HDL cholesterol. The following exemplary algorithms can be used to determine a predicted change in total cholesterol, and LDL cholesterol:

Predicted change in total cholesterol (mg/dl)=−46.1+ (10.8)(12-14 fold change)

Predicted Change in LDL-cholesterol in mg/dl=− 44.0+(9.2)(12-14 fold change)

Predicted change in total cholesterol (mg/dl)=−76.7+ (41.7)($\Delta$12-14/$\Delta$tHMGCR ratio)

Predicted change in IDL-cholesterol (mg/dl)=−4.8+ (5.2)($\Delta$12-14/$\Delta$tHMGCR ratio)

Predicted change in LDL-cholesterol in mg/dl=−70.3+ (35.6)($\Delta$12-14/$\Delta$tHMGCR ratio)

The following exemplary algorithms can be used to determine a predicted change in HDL cholesterol:
In African Americans:

Change in HDL-cholesterol in mg/dl=−5.70+(4.45) (12-14 fold change)

Change in HDL-cholesterol in mg/dl=−5.72+(5.7)(12- 13 fold change)

In Caucasian Americans:

Change in HDL-cholesterol in mg/dl=12.85+(−6.22) (12-14 fold change)

Change in HDL-cholesterol in mg/dl=6.92+(−2.0)(12- 13 fold change)

"12-14 fold change" indicated above is a numerical value indicating the change in HMGCR(12-14) expression following exposure of a patient's cells to HMGCR inhibitor (where baseline is HMGCR(12-14) expression prior to drug exposure). The "ratio" is a ratio of expression levels, which is calculated as a fold change ("$\Delta$") in a selected HMGCR isoform expression level divided by a fold change in total HMGCR expression (represented by "tHMGCR" above) as described above.

These algorithms above can be executed to provide guidance as to an expected range of responses to administration of a HMGCR inhibitor based on an observed change in HMGCR (12-14) in the presence of the drug as compared to a baseline expression in the absence of the drug. For example, the predicted absolute change in total cholesterol based on different increases in expression of HMGCR(12-14) is summarized in the table below (where "fold change" is relative to a baseline expression in the absence of the drug, and "12-14/6-7 ratio" indicates the fold change of 12-14 divided by the fold change of tHMGCR (e.g., as assessed by detection of the 6-7 splice junction):

These algorithms can be used to qualitatively to predict whether a subject will respond to a HMGCR inhibitor therapy, as well as to predict quantitatively what magnitude response is likely to occur in the subject upon HMGCR inhibitor therapy. Examples of how such algorithms can be used as set out in detail in the Examples below.

| Total Cholesterol - predicted absolute change (mg/dl) with HMGCR inhibitor treatment | | | |
|---|---|---|---|
| | 95% confidence interval | | |
| 12-14/6-7 ratio | low | average | High |
| 0.5 | −100 | −90 | −75 |
| 1.0 | −62 | −60 | −58 |
| 1.5 | −50 | −40 | −30 |

| Total Cholesterol - predicted absolute change (mg/dl) with HMGCR inhibitor treatment | | | |
|---|---|---|---|
| 12-14 fold | 95% confidence interval | | |
| change | low | average | High |
| 0.5 | −82 | −70 | −60 |
| 1.5 | −65 | −60 | −55 |
| 2.5 | −59 | −50 | −40 |

| IDL Cholesterol - predicted absolute change (mg/dl) with statin treatment | | | |
|---|---|---|---|
| | 95% confidence interval | | |
| 12-14/6-7 ratio | low | average | High |
| 0.5 | −15 | −14 | −10 |
| 1.0 | −11 | −10 | −9 |
| 1.5 | −10 | −7.5 | −6 |

In another example, the predicted absolute change in LDL cholesterol based on different increases in expression of HMGCR(12-14) is summarized in the table below (where "fold change" is relative to a baseline expression in the absence of the drug, and "12-14/6-7 ratio" indicates the fold change of 12-14 divided by the fold change of 6-7):

| LDL-Cholesterol - predicted absolute change (mg/dl) with statin treatment | | | |
|---|---|---|---|
| | 95% confidence interval | | |
| 12-14/6-7 | low | Average | high |
| 0.5 | −90 | −80 | −70 |
| 1.0 | −65 | −58 | −55 |
| 1.5 | −50 | −45 | −35 |

| LDL Cholesterol - predicted absolute change (mg/dl) with HMGCR inhibitor treatment | | | |
|---|---|---|---|
| 12-14 fold | 95% confidence interval | | |
| change | low | average | High |
| 0.5 | −78 | −68 | −58 |
| 1.5 | −60 | −58 | −55 |
| 2.5 | −55 | −45 | −35 |

| HDL-Cholesterol - predicted absolute change (mg/dl) with statin treatment in African Americans | | | |
|---|---|---|---|
| 12-14 fold | 95% confidence interval | | |
| change | low | average | high |
| 1.0 | −4 | −1 | +0.5 |
| 1.5 | −1 | 0 | +1.0 |
| 2.0 | 0 | +2.0 | +5.0 |

| HDL-Cholesterol - predicted absolute change (mg/dl) with statin treatment in Caucasian Americans | | | |
|---|---|---|---|
| 12-14 fold | 95% confidence interval | | |
| change | low | average | high |
| 1.0 | +1 | +3 | +6.0 |
| 1.5 | 0 | +2 | +4.0 |
| 2.0 | −5 | −1 | +2.0 |

| HDL-Cholesterol - predicted absolute change (mg/dl) with statin treatment in African Americans | | | |
|---|---|---|---|
| 12-13 fold | 95% confidence interval | | |
| change | low | average | high |
| 1.0 | −5 | −3 | 0 |
| 1.5 | −1 | 0 | +1.0 |
| 2.0 | 0 | +2.0 | +5.0 |

| HDL-Cholesterol - predicted absolute change (mg/dl) with statin treatment in Caucasian Americans | | | |
|---|---|---|---|
| 12-13 fold | 95% confidence interval | | |
| change | low | average | high |
| 1.0 | 0 | +3 | +6.0 |
| 1.5 | 0 | +2 | +5.0 |
| 2.0 | −1 | −1 | +4.0 |

Manual and Computer-Assisted Methods and Products Computer Program

The values from the HMGCR(12-14) expression assays described above can be calculated and stored manually, e.g., on a patient record. Alternatively, the above-described steps can be completely or partially performed by a computer program product. The present invention thus provides a computer program product including a computer readable storage medium having a computer program stored on it. The program can, when read by a computer, executes relevant calculations based on values obtained from analysis of one or more biological sample from an individual (e.g., of changes in values associated with HMGCR(12-14) expression in cells following exposure to a HMGCR inhibitor), conversion of values from assays to a prediction regarding response to HMGCR inhibitor therapy, conversion of values from assays to predict a change in one or more of total cholesterol, LDL cholesterol, IDL cholesterol, or HDL cholesterol, and the like) The computer program product has stored therein a computer program for performing the calculation.

Figure 11:
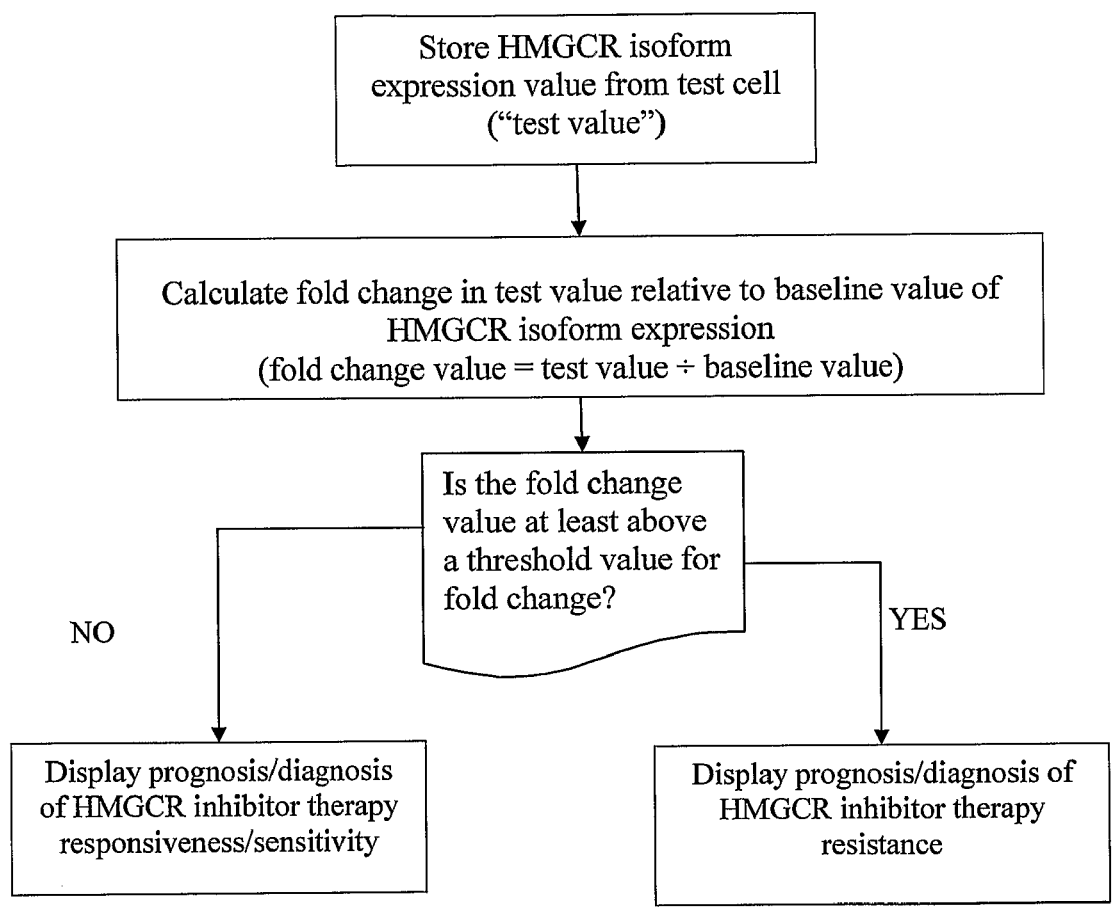
FIGS. 11 and 12 are schematics showing exemplary computer-based embodiments of the methods of the invention.

The computer program product can also analyze the data, as depicted in FIG. 11, wherein a value for HMGCR isoform expression (e.g., HMGCR(12-14)) in a test cell assay result is determined, the computer program product calculates the change value in HMGCR isoform expression relative to a baseline (e.g., a fold change value or ratio value, where the fold change value and ratio value are determined as described above for fold change and ratio calculations, respectively), and then determines whether the change value is above or below a selected threshold value, where the threshold value is a value indicative of a significant change (e.g., significant fold change value or significant HMGCR isoform/total HMGCR ("tHMGCR") ratio value) indicative of responsiveness or resistance to HMGCR inhibitor therapy.

The threshold value is selected according to, for example, the values for fold change or HMGCR isoform/total HMGCR ratios discussed herein as appropriate. For example, a threshold value of 1 can be useful, where a fold change value equal to or less than one indicates the HMGCR(12-14) expression was not elevated in the presence of drug or actually decreased in the presence of drug. Similarly, where the threshold value is 1, a fold change value greater than 1 indicates HMGCR (112-14) expression was elevated in the presence of drug. In another example, a threshold value of 1.0 can be useful, where a ratio value equal to or less than one indicates the HMGCR (12-14) expression was not elevated in the presence of drug or actually decreased in the presence of drug compared to the total HMGCR gene expression. Similarly, where the threshold value is 1 a ratio value greater than one indicates HMGCR (12-14) expression was elevated in the presence of drug more than total HMGCR gene expression. Selection of a higher value for a threshold value provides for a more conservative prediction of response (e.g., a greater specific induction of HMGCR(12-14) relative to total HMGCR gene expression is required to predict likelihood of resistance to HMGCR inhibitor therapy or to predict likelihood of a response that is clinically unsatisfactory for a patient). The ordinarily skilled artisan will appreciate that the threshold value can be altered to reflect the spectrum of responsiveness.

Figure 12:
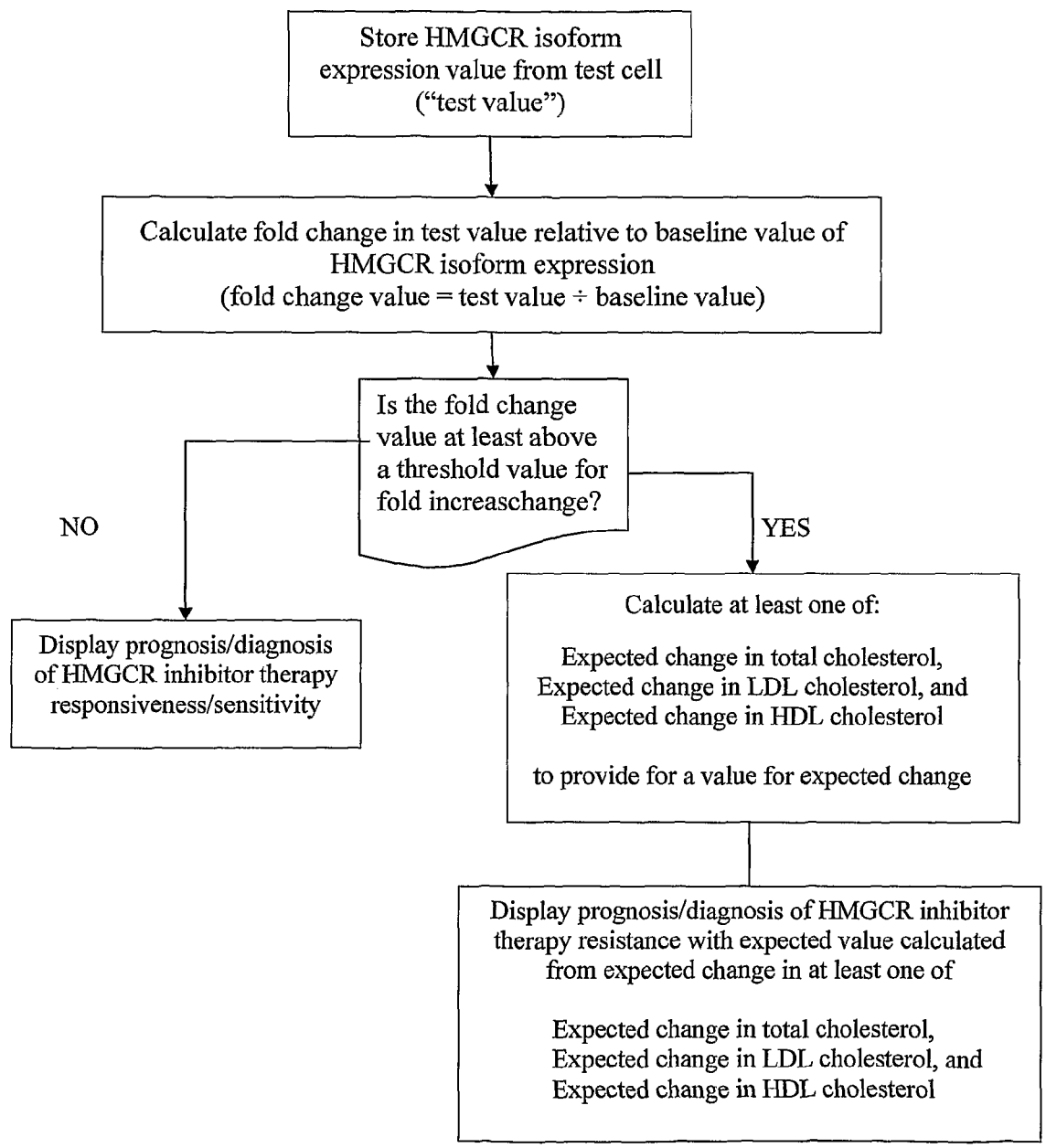

Based on comparison to the threshold value, the computer program product assesses the magnitude of the expected response to HMGCR inhibitor therapy, and displays a result to the user. For example, where a result is not clinically desirable for the subject, the result "resistant" as exemplified in FIG. 12 or "less responsive" may be displayed. The values for analysis by the computer program can be input into the program manually, or the values can be obtained from an assay device can be transferred directly into the program so as to avoid manual input.

As illustrated in FIG. 10, the computer program can also be designed to provide for calculation of an expected change in total cholesterol, LDL cholesterol, IDL cholesterol, and/or HDL cholesterol. In this embodiment, the algorithm used is based on data obtained from assessment of HMGCR isoform expression in a population of cells following HMGCR inhibitor exposure, such as the algorithms exemplified above and in the Examples below. In this embodiment, the program can provide for display of a prognosis/diagnosis of HMGCR inhibitor therapy resistance, which display can be accompanied by an expected change in total cholesterol, HDL cholesterol, IDL cholesterol, or LDL cholesterol, as appropriate.

In some embodiments, the computer program is designed to store values for 1, 2, 3, 4, or more different assays associated with different HMGCR inhibitors. Optionally, the program can store multiple values from multiple different assays and/or from the same assays conducted at different times, under different conditions, and the like.

Systems and Apparatus

In a related embodiment, the invention provides a system for executing the program described above, which system generally includes: a) a central computing environment; b) an input device, operatively connected to the computing environment, to receive assay data, wherein the assay data can include, for example, data from assays to assess HMGCR(12-14) expression, and optionally expression of other HMGCR isoforms (e.g., HMGCR(12-13)), from an assay using a biological sample from the patient as described in detail above; c) an output device, connected to the computing environment, to provide information to a user (e.g., medical personnel); and d) at least one algorithm executed by the central computing environment (e.g., a processor), where the algorithm is executed based on the data received by the input device, wherein the algorithms can provide for calculation of i) a fold change value for HMGCR isoform expression; ii) a likelihood of response or resistance to a HMGCR inhibitor therapy (by comparison of the fold change value to a threshold value), and, optionally, iii) an expected change in at least one of total cholesterol, LDL cholesterol, IDL cholesterol or HDL cholesterol.

The instant invention further provides a portable apparatus having a computer readable medium (e.g., a processor) that stores data, calculates values using algorithm described above, and provides an assessment of responsiveness or resistance to a HMGCR inhibitor therapy based on the calculation. In some embodiments, a subject apparatus (e.g., a portable apparatus) comprises: a) a device for receiving and storing patient data as described above, including assay values, calculation results, and information relating to the HMGCR inhibitor tested, patient information, and the like; b) a data output device; and c) at least one algorithm stored within the computer program product within the apparatus, which algorithm, for example, assesses a prognosis or diagnosis of responsiveness or resistance to a HMGCR inhibitor therapy as described above, which information is transmitted to the data output device, where the output device displays the information (e.g., "HMGCR inhibitor sensitive, "HMGCR inhibitor responsive, "HMGCR inhibitor resistant", and the like) to a user.

The data input device (also referred to as an operator input device) may be, e.g., a keyboard or keypad, a mouse, and the like. The processor has access to a memory, which may be any suitable device in which the processor can store and retrieve data, such as magnetic, optical, or solid state storage devices (including magnetic or optical disks or tape or RAM, or any other suitable device). The processor can include a general purpose digital microprocessor (such as is typically used in a programmable computer) suitably programmed to execute an algorithm as described above, or any hardware or software combination which will perform the required functions.

In some embodiments, the portable apparatus comprises: a) a device for determining a HMGCR isoform expression assay value (e.g., a HMGCR(12-14) expression assay value) from a biological sample; b) a device for communicating (e.g., transmitting) the determined value to the receiving and storage device; c) a data output device; and d) an algorithm stored within a computer program product within the apparatus, which algorithm is executed to, for example, determine a fold change value, determine whether a fold change value is above or below a threshold value, calculate an expected value of change in one or more of total cholesterol, LDL cholesterol, IDL cholesterol, and HDL cholesterol. The result is transmitted to the data output device, where the output device displays the assessment to a user, which assessment can include a prognosis/diagnosis of resistance or sensitivity, and optionally include a value of expected change in one or more of total cholesterol, LDL cholesterol, IDL cholesterol, and HDL cholesterol.

In general, a subject apparatus will include a computer readable medium including the programming described above. The computer program can be recorded on computer readable media, e.g., any medium that can be read and accessed directly or indirectly by a computer. Such media include, but are not limited to: magnetic tape; optical storage such as compact disc-read only memory (CD-ROM) and digital versatile disk (DVD); electrical storage media such as random access memory (RAM) and read-only memory (ROM); and hybrids of these categories such as magnetic/optical storage media. One of skill in the art can readily appreciate how any suitable computer readable media can be used to create a manufacture that includes a recording of the present programming/algorithms for carrying out the above-described methodology. In certain embodiments, the programming is further characterized in that it provides a user interface, where the user interface presents to a user the option of selecting among one or more different, including multiple different, criteria, e.g., age of individual, etc. The instructions may include installation or setup directions. The instructions may include directions for use of the invention.

In addition, a subject apparatus will typically include instructions for using the apparatus to carry out a method of the invention. The instructions of the above-described apparatus are generally recorded on a suitable recording medium. For example, the instructions may be printed on a substrate, such as paper or plastic, etc. As such, the instructions may be present in the apparatus as a package insert, or components thereof (i.e. associated with the packaging or sub packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the apparatus, but means for obtaining the instructions from a remote source, e.g. via the Internet, are provided. An example of this embodiment is an apparatus that includes a web address where the instructions can be viewed and/or from which the instructions can be downloaded. Conversely, means may be provided for obtaining the subject programming from a remote source, such as by providing a web address. Still further, the apparatus may be one in which both the instructions and software are obtained or downloaded from a remote source, as in the Internet or World Wide Web. Some form of access security or identification protocol may be used to limit access to those entitled to use the subject invention. As with the instructions, the means for obtaining the instructions and/or programming is generally recorded on a suitable recording medium.

Rational Therapy Based on Assessment of HMGCR Expression

The methods of the invention can also be applied to facilitate the selection of a therapy for conditions associated with elevated total cholesterol and/or elevated LDL cholesterol. For example, administration of an HMGCR inhibitor such as a statin can be beneficial in modulating cholesterol levels. However, providing information to the clinician regarding the propensity of an individual to respond to administration of an HMGCR inhibitor (e.g., a statin) by modulation of expression of a HMGCR isoform (e.g., the HMGCR(12-14) isoform) is of value in selecting a therapeutic regimen from which the individual will benefit most.

The methods of the invention relating to rational therapy can be applied to any subject for whom a HMGCR inhibitor therapy is proposed, or any subject who is undergoing HMGCR inhibitor therapy. For example, the subject can be one for whom a HMGCR inhibitor therapy is proposed due to presentation with one or more risk factors for a coronary artery disease, particularly a subject having an elevated serum total cholesterol level and/or elevated serum LDL cholesterol level.

The methods of the invention can be applied to assess a HMGCR inhibitor therapy in a subject who has received or is receiving therapy. For example, the patient cells can be exposed to drug in vivo as described above, and HMGCR expression assessed. Based on this analysis, the clinician or other health profession can assess whether the selected regimen should be continued or modified based on the modulation of the HMGCR isoform expression levels (e.g., HMGCR(12-14) isoform expression levels). In this aspect, the invention is particularly advantageous in that it allows for therapy to be initiated and assessed relatively soon afterward. For example, the methods of the invention allow for assessment of efficacy of a therapeutic regimen within a few days or weeks. In contrast, conventional methods of assessing HMGCR inhibitor therapy normally involves assessing cholesterol levels several months (e.g., about 3 months) after therapy has been initiated.

The invention can also be used not only as an aid in selection of HMGCR inhibitor therapy, but also in following or modifying a HMGCR inhibitor therapy. For example, the subject can be one who is undergoing HMGCR inhibitor therapy, and assessment of response is desired. For example, where the subject is undergoing HMGCR inhibitor therapy, but is not responding to a desired degree, the methods of the invention can be used to determine whether adjusting HMGCR inhibitor therapy dosage (e.g., amount and/or frequency of dosing) would be beneficial, or whether the subject is not likely to respond as desired, and therapy should be changed entirely (e.g., by changing to a drug that lowers cholesterol by a different mechanism).

Further, assessment of an HMGCR isoform expression profile can be used to guide modification of a HMGCR inhibitor treatment regimen, e.g., modifying (increasing or decreasing) the dosing frequency of the active agent administered; administering one or more additional active agents; modifying (increasing or decreasing) the amount of active agent administered; and administering a different active agent from the active agent, e.g., discontinuing administration of the active agent. Thus, the invention can provide methods for tailoring therapy according to an individual's propensity for responsiveness to a HMGCR inhibitor therapy.

In some embodiments, modifying a dosing regimen comprises increasing the dosing frequency, e.g., increasing administering the active agent from once per week to twice per week, to three times per week, to daily, or to twice daily. Thus, e.g., in some embodiments, a method comprising administering an active agent at a frequency of once per week is modified such that the active agent is administered twice per week, three times per week, daily, or twice daily. In some embodiments, modifying a dosing regimen comprises administering at least a second active agent, and, in some embodiments comprises discontinuing administration of the first active agent.

In general, assessment of a HMGCR(12-14) expression level can provide guidance as to the dose or dosage to be administered to a subject. For example, if a subject responds to administration of a HMGCR inhibitor without substantial or significant elevation of HMGCR(12-14) expression levels, then it may be possible to modify the patient's dosage regimen so as to reduce the amount of HMGCR inhibitor administered (e.g., by reducing the amount, frequency, or both). As discovered by the inventors, the magnitude of the HMGCR(12-14) expression level corresponds to an increased "resistance" to HMGCR inhibitor therapy. Thus a relatively lower HMGCR(12-14) expression level is indicative of an increased responsiveness to the HMGCR inhibitor. Where HMGCR(12-14) expression levels indicate the subject is likely to respond to the HMGCR inhibitor with a lower reduction in LDL cholesterol levels or IDL cholesterol levels or total cholesterol levels or apoB levels, such subjects are candidates for treatment with a combination therapy involving administration of the HMGCR inhibitor with an agent that decreases HMGCR(12-14) expression levels.

The methods of the invention thus allow a clinician or physician to target prophylactic or therapeutic HMGCR inhibitor treatments to patients who will most benefit from the treatment and to avoid treatment of patients who will not receive sufficient or significant benefit from therapy.

Clinical Trial Design

The invention further provides for methods of grouping or "stratifying" subjects according to an HMGCR isoform expression profile in cells of the patient in response to a known or candidate HMGCR inhibitor therapy. The HMGCR inhibitor-responsive HMGCR isoform expression profile is determined for each subject in a pool of subjects or potential subjects for a clinical trial, and the subjects classified accordingly. For example, subjects which, as determined by the methods described herein, respond to HMGCR inhibitor by increased HMGCR(12-14) expression may be excluded or included from a trial of a candidate HMGCR inhibitor, or may be separately categorized so that such subjects can be followed independently of other subjects. Subjects can also be classified according to a fold change in HMGCR(12-14) expression in response to a HMGCR inhibitor or candidate HMGCR inhibitor.

Categorization of subjects according to HMGCR inhibitor-induced HMGCR isoform expression can facilitate more accurate assessment of a candidate therapy for which the trail is designed. The HMGCR isoform expression profile classification of a subject can also be used in assessing the efficacy of a candidate cholesterol modulating therapy in a heterogeneous subject population. Thus, comparison of an individual's HMGCR isoform expression phenotype relative to that of others in the subject population facilitates analysis of results and provides better support for analysis of the therapeutic regimens that are efficacious for a particular subject or subject population.

In addition, HMGCR inhibitor-induced HMGCR isoform expression profiles of a subject can also be used to identify a patient population for assessment of candidate therapies for mitigation of the adverse effect of increased HMGCR(12-14) expression upon HMGCR inhibitor therapy. For example, subjects who are resistant to a HMGCR inhibitor therapy due to increased HMGCR(12-14) expression can be identified and separated from those subjects who do not exhibit such a HMGCR inhibitor-resistance phenotype. The subjects having increased HMGCR(12-14) expression in response to a HMGCR inhibitor can then be included in clinical trial to assess the efficacy of a candidate therapy for modulation of cholesterol levels in such a resistant population, e.g., a therapy that acts to counteract the effects of normally increased HMGCR(12-14) levels in response to inhibition of HMGCR activity.

In addition, the ability to target individuals expected to show the most clinical benefit, based on their HMGCR isoform expression profile can facilitate: 1) the repositioning of drugs available on the market; 2) the rescue of drug candidates whose clinical development has been discontinued as a result of limited efficacy (which may result from inclusion of resistant subjects in the clinical trial); and 3) an accelerated and less costly development for candidate therapeutics and more optimal drug labeling (e.g. since measuring the effect of various doses of an agent on patients with a particular expression profile is useful for optimizing effective dose).

Methods of Screening to Identify Drugs for Modulation of Serum Cholesterol

The present invention also provides for methods to identify agents that, either alone or in combination with a HMGCR inhibitor (statin), provide for inhibition of HMGCR while at the same time providing a HMGCR(12-14) expression profile that is favorable for a response in lowering of total cholesterol, lowering LDL cholesterol, lowering IDL cholesterol and/or increasing HDL cholesterol. The screening methods will typically be assays which provide for qualitative/quantitative measurements of HMGCR(12-14) expression (e.g., by assessing HMGCR(12-14) expression at the transcriptional, translational, or functional levels) in the presence of a particular candidate agent. For example, the assay could be an assay which measures the relative levels of HMGCR(12-14) expression in the absence and presence of a candidate HMGCR inhibitor agent. In some embodiments, the candidate agent is tested for the ability to reduce HMGCR(12-14) expression when in the presence of a HMGCR inhibitor, such as a statin.

Where identification of drugs that facilitate an increase HDL cholesterol in African Americans is of interest, the screening methods can involve assessing a level of HMGCR (12-14) isoform expression or HMGCR(12-13) isoform expression. In this context if the candidate agent facilitates an increase in HMGCR(12-14) isoform expression or a HMGCR(12-13) isoform expression, then the agent is identified as one that can facilitate an increase in HDL cholesterol in an African American subject.

Where identification of drugs that facilitate an increase HDL cholesterol in Caucasian Americans is of interest, the screening methods can involve assessing a level of HMGCR (12-14) isoform expression, HMGCR(12-13) isoform expression, or total HMGCR expression. In this context if the candidate agent facilitates a decrease or no increase (e.g., does not cause an increase) in HMGCR(12-14) isoform expression, HMGCR(12-13) isoform expression, or total HMGCR expression, then the agent is identified as one that can facilitate an increase in HDL cholesterol and/or that will not cause a decrease in HDL cholesterol in an Caucasian American subject.

The screening methods can assess the correlation between dose and HMGCR expression profile, so as to aid not only in identification of an agent having an activity of interest, but also so as to take into account any dose effect the agent may have upon HMGCR expression. For example, as set out in the Examples below, the correlation between HDL cholesterol and HMGCR isoform expression levels was found to be dose-dependent. Assessing the effect of dose upon expression profile can be accomplished by, for example, conducting multiple assays using increasing doses of the candidate agent.

The screening method may be an in vitro or in vivo format, where both formats are readily developed by those of skill in the art. Usually the assay is an in vitro assay using isolated cells, particularly cells isolated from a patient who has failed a HMGCR inhibitor therapy (e.g., who did not respond to statin therapy by lowering total cholesterol, lowering LDL cholesterol, or increasing HDL cholesterol). Where the cells are patient cells, the cells are normally obtained from a convenient tissue, e.g., blood, and may be primary cells or cell lines derived from primary cells. For example, lymphocytes are useful in the screening assays of the invention. Other suitable cells for in vitro candidate agent screening assays include lymphocytes, monocytes, adipocytes, myocytes (muscle cells), fibroblasts and epithelial cells (e.g., mucosal epithelial cells, dermal cells), and other cells as discussed herein.

In other embodiments, the screen is conducted in vivo, e.g., in a non-human animal model, and HMGCR isoform expression is assessed after exposure of the animal model to the candidate agent, which may be administered alone or in combination with a known HMGCR inhibitor. Following administration, HMGCR isoform expression is assessed in appropriate cells obtained from the animal. Exemplary animals which may be suitable for use in such in vivo assays, and which may also serve as a suitable source of cells for in vitro assay screens, may include rodents (e.g., hamsters, mice, rats), rabbits, and pigs.

The screening methods can optionally include a step of detecting HMGCR activity of a candidate agent, e.g., to identify a candidate agent that has activity as HMGCR inhibitor and/or, where the candidate agent is screened for use in a combination therapy with a HMGCR inhibitor, to assess whether the combination of candidate agent and HMGCR inhibitor affects the activity of the HMGCR inhibitor. Methods for detecting HMGCR activity are well known in the art. See, e.g., Edwards et al. *J. Lipid Res.* (1979) 20:40-46.

Candidate Agents

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Methods of Screening

Typically, an assay to identify an agent of interest will involve contacting a candidate agent to be tested with a cell comprising a nucleic acid encoding a HMGCR(12-14) preferably under control of its native promoter and other relevant regulatory sequences. The cell can contain an endogenous HMGCR gene comprising a genomic HMGCR nucleic acid which can be alternatively spliced to provide for an HMGCR isoform, e.g., an HMGCR(12-14) isoform. Alternatively the cell used in the assay is a recombinant cell containing an expression construct comprising a genomic HMGCR nucleic acid, preferably under control of its native promoter.

The HMGCR(12-14)-encoding sequence can optionally be operably linked to a reporter gene to facilitate detection of HMGCR(12-14) expression (e.g., β-galactosidase, chloramphenicol acetyl transferase, a fluorescent protein (e.g., GFP, luciferase, and the like), or other gene that can be easily assayed for expression).

In general the screening method involves contacting a cell that is capable of expressing the HMGCR isoform of interest with an agent to be tested, forming a test sample, and, after a suitable time, assessing the effect of the agent on HMGCR isoform expression. A control sample is normally the same cell without the candidate agent added, and, where the ability of the candidate agent to modulate HMGCR isoform expression in the presence of a known HMGCR inhibitor is to be assessed, the control sample further includes the HMGCR inhibitor. That is, where the agent is to be tested for modulation of HMGCR isoform expression in the presence of a known HMGCR inhibitor (e.g., a known statin), HMGCR isoform expression is evaluated in the presence of the HMGCR inhibitor alone and in the presence of both the HMGCR inhibitor and the candidate agent.

HMGCR isoform expression levels are measured in both the test sample and the control sample. Methods of assessing HMGCR isoform mRNA levels are known in the art, several of which have been described above, and any of these methods can be used in the methods of the present invention to identify an agent which modulates levels of a HMGCR isoform mRNA in a cell, including, but not limited to, a polymerase chain reaction (PCR), such as a PCR employing detectably labeled oligonucleotide primers, and any of a variety of hybridization assays. Similarly, HMGCR isoform polypeptide levels can be measured using any standard method, several of which have been described herein, including, but not limited to, an immunoassay such as enzyme-linked immunosorbent assay (ELISA), for example an ELISA employing a detectably labeled antibody specific for a HMGCR isoform polypeptide.

A comparison of HMGCR isoform expression levels is made between HMGCR isoform expression levels in the test sample and the control sample, e.g., using conventional assays. A suitable period of time for contacting the agent with the cell can be determined empirically, and is generally a time sufficient to allow entry of the agent into the cell and to allow the agent to have a measurable effect on HMGCR isoform expression as assessed by mRNA and/or polypeptide levels. Generally, a suitable time is between 10 minutes and 24 hours, or from about 1 hour to about 8 hours.

Candidate agents that provide for modulation of HMGCR isoform expression to provide a desired HMGCR isoform expression profile (e.g., inhibition of HMGCR(12-14) isoform expression to identify agents that can facilitate an decrease in total cholesterol, LDL cholesterol, and/or IDL cholesterol) generally provide for a change in a HMGCR isoform expression level of at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more as compared to a control (e.g., HMGCR(12-14) expression in the absence of the candidate agent (e.g., HMGCR inhibitor without candidate agent)) is an indication that the agent modulates HMGCR isoform expression (e.g., if the modulation is a decrease in HMGCR(12-14) levels, the agent is an inhibitor of HMGCR(12-14) expression).

It will be understood that, where desired, the effects of candidate agents on HMGCR(12-13) can be assessed as described above for HMGCR(12-14). Such assays may be desirable in, for example, screening of agents to identify those that can be effective in enhancing HDL cholesterol levels in African Americans and Caucasian Americans.

Exemplary Drugs that can be Identified Using the Screening Methods of the Invention As discussed above, the screening methods of the invention can be used to identify agents that, either alone or in combination with a conventional HMGCR inhibitor (statin), inhibit HMGCR activity while at the same time providing a HMGCR (12-14) expression profile that is favorable for a response in lowering of total cholesterol, lowering IDL cholesterol, lowering LDL cholesterol and lowering apoB.

In general, the drug screening methods described herein can facilitate identification of at least two classes of drugs. First, the screening methods can be used to identify drugs that increase statin efficacy by altering regulation of the HMGCR gene (specifically alternative splicing), as well as drugs that alter HMGCR inhibitor responsiveness by preventing or limiting overall HMGCR up-regulation. Assays to identify such drugs can be performed with candidate agents in the presence or absence of a HMGCR inhibitor, where drugs that alter HMGCR splicing regulation in the presence of a HMGCR inhibitor are suitable for use in combination therapy. For example, agents that provide for decreased HMGCR(12-14) expression in the presence of a HMGCR inhibitor are particularly useful in treatment of subjects who respond to the HMGCR inhibitor with elevated HMGCR(12-14) expression.

A second general class of drug that can be identified using the methods of the invention are agents that alter regulation of HMGCR splicing (e.g., shift the splicing machinery away from the HMGCR(12-14) expression product and/or toward the unspliced HMGCR expression product). Such agents could provide for lower total cholesterol, lower IDL cholesterol, lower LDL cholesterol, and/or increased HDL cholesterol independent of statin treatment. For example, such agents may act upon the splicing machinery for the HMGCR gene, rather than upon the HMGCR polypeptide per se. In this way, the screening methods of the invention can provide for agents that are directed to targets upstream of HMGCR activity, e.g., by targeting the splicing machinery, preferably HMGCR-specific splicing machinery, that leads to the expression of HMGCR gene products.

Agents suitable for us in combination with a HMGCR inhibitor (statin) would be of particular interest as such drugs could provide several advantages over existing therapies. For example, such combination therapy agents that provide for reduced HMGCR(12-14) expression could provide an improved response in subjects by reducing the level of statin-resistant expression product generated from the HMGCR gene. Further such combination therapy agents could improve efficacy of an HMGCR inhibitor such that the amount of drug needed to provide a desired effect could be reduced. Indeed, in patients who do not respond in LDL cholesterol reduction to a clinically significant level or to a level that provides for a therapeutic benefit, co-administration of the combination therapy agent with a HMGCR inhibitor could provide for an improved outcome.

In still another aspect, the screening methods of the invention can be used to identify agents that reduce HMGCR activity (and hence lower LDL) by increasing splicing to form HMGCR(12-14) in the absence of statin. Based on the loss of the catalytic site in the HMGCR(12-14) isoform, it is be expected to be a less active form, as suggested by human peroxisomal deficiency.

Kits

Kits for use in connection with the subject invention are also provided. Any combination of the above-described assay reagents, including the primers, probes, solid support with bound probes, as well as other detection reagents, can be provided in kits, with suitable instructions and other necessary reagents, in order to conduct the assays as described above. The kit will normally contain in separate containers the combination of primers and probes (either already bound to a solid matrix or separate with reagents for binding them to the matrix), control formulations (positive and/or negative), labeled reagents when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular assay used, other packaged reagents and materials (i.e. wash buffers and the like). Standard assays, such as those described above, can be conducted using these kits.

The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In general, kits of the invention include at least one primer, usually at least two primers (a 5' and a 3' primer), usually at least two primers and a probe, as described above. Kits may also contain instructions for using the kit to detect a HMGCR isoform (e.g., HMGCR(12-14) isoform and/or HMGCR(12-13) isoform) in a sample using the methods described above, including the above discussed PCR methods. The kit may further include a means for assessing the implications of a change in HMGCR(12-14) expression in cells in the presence of a HMGCR inhibitor relative to HMGCR(12-14) expression in the absence of a HMGCR inhibitor (e.g., a portable apparatus suitable for execution of an algorithm for providing an assessment of likelihood of responsiveness of the patient to a statin therapy, as described herein). Also included in the subject kits may be buffers, dNTPs, and controls, (e.g., positive and negative control nucleic acids) for performing the subject methods. Primers in the subject kits may be detectably labeled or unlabeled.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Methods and Materials

The following methods and materials were used in the examples below.

Patients and cell lines. The Cholesterol/Atherosclerosis Pharmacogenetics (CAP) trial was a non-randomized, non-blinded study of 944 African-American and Caucasian men and women age 30 or older with baseline total cholesterol of 160 to 400 mg/dL. Baseline health, demographic and physical examination data were obtained, and plasma lipids and lipoproteins (LDL, HDL, triglyceride and lipoprotein subfractions), and apoproteins (AI and B) were measured upon enrollment, as well as after 4 weeks and 6 weeks on 40 mg/day simvastatin. FIG. 3C provides the effects of simvastatin therapy upon total cholesterol, LDL cholesterol and HDL cholesterol in this patient population.

Immortalized lymphocyte cell lines were created as a source of DNA for each patient as part of the NIH study Blood was collected in either yellow top tubes (ACD solution A) or green top tubes (heparin) for separation and transformation by EBV. ACD (acid-citrate-dextrose) tubes contained a preservative, so blood collected in these tubes can sit for up to 48 hours without compromising the efficiency of separation or transformation. Blood collected in green top tubes was separated as soon as possible, since it did not contain any preservative and the cells would begin to die within 24 hours.

White blood cells (WBCs) were separated by mixing blood with a compound that aggregates the red blood cells (RBCs), thereby increasing their sedimentation rate. The WBCs were only slightly affected and were collected from the upper part of the cells when they have settled. Alternatively the procedure of Boyum (Boyum, A (1964) Nature, 204, 793; Boyum, A (1968) Scand. J. Clin. Lab. Invest., 21, supplement 97.) was used. This procedure is a one-step centrifugal technique for isolating lymphocytes from whole blood by centrifuging against a medium whose density is higher than that of lymphocytes, but lower than those of RBCs and granulocytes. Several solutions for the isolation of lymphocytes are commercially available, e.g., IsoPrep™ (Robbins Scientific Corporation).

The blood was well mixed then transferred to a 50 ml polystyrene (clear) tube. The volume was adjusted to 30 ml with PBS and underlayer with 15 ml of IsoPrep™, which must be at room temperature. Alternatively, add 15 ml of IsoPrep™ was added to another 50 ml tube and the diluted blood overlaid on the IsoPrep™ The samples were then centrifuges (brake off!) at room temperature at 450 g for 30 minutes or 800 g for 20 minutes.

After centrifugation the mononuclear cells (lymphocytes and monocytes) formed a distinct layer at the plasma/IsoPrep™ interface. The RBCs and polys were below the IsoPrep™. The lymphocyte layer was removed and transferred to a polypropylene (cloudy) centrifuge tube using a Pasteur pipet (with or without aspirating off the plasma layer). After washing with 35-40 ml PBS, the samples were gently mixed very well, and centrifuged at room temperature at 300 g for 10 minutes.

The supernatant was aspirated, and the pellet resuspended in 10 ml PBS, and the cells counted either manually, using a hemocytometer and 6% acetic acid (HAc) to lyse the RBCs, or automatically, using an electronic cell counter. About $10-15 \times 10^6$ cells were used for transformation Extra lymphocytes for freezing were transferred to a 5 ml centrifuge tube until ready to freeze. The cells were then washed at room temperature at 200 g for 10 minutes and the supernatant aspirated. The pellet was resuspended in 3 ml RPMI 20% FBS with cyclosporin A (4 µg/ml) and transferred to a T25 tissue culture flask. 1 ml of EBV stock was added and the flask placed in a 37° C., 5% $CO_2$ incubator.

A subset of 66 African American patients from the CAP trial was chosen for testing of the HMGCR gene expression assay (Examples 1, 2, 3, 4 and 5). An African American was defined as an individual who had three or more grandparents who self-identified as African American. A Caucasian was defined as an individual who had three or more grandparents who self-identified as Caucasian American. The table below provides a summary of the demographics for this population.

Study Population A—African American

| African Americans - 1.8 uM simvastatin | | |
|---|---|---|
| | Baseline | Absolute Difference |
| N | 66 | |
| Sex | 62.1% female | |
| Smoking (>1 pack per day) | 27.30% | |
| Age | 58.16 ± 1.47 | |
| BMI | 28.96 ± 0.67 | |
| Total Cholesterol | 207.38 ± 3.43 | −54.48 ± 2.79 |
| IDL-Cholesterol | 21.08 ± 1.00 | −9.06 ± 0.75 |
| LDL-Cholesterol | 128.39 ± 3.45 | −51.17 ± 2.37 |
| HDL-Cholesterol | 59.85 ± 2.48 | 0.96 ± 0.75 |
| ApoA1 | 135.14 ± 3.73 | −1.69 ± 1.76 |
| ApoB | 89.50 ± 2.15 | −27.11 ± 1.71 |

To determine that the association was not race specific, 43 Caucasian American patients were chosen for additional testing of the HMGCR gene expression assay (Examples 1, 2, 3 and 5). The table below provides a summary of the population demographics.

Study Population B

| Caucasian Americans - 1.8 uM simvastatin | | |
|---|---|---|
| | Baseline | Absolute Difference |
| N | 43 | |
| Sex | 46.5% female | |
| Smoking (>1 pack per day) | 9.30% | |
| Age | 52.73 ± 1.82 | |
| BMI | 27.52 ± 0.76 | |
| Total Cholesterol | 217.102 ± 5.223 | −65.614 ± 3.791 * |
| IDL-Cholesterol | 22.141 ± 1.054 | −10.373 ± 1.066 |
| LDL-Cholesterol | 137.716 ± 4.649 | −63.909 ± 3.455 * |
| HDL-Cholesterol | 55.952 ± 2.320 | 2.155 ± 0.904 |
| ApoA1 | 133.159 ± 3.663 | −2.114 ± 2.271 |
| ApoB | 97.159 ± 3.656 | −33.091 ± 2.700 * |

* Means significantly different between African American (Study Populations A and C) and Caucasian American subpopulations (p < 0.05)

A dose study was performed with a second subset of 60 African American patients (Examples 1, 3, 4, and 5). Cell lines derived from these patients were treated with a higher dose, 14.5 µM simvastatin, than the previous two groups, 1.8 µM simvastatin. The population demographics for this group is shown below.

Study Population C

| African Americans - 14.5 uM simvastatin dose | | |
|---|---|---|
| | Baseline | Absolute Difference |
| N | 60 | |
| Sex | 53.3% female | |
| Smoking (>1 pack per day) | 25.00% | |
| Age | 55.40 ± 1.83 | |
| BMI | 30.37 ± 0.88 | |
| Total Cholesterol | 213.17 ± 4.96 | −57.73 ± 3.62 |
| IDL-Cholesterol | 22.83 ± 1.05 | −10.23 ± 0.80 |
| LDL-Cholesterol | 138.25 ± 4.88 | −55.74 ± 3.36 |
| HDL-Cholesterol | 56.31 ± 1.92 | 1.98 ± 0.55 |
| ApoA1 | 129.73 ± 3.77 | 2.80 ± 1.79 |
| ApoB | 94.62 ± 2.32 | −28.03 ± 1.88 |

Cell lines were grown at 37° C., 5% $CO_2$ in RPMI Medium 1640 (Invitrogen) supplemented with 10% fetal bovine serum (Hyclone), 500 units/ml Penicillin/Streptomycin (Invitrogen) and 2 nM GlutaMAX (Invitrogen). $3.75 \times 10^6$ cells from each line was exposed to either 1.8 µM or 14.5 µM activated simvastatin, or a control solution for 24 hours. Media was changed 24 hours prior to exposure to ensure the cultures were in an active growth phase. After exposure, cells were pelleted, resuspended in Trizol (Invitrogen), and stored at −80° C. until RNA extraction. Each cell line was exposed to simvastatin twice with replicate experiments performed on different days.

RNA isolation and cDNA synthesis. RNA was isolated from the cell/Trizol slurries following the manufacturer's protocol (Invitrogen). RNA quality was assessed by gel electrophoresis and A260/A280 measured via spectrophotometry. 2.5 mg of RNA from each of the two replicate experiments was pooled for a total of 5 mg of RNA from each cell line. cDNA was synthesized using random primers with the High Capacity cDNA Archive Kit (Applied Biosystems) following the manufacturer's protocol.

Real time PCR. HMGCR gene expression was quantitated via real time PCR using three TaqMan assays spanning exons 6 to 7 (HMGCR ex6-7), 12 to 13 (HMGCR ex12-13) and 12 to 14 (HMGCR ex12-14). HMGCR ex6-7 and HMGCR ex12-13 were purchased as pre-made gene expression assays from Applied Biosystems (part numbers Hs00168352_ml and Hs01102991_g1).

Reagents for detection of HMGCR ex12-14 were custom designed and included two primers (HMGCR ex12-14.F:

CTC CAG TAC CTA CCT TAC AGG GAT T (SEQ ID NO:1), and HGMCR ex12-14.R: GCT GCT GGC ACC TCC A (SEQ ID NO:2) and one probe (CAA GCA AGG AGT AAT TAT (SEQ ID NO:3), where the probe was labeled with FAM on the 5' end and a non-fluorescent quencher on the 3' end. Each real time PCR reaction included 1× TaqMan Universal PCR Master Mix (Applied Biosystems), 1× TaqMan assay and 10 ng cDNA. Each reaction was performed in triplicate and run on an ABI PRISM 7900 Sequence Detection System using default cycling conditions and parameters.

Real time PCR standards were generated by amplifying 100 ng lymphocyte cDNA with 1×PCR buffer, 1.5 mM $MgCl_2$, 0.5 mM dNTPs, 1 mM of each primer, and 0.125 units Taq DNA polymerase (Invitrogen). The ex6-7 standard was created with primers HMGCR ex5.F: GTT TGC CCT CAG TTC CAA CTC ACA (SEQ ID NO:4) and HMGCR ex8.R: TTG ACC CTC TGA ATT ACA GGA TTC GG (SEQ ID NO:5). The ex12-13 standard was generated with primers HMGC ex12.F: TGC TAA GCA TAT CCC AGC CTA CAA G (SEQ ID NO:32) and HMGCR ex13.R: ATT GCT CTG CAG CCT CTA TTG GTG (SEQ ID NO:6), and the 12-14 standard with primers HMGCR ex12.F and HMGCR ex14.R: ATG CCT CCT TTA TCA CTG CGA ACC (SEQ ID NO:7). All primers were purchased from Integrated DNA Technologies. PCR cycling conditions were as follows: 94° C. 2 minutes, 92° C. 30 seconds, 60° C. 30 seconds, 72° C. 30 seconds (92°, 60° and 72° cycles were repeated 35 times), and 72° C. 5 minutes. Eight PCR reactions for each standard was generated, pooled, and quantitated via gel electrophoresis using a DNA low mass ladder (Invitrogen). PCR standards were then serially diluted to create standards containing approximately $10^9$ molecules/50 to $10^2$ molecules/50. PCR standards were run in triplicate on each plate to serve as a positive control for the assay and to quantitate levels of gene expression.

Control genes were also assayed to normalize results from the three HMGCR assays. A validation experiment was performed with ten unrelated genes, EFNB3, LGALS14, SLC7A5, BIN2, CLPTM1, PDE7A, SORL1, SERPINB8, HRLP5 and KLF2, to identify the genes for which expression is least affected by simvastatin. SYBR Green assays were designed for each of the 10 potential control genes with primer sequences as follows:

```
EFNB3 ex3.F:
                                    (SEQ ID NO: 8)
TTC CGC TCG CAC CAC GAT TAC TA
and EFNB3 ex4.R:
                                    (SEQ ID NO: 9)
AGA AGC ACC TTC ATG CCT CTG GTT;

LGALS14 ex2.F:
                                    (SEQ ID NO: 10)
GCC TGT TGG TTC GTG CGT GAT AAT
and LGALS14 ex3.R:
                                    (SEQ ID NO: 11)
TGA CCA AAG TGC AGT CGG AAT TGG;

SLC7A5 ex1.F:
                                    (SEQ ID NO: 12)
AGT ACA TCG TGG CCC TGG TCT T
and SLC7A5 ex2.R:
                                    (SEQ ID NO: 13)
GCC TTC ACG CTG TAG CAG TTC A;

BIN2 ex12.F
                                    (SEQ ID NO: 14)
ACA ACA ACC TCA CAG CAC CTG AAC
and BIN2 ex13.R
                                    (SEQ ID NO: 15)
TTG AAC AGC TTC TCT GGC GAG GTT;

CLPTM1 ex3.R:
                                    (SEQ ID NO: 16)
TCG GCG GAA CCA ACT GCT GAT
and CLPTM1 ex4.R:
                                    (SEQ ID NO: 17)
TCG GCG GAA CCA ACT GCT GAT;

PDE7A ex8.F:
                                    (SEQ ID NO: 18)
GGA TCA TCC AGG TGT TAA TCA ACC TTT CC
and PDE7A ex9.R:
                                    (SEQ ID NO: 19)
CTG TGT CTC CAT TTG TTG CCT GCT T;

SORL1 ex6.F:
                                    (SEQ ID NO: 20)
GCT TCG GGA CAA GTA CAT GTT TGC
and SORL1 ex7.R:
                                    (SEQ ID NO: 21)
TTG TGA CAA ACT GGG CTG CTC TCA;

SERPINB8 ex6.F:
                                    (SEQ ID NO: 22)
CCT GAC AAA GCT GGT CCT TGT GAA
and SERPINB8 ex7.R:
                                    (SEQ ID NO: 23)
CAG GAC CTG GGT GTG TAC CTC ATC;

HRLP5 ex3.F:
                                    (SEQ ID NO: 24)
CCA AAG CCT GAG AAT GAA GGC AAG T
and HRLP5 ex4.R:
                                    (SEQ ID NO: 25)
TCT CCA GGT CTG GGT CTT GGT TT;
and KLF2 ex2.F:
                                    (SEQ ID NO: 26)
AGA CCT ACA CCA AGA CTT CGC ATC TG
and KLF2 ex3.R:
                                    (SEQ ID NO: 27)
TCT GAG CGC GCA AAC TTC CA.
```

The ten potential control genes were quantitated with SYBR Green real time PCRs using three different test lymphocyte cell lines exposed to both statin and the control buffer. Real time PCR reactions consisted of 1×SYBR Green PCR master mix (Applied Biosystems), 150 nM primers and 100 ng cDNA, and were performed using default cycling conditions on the ABI PRISM 7000 Sequence Detection System. Analysis using the Excel applet GeNorm (Vandesompele et al, 2000), and demonstrated SLC7A5 and CLPTM1 were the most stable control genes and only two were necessary to calculate an accurate normalization factor for further data normalization.

SLC7A5 and CLPTM1 were quantitated in all samples by TaqMan assays purchased from Applied Biosystems (part numbers Hs0018526_m1 and Hs00171300_m1). Real time PCR standards for these two assays were prepared using primers SLC7A ex1a.F: ATC TCC AAA TCG GGC GGA GAC TA (SEQ ID NO:28) and SLC7A ex3.R: CCA CAT CCA GTT TGG TGC CTT CAA (SEQ ID NO:29), and CLPTM1 ex4.F: TCT TCA TCA TCT GGG CCA TCA GCA (SEQ ID NO:30) and CLPTM1 ex6.R: TCA TTT CTG GGT CCG CTT CTG TCT (SEQ ID NO:31) following the same protocol as described above for the HMGCR real time PCR standards. Normalization factors for each cDNA were calculated using GeNorm, and applied to the three HMGCR gene expression results to generate normalized data.

Figure 3A:
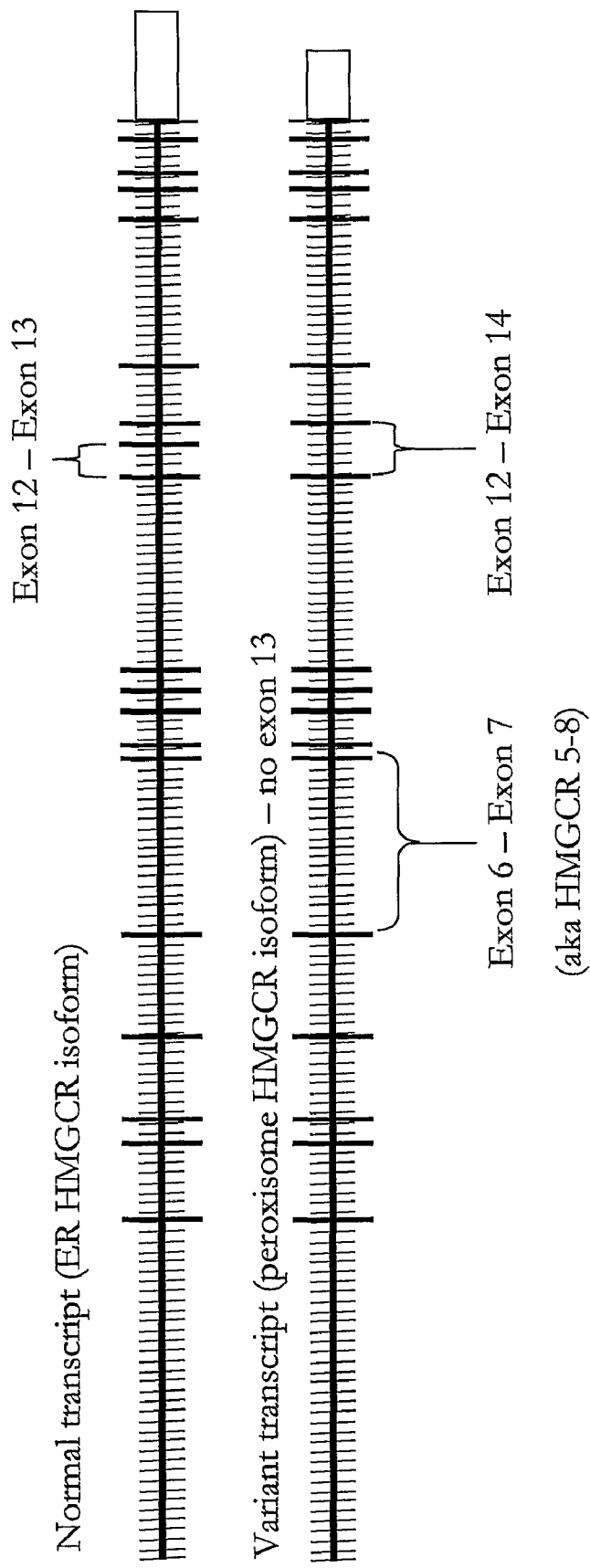
FIG. 3A is a schematic showing the relative position of probes in a real-time PCR (RT-PCR) assay to distinguish HMGCR(12-13) transcripts from HMGCR(12-14) statin-resistant transcripts.

FIG. 1 provides a schematic showing the unspliced and HMGCR(12-14) transcripts, and the expected sizes of the unspliced HMGCR and HMGCR(12-14) (spliced) transcripts. FIG. 2 further illustrates the differences in the unspliced and HMGCR(12-14) transcripts, the encoded proteins, and intracellular locations. FIG. 3A is a schematic illustrating the relative locations of the probes used in the real time PCR. The 6-7 exon probes were used as controls in some assays. FIG. 3B is a schematic of the assay showing an exemplary HMGCR(12-14) probe for detection of HMGCR transcripts having the 12-14 splice junction.

Statistical analysis. The three assay replicates were averaged and normalized with the calculated normalization factor specific for each cDNA. Gene expression "fold changes" were calculated by dividing the quantity of mRNA measured in the statin treated sample with the quantity of mRNA measured in the control buffer exposed sample. JMP was used to create a multivariate regression model with the absolute change of total cholesterol, LDL-cholesterol and HDL-cholesterol measured in vivo as dependent variables and HMGCR(12-14) fold change in expression as independent variables.) The "intercept" refers to the Y-intercept, and is the mathematical value describing where the line intersects with the X-axis at 0. The smoking and age parameters are regression coefficients that determine the slope of the line along with the fold change.

Some data are presented herein according to the following ratio:

$$\frac{\Delta HMGCR(12\text{-}14)}{\Delta t HMGCR}$$

where

ΔHMGCR(12-14) is a change of the expression level of HMGCR(12-14) in the presence of the HMGCR inhibitor relative to the baseline expression level in the absence of the HMGCR inhibitor, and ΔtHMGCR is to a change of expression level of total HMGCR in the presence of the HMGCR inhibitor relative to a baseline total HMGCR expression level in the absence of the HMGCR inhibitor.

Example 1

HMGCR Gene Expression is Upregulated by Statin Treatment

Cells obtained from patients in Study Populations A. B and C were used in this example. There were no significant differences in population demographics or statin response between the two African American sub-populations used in this study (Study Population A and Study Population C), however smoking status, age, BMI, and absolute change in total and LDL-cholesterol differed between the African American (Study Population A and Study Population C) and Caucasian American (Study Population B) sub-populations.

HMGCR(12-13) and HMGCR(12-14) mRNA expression was assessed in lymphocyte cells ($7.5 \times 10^6$) from individual subjects in CAP prior to and after 24 hours of exposure to either 1.8 µM or 14.5 µM activated simvastatin or control (blank solution). HMGCR(12-13) and spliced HMGCR(12-14) mRNA was quantified via real time PCR as described above. Two control genes, SLC7A5 and CLPTM1, which are unaffected by statin treatment were quantified with real time PCR to normalize results of the HMGCR assays.

Cell lines were derived from Caucasian (Study Population B) and African American (Study Population B) patients. Gene expression differed between races as total HMGCR (6-7) gene up-regulation was slightly higher in cell lines derived from Caucasian Americans versus African Americans (average 1.60-fold change vs. 1.44-fold change, p=0.017). There was no difference between races in the magnitude of up-regulation of HMGCR(12-13) or HMGCR(12-14). Other patient characteristics such as age, sex, and smoking status were not related to the in vitro regulation of either the total or alternatively spliced HMGCR transcripts.

Example 2

Association Between HMGCR Gene Expression (In Vitro) and Lipid Response (In Vivo)

To determine if statin-induced transcriptional regulation of HMGCR could be related to the variation in statin efficacy, the association between 1) the magnitude of statin-induced HMGCR gene expression measured in vitro in the immortalized lymphocyte cell lines, and 2) the magnitude of lipid and apoprotein response to simvastatin treatment measured in vivo in the CAP trial patients from which the cell lines were derived was investigated. As a change in induction of HMGCR(12-14) may reflect a difference in overall HMGCR gene expression, and/or splicing specifically, the ratio of the two fold-changes, HMGCR(12-14)/HMGCR(6-7) to represent the process of splicing independent of the effects on overall HMGCR gene transcription. Similarly, expression of HMGCR(12-13) is also expressed as a ratio with HMGCR (6-7).

As shown in the table below, the HMGCR(12-14)/HMGCR(6-7) ratio was significantly associated with the absolute difference of total-cholesterol, LDL-cholesterol, and ApoB in both races. The relationship between the change in IDL cholesterol and ApoA1 with H12-14/H6-7 was also marked in the African Americans. Greater induction of the alternatively spliced transcript, HMGCR(12-14), was seen in individuals with smaller reductions of all parameters. In contrast, neither the HMGCR(12-13)/HMGCR(6-7) ratio, nor the HMGCR(6-7) fold-change was not associated with the change in total cholesterol, IDL cholesterol, LDL cholesterol, ApoB or ApoA1. These data show that increased HMGCR (12-14) transcript levels is associated with a decreased response to a HMGCR inhibitor, as indicated by smaller reductions of total, IDL, and LDL cholesterol, as well as ApoB levels.

Association between HMGCR alternative splicing and lipid
response to statin. Split by Race, 1.8 uM statin treated

|  | African American* | | Caucasian American** | |
| --- | --- | --- | --- | --- |
|  | H12-14/H6-7 | H12-13/H6-7 | H12-14/H6-7 | H12-13/H6-7 |
| Total-cholesterol | 0.0134 | 0.1093 | 0.0464 | 0.9587 |
| IDL | 0.0766 | 0.191 | 0.6882 | 0.8559 |
| LDL-cholesterol | 0.0146 | 0.2117 | 0.0373 | 0.8129 |
| ApoA1 | 0.0728 | 0.518 | 0.8695 | 0.1041 |
| ApoB | 0.0356 | 0.8996 | 0.0296 | 0.4663 |

Data adjusted for age, BMI and smoking status
*Study Population A;
**Study Population B African American and Caucasian American combined*

|  | H12-14/H6-7 | H12-13/H6-7 |
| --- | --- | --- |
| Total-cholesterol | 0.0013 | 0.2064 |
| IDL | 0.3202 | 0.3305 |
| LDL-cholesterol | 0.0015 | 0.2221 |
| ApoA1 | 0.1745 | 0.1639 |
| ApoB | 0.0024 | 0.5816 |

*Study Populations A and B

Example 3

HMGCR Inhibitors Induce Changes in HMGCR Transcripts that Are Both Race and Dose Sensitive The change in HDL-cholesterol is associated with the magnitude of induction of the HMGCR(12-14) and HMGCR(12-13) transcripts, but was not associated with either H12-14/H6-7 or H12-13/H6-7 ratios. The "magnitude of induction" is calculated as the quantity of HMGCR gene expression from statin treated cells (normalized by SLC7A and CLPTM1) divided by the quantity of HMGCR gene expression from the control cells (normalized by SLC7A and CLPTM1). Consequently, a change in the "magnitude of induction" or "fold-change" of either H12-14 or H12-13 may reflect a difference in overall HMGCR gene expression, or a difference in the amount of alternative splicing at exon 13. In contrast, the H12-14/H6-7 ratio is calculated as the magnitude of induction of the H12-14 transcript divided by the magnitude of induction of the H6-7 transcript. Division by H6-7 acts both as a second round of normalization as well as separates the effects on total gene transcription from alternative splicing.

Association between HMGCR gene expression
and change in HDL-cholesterol

|  | H12-14 p/m | H12-13 p/m | H6-7 p/m |
| --- | --- | --- | --- |
| African American* - 1.8 uM | 0.0308 | 0.0033 | 0.2777 |
| African American*** - 14.5 uM | 0.0267 | 0.0505 | 0.0676 |
| Caucasian American** - 1.8 uM | 0.0188 | 0.1419 | 0.0332 |

*Study Population A;
**Study Population B;
***Study Population C

Figure 4A:
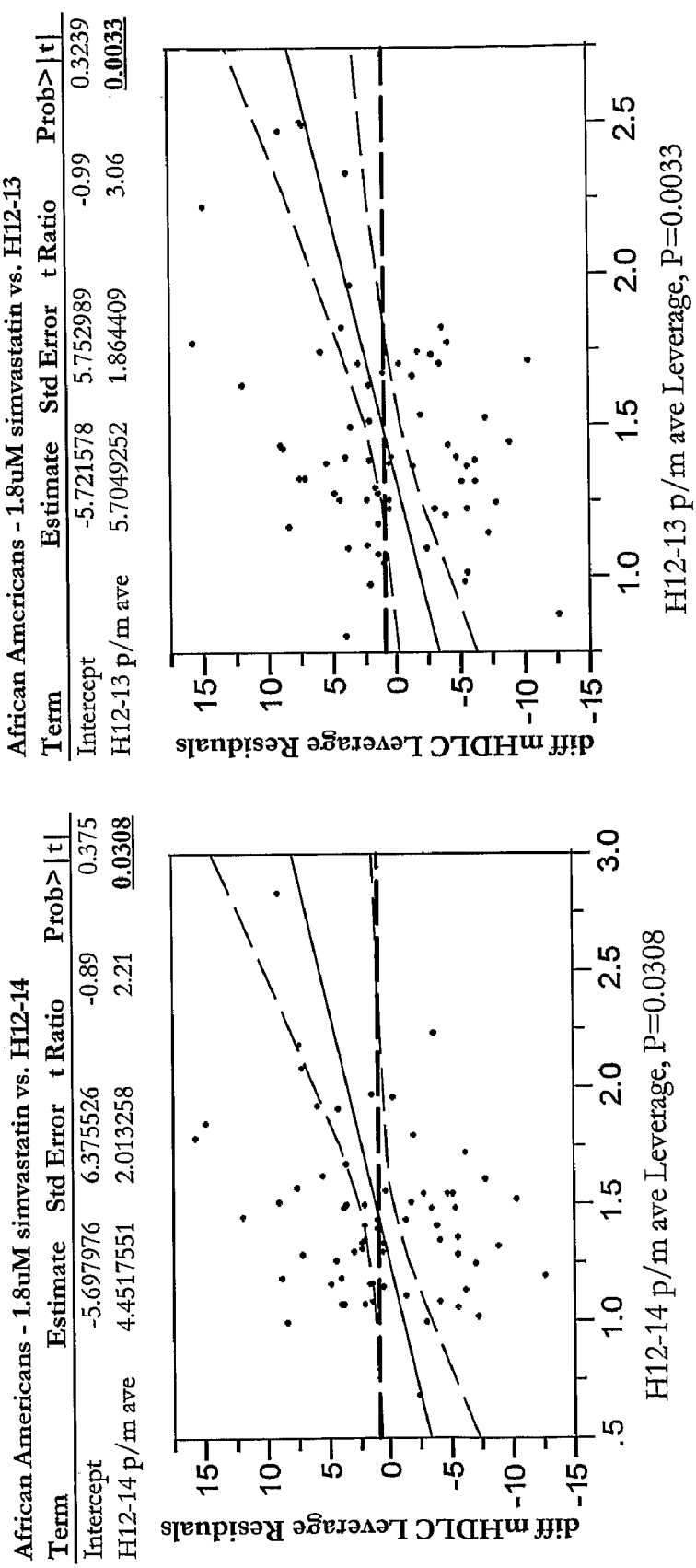
Figure 5:
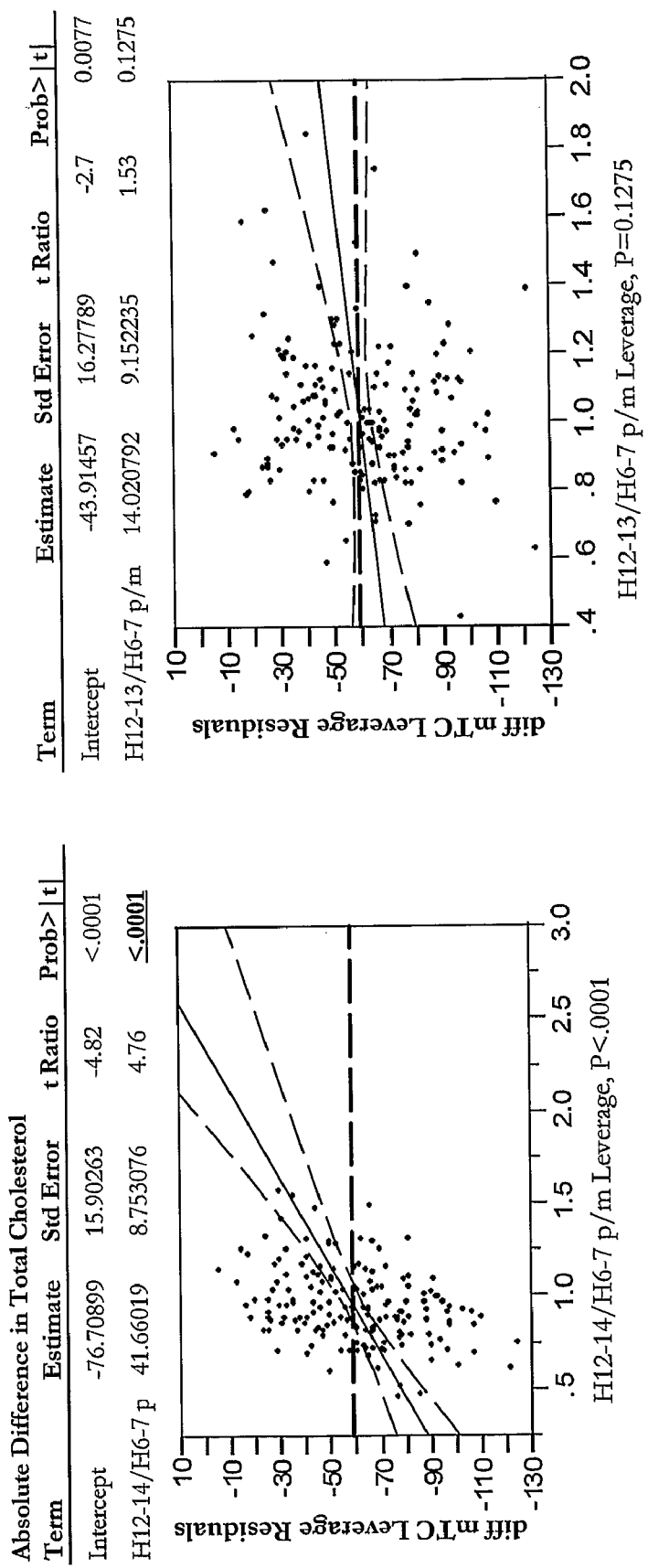
FIG. 5 are a collection of tables and graphs showing the association of change in total cholesterol (as measured in vivo) with the ratio of fold-changes of the alternatively spliced HMGCR transcript lacking exon 13 (HMGCR12-14) to the total HMGCR transcripts, and the ratio of fold-changes of the full-length HMGCR transcript (HMGCR12-13) to total HMGCR transcripts. "fold change", indicates the magnitude of statin-induced gene expression relative to baseline control.
Figure 6:
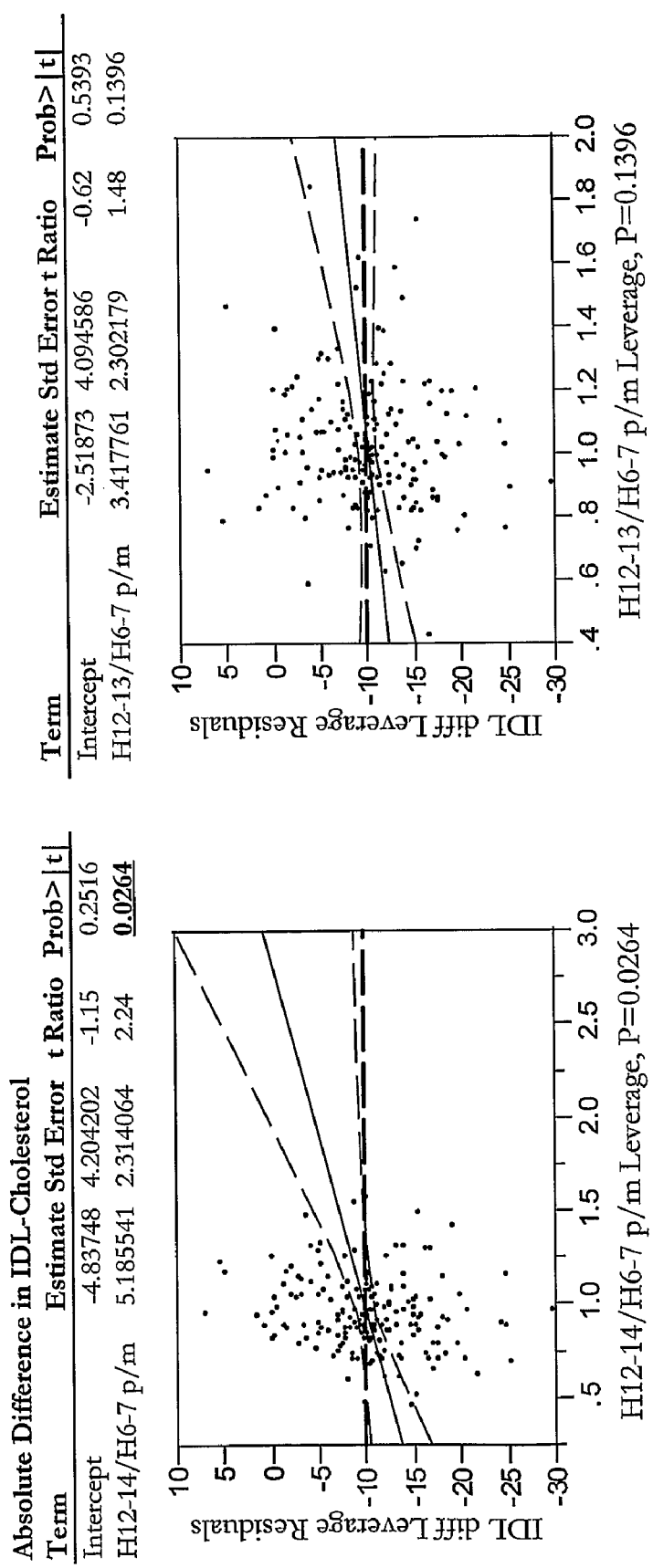
FIG. 6 are a collection of tables and graphs showing the association of change in IDL cholesterol (as measured in vivo) with the ratio of fold-changes of the alternatively spliced HMGCR transcript lacking exon 13 (HMGCR12-14) to the total HMGCR transcripts, and the ratio of fold-changes of the full-length HMGCR transcript (HMGCR12-13) to total HMGCR transcripts. "fold change", indicates the magnitude of statin-induced gene expression relative to control.
Figure 7:
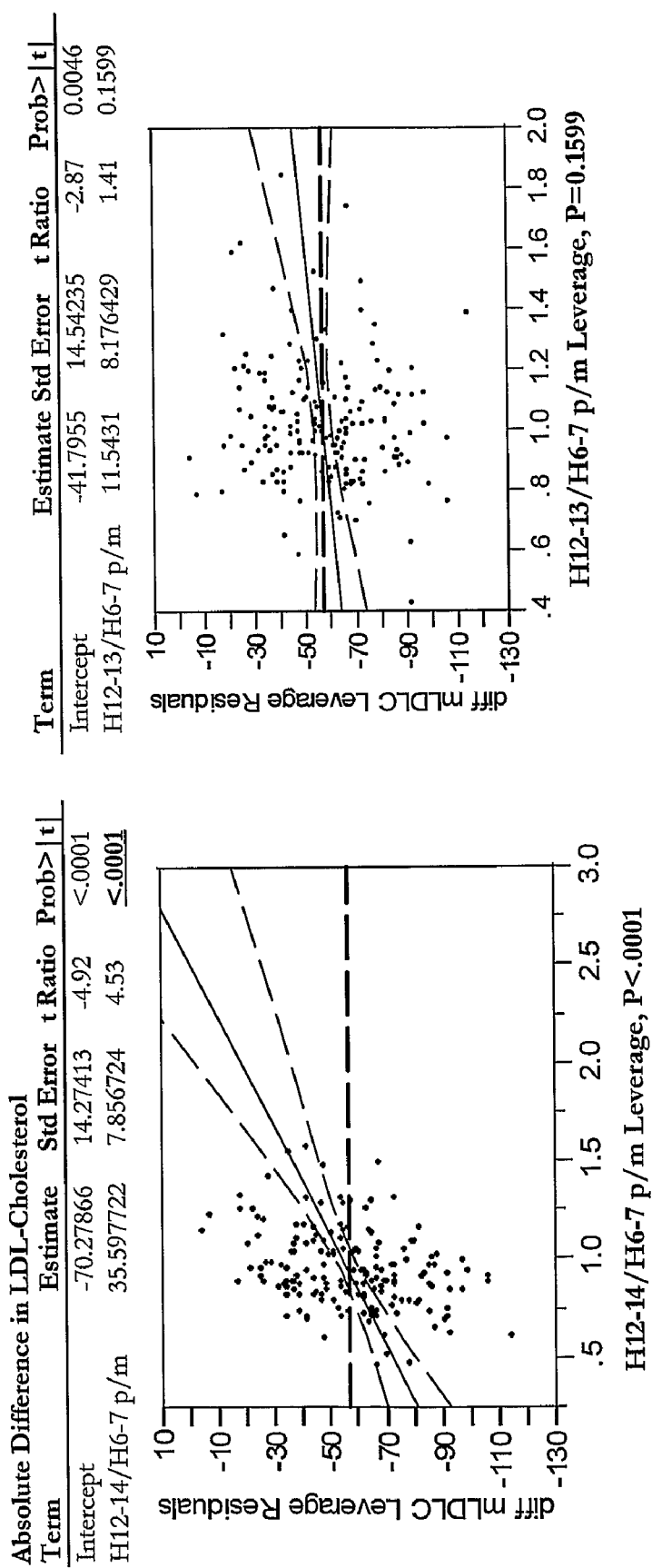
FIG. 7 are a collection of tables and graphs showing the association of change in LDL cholesterol (as measured in vivo) with the ratio of fold-changes of the alternatively spliced HMGCR transcript lacking exon 13 (HMGCR12-14) to the total HMGCR transcripts, and the ratio of fold-changes of the full-length HMGCR transcript (HMGCR12-13) to total HMGCR transcripts. "fold change", indicates the magnitude of statin-induced gene expression relative to control.
Figure 8:
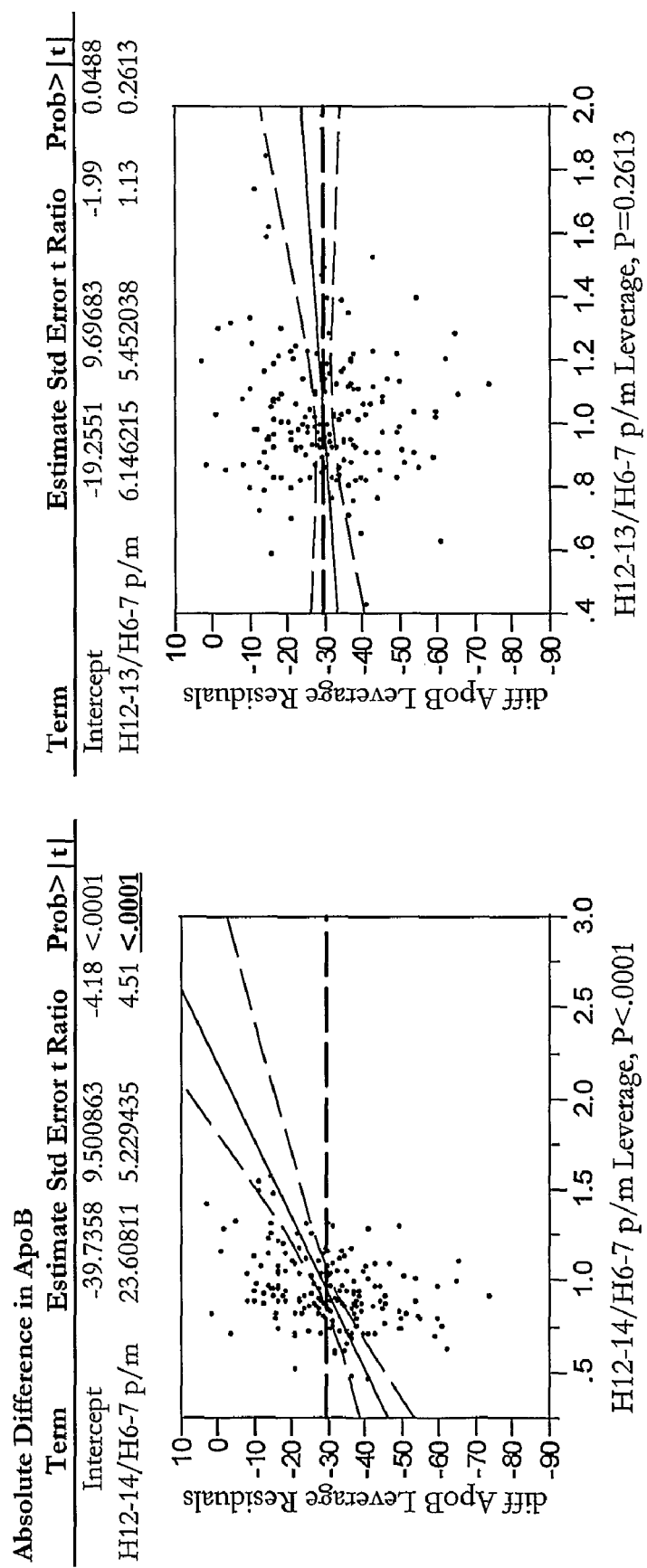
FIG. 8 are a collection of tables and graphs showing the association of change in apoB, the main protein component of LDL, with the ratio of fold-changes of the alternatively spliced HMGCR transcript lacking exon 13 (HMGCR12-14) to the total HMGCR transcripts, and the ratio of fold-changes of the full-length HMGCR transcript (HMGCR12-13) to total HMGCR transcripts. "fold change", indicates the magnitude of statin-induced gene expression relative to control.

Interestingly, the relationship between statin-induced HMGCR gene expression and change in HDL-cholesterol was different between the two races. As shown in FIGS. 4A and 4B, in African Americans greater H12-14 or greater H12-13 was associated with greater increases in HDL-cholesterol. In contrast, greater H12-14 was associated with smaller increases (or decreases) of HDL-cholesterol in the Caucasian Americans. There was no significant association between change in HDL-cholesterol and total HMGCR transcript induction in the African Americans, however total HMGCR transcription was associated with change in HDL-cholesterol in Caucasian Americans, where total HMGCR transcript induction is measured by detection of H6-7 (the splice junction at exons 6 and 7 of HMGCR), which is common to both the H12-14 and H1-12-13 transcripts. These data show that, in African Americans increased H12-14 and/or increased H12-13 indicates a positive response to HMGCR inhibitor therapy in terms of increased HDL levels. However, in Caucasians, increased H12-14 is an indicative of an unfavorable response in HDL-cholesterol Example 4

Increasing Statin Dose Increases HMGCR Induction, But not Splicing

To determine if the relationship between HMGCR alternative splicing and statin efficacy, a dose experiment was performed in which an additional 60 cell lines were incubated with 14.5 μM simvastatin for 24 hours. Cell lines obtained from (Study Populations A and C were used for this experiment.

The higher dose of statin resulted in greater up-regulation of HMGCR(6-7) compared to the original 1.8 μM dose (1.65±0.48-fold vs. 1.44-fold, p=0.003). HMGCR(12-13) and HMGCR(12-14) were also up-regulated to a greater extent, however the differences were not statistically significant. The HMGCR(12-13)/HMGCR(6-7) and HMGCR(12-14)/HMGCR(6-7) ratios were not affected by statin concentration.

Example 5

HMGCR Alternative Splicing is Associated with Statin Efficacy

As statin dose does not appear to influence alternative splicing, all three experimental populations were combined. Combining the data revealed that associations between the magnitude of splicing and lipid responses reached greater statistical significance (n=169). As shown in the table below and FIGS. 5-8, greater HMGCR(12-14)/HMGCR(6-7) was associated with smaller reductions in the absolute difference of total cholesterol, IDL-cholesterol, LDL-cholesterol, and ApoB. Relationships remained significant even after adjustment for known statin determinants such as age, BMI, smoking status, and race. In addition, the magnitude of HMGCR (12-14) fold change was significantly associated with the change in total cholesterol, LDL-cholesterol and ApoB (data not shown). There was no relationship between HMGCR(12-13)/HMGCR(6-7) and the change in total cholesterol, IDL-cholesterol, LDL-cholesterol, and ApoB.

| Total Population (All African American and Caucasian American)* | | |
|---|---|---|
| | H12-14/H6-7 | H12-13/H6-7 |
| Total-cholesterol | <0.0001 | 0.1275 |
| IDL | 0.0264 | 0.1396 |
| LDL-cholesterol | <0.0001 | 0.1599 |
| HDL-cholesterol | 0.4953 | 0.4511 |
| ApoA1 | 0.0088 | 0.0299 |
| ApoB | <0.0001 | 0.2613 |

*Study Populations A, B and C

Figure 9:
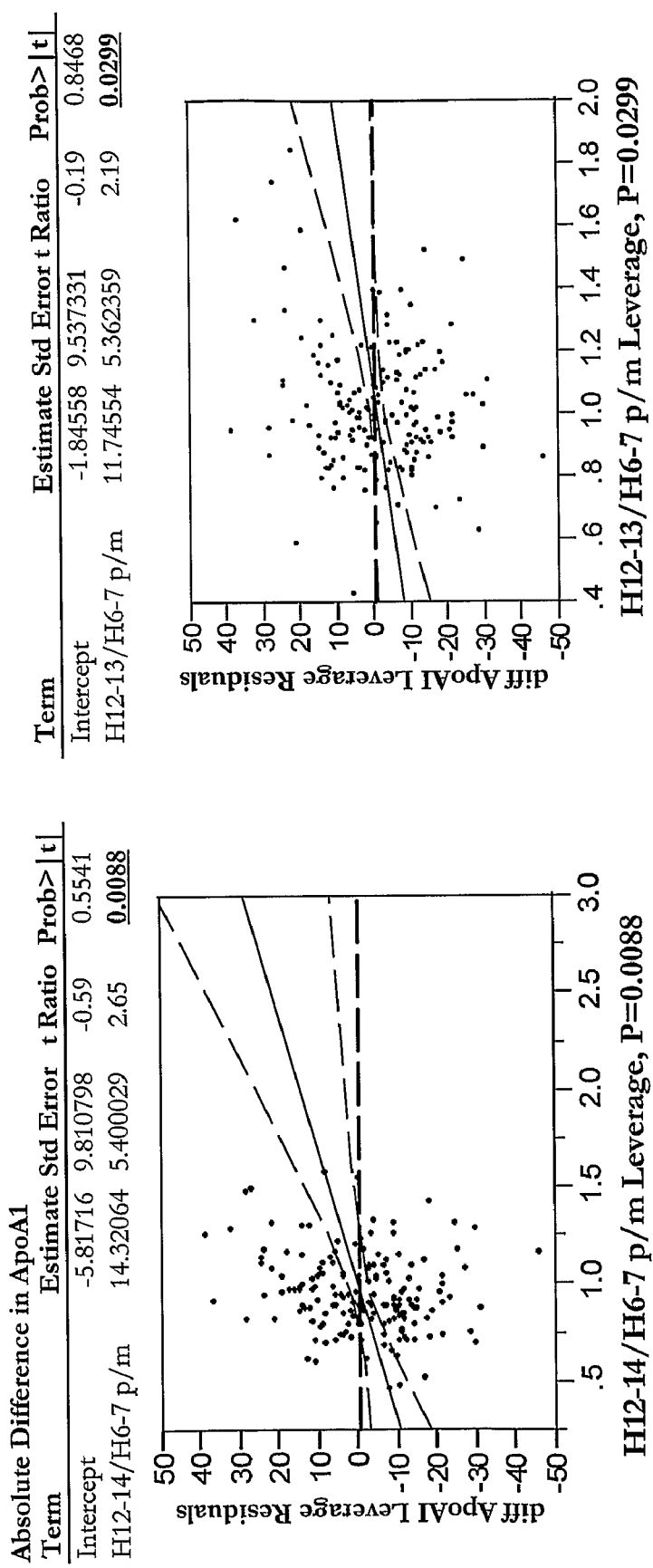
FIG. 9 are a collection of tables and graphs showing the association of change in apoA1, a protein which is associated with HDL, with the ratio of fold-changes of the alternatively spliced HMGCR transcript lacking exon 13 (HMGCR12-14) to the total HMGCR transcripts, and the ratio of fold-changes of the full-length HMGCR transcript (HMGCR12-13) to total HMGCR transcripts. "fold change", indicates the magnitude of statin-induced gene expression relative to control.

In contrast, both HMGCR(12-14)/HMGCR(6-7) and HMGCR(12-13)/HMGCR(6-7) were associated with the change in ApoA1 (FIG. 9). However, the relationship with HMGCR(12-14)/HMGCR(6-7) ratio reached much greater statistical significance than the HMGCR(12-13)/HMGCR(6-7) ratio. In addition, the change in ApoA1 was also associated with the magnitude of fold change of both HMGCR(12-14) and HMGCR(12-13). Similarly, the HMGCR(12-14) relationship also reached greater statistical significance than the HMGCR(12-13) relationship (data not shown).

Since the HDL-cholesterol relationship with HMGCR(12-14) and HMGCR(12-13) differed between races, the combined data was not applied to this lipid response. In addition to the race effect described previously, there was also a dose effect on the relationship between HMGCR(12-14) and HMGCR(12-13) with the change in HDL-cholesterol (FIGS. 10A and 10B). In the African American cell lines (Study Population A) treated with the lower dose of simvastatin, greater HMGCR(12-14) and HMGCR(12-13) were associated with larger increases in HDL-cholesterol. However, at the higher statin dose, greater HMGCR(12-14) and HMGCR(12-13) was associated with smaller increases or reduction of HDL-cholesterol.

Example 6

Prediction of Estimated Change in Total Cholesterol Upon Administration of Statin to a Patient Based on the data in Examples 1-5, an algorithm was designed to facilitate prediction of the change in total cholesterol:

Change in total cholesterol (mg/dl)=−76.7+(41.7)(12-14/6-7 ratio)

where "12-14/6-7 ratio" is a numerical value indicating the change in HMGCR(12-14) expression following exposure of a patient's cells to statin (where baseline is HMGCR(12-14) expression prior to drug exposure) divided by the change in HMGCR(6-7) expression following exposure of a patient's cells to statin (where baseline in HMGCR(6-7)).

Using the algorithm immediately above, the magnitude in response in total cholesterol following statin administration can be predicted. For example, a patient with a measured 12-14/6-7 ratio of 1.5 would be expected to have a reduction of total cholesterol of −14.2 mg/dl on statin therapy. As the mean total cholesterol reduction is −58.5 mg/dl, then this individual would experience a 75.7% decrease in the ability of statin treatment to lower total cholesterol.

The algorithm used to predict absolute change in total cholesterol can be executed so as to provide guidance to the clinician or other health practitioner as to the relevance of different observed ratios in HMGCR(12-14)/HMGCR(6-7) expression in response to statin:

| Total Cholesterol - predicted absolute change (mg/dl) with statin treatment | | | |
|---|---|---|---|
| | 95% confidence interval | | |
| 12-14/6-7 ratio | low | average | High |
| 0.5 | −100 | −90 | −75 |
| 1.0 | −62 | −60 | −58 |
| 1.5 | −50 | −40 | −30 |

Example 7

Prediction of Estimated Change in IDL Cholesterol Upon Administration of Statin to a Patient Based on the data in Examples 1-5, an algorithm was designed to facilitate prediction of the change in total cholesterol:

Change in IDL cholesterol (mg/dl)=−4.84+(5.18)(12-14/6-7 ratio)

where "12-14/6-7 ratio" is a numerical value indicating the change in HMGCR(12-14) expression following exposure of a patient's cells to statin (where baseline is HMGCR(12-14) expression prior to drug exposure) divided by the change in HMGCR(6-7) expression following exposure of a patient's cells to statin (where baseline in HMGCR(6-7)).

Using the algorithm immediately above, the magnitude in response in IDL cholesterol following statin administration can be predicted. For example, a patient with a measured 12-14/6-7 ratio of 1.5 would be expected to have a reduction of IDL cholesterol of 2.93 mg/dl on statin therapy. As the mean total cholesterol reduction is −9.85 mg/dl, then this individual would experience a 129.8% decrease in the ability of statin treatment to lower IDL cholesterol.

The algorithm used to predict absolute change in IDL cholesterol can be executed so as to provide guidance to the clinician or other health practitioner as to the relevance of different observed ratios in HMGCR(12-14)/HMGCR(6-7) expression in response to statin:

| IDL Cholesterol - predicted absolute change (mg/dl) with statin treatment | | | |
|---|---|---|---|
| | 95% confidence interval | | |
| 12-14/6-7 ratio | low | average | High |
| 0.5 | −15 | −14 | −10 |
| 1.0 | −11 | −10 | −9 |
| 1.5 | −10 | −7.5 | −6 |

Example 8

Prediction of Estimated Change in LDL Cholesterol Upon Administration of Statin to a Patient Based on the data in Examples 1-5, an algorithm was designed to facilitate prediction of the change in LDL cholesterol:

Change in LDL-cholesterol in mg/dl=−70.3+(35.6)(12-14/6-7 ratio)

where "12-14/6-7 ratio" is a numerical value indicating the change in HMGCR(12-14) expression following exposure of a patient's cells to statin (where baseline is HMGCR(12-14) expression prior to drug exposure) divided by the change in HMGCR(6-7) expression following exposure of a patient's cells to statin (where baseline in HMGCR(6-7)). Using the algorithm immediately above, the magnitude in response in LDL cholesterol following statin administration can be predicted. For example, a patient with a measured 12-14/6-7 ratio of 1.5 would be expected to have a reduction of LDL-cholesterol of −16.9 mg/dl on statin therapy. As the mean LDL-cholesterol reduction is −56.0 mg/dl, then this individual would experience a 75.2% decrease in the ability of statin treatment to lower LDL-cholesterol. In terms of overall cardiovascular disease (CVD) risk, lowering LDL-cholesterol by 1 mg/dl translates into a 1% decrease in CVD risk. Thus, this reduction in LDL-cholesterol would translate to a 16.9% decrease in CVD risk compared to the 56% decrease in risk seen in the average individual.

The algorithm above used to predict absolute change in LDL cholesterol can be executed so as to provide guidance to the clinician or other health as to the relevance of different observed fold changes in HMGCR(12-14)/HMGCR(6-7) expression in response to statin:

| LDL-Cholesterol - predicted absolute change (mg/dl) with statin treatment | | | |
|---|---|---|---|
| 12-14/6-7 | 95% confidence interval | | |
| | low | Average | high |
| 0.5 | −90 | −80 | −70 |
| 1.0 | −65 | −58 | −55 |
| 1.5 | −50 | −45 | −35 |

Example 9

Prediction of Estimated Change in HDL Cholesterol Upon Administration of Statin to a Patient Through Assessment of 12-14 HMGCR Expression in African Americans Based on the data in Example 1, an algorithm using the change in HMGCR(12-14) in African Americans was designed to facilitate prediction of the change in HDL cholesterol. The prediction algorithm was based on the data generated from the 1.8 µM simvastatin dose which is much closer to normal physiological levels than the 14.5 µM dose. The algorithm based on measured HMGCR(12-14) expression levels is as follows:

Change in HDL-cholesterol in mg/dl=−5.70+(4.45) (12-14 fold change)

where "12-14 fold change" is a numerical value indicating the change in HMGCR(12-14) expression following exposure of a patient's cells to statin (where baseline is HMGCR(12-14) expression prior to drug exposure).

Using the algorithm immediately above, the magnitude in response in HDL cholesterol following statin administration can be predicted. For example, a patient with a measured 12-14 fold change of 2.0 would be expected to have an increase of HDL-cholesterol of 3.2 mg/dl on statin therapy. As the mean HDL-cholesterol increase is 0.96 mg/dl, then this individual would experience a 233.3% increase in the ability of statin treatment to raise HDL-cholesterol over normal expectations. In terms of overall cardiovascular disease (CVD) risk, raising HDL-cholesterol by 0.5 mg/dl translates into a 2-3% decrease in CVD risk. Thus, this individual would have a 6-9% lower risk of CVD on statin treatment as compared to the 2-3% decrease in the average person taking statin.

The algorithm above used to predict absolute change in HDL cholesterol can be executed so as to provide guidance to the clinician or other health practitioner as to the relevance of different observed fold changes in HMGCR(112-14) expression in response to statin (compared to a baseline HMGCR (12-14) expression in the absence of the drug):

| HDL-Cholesterol - predicted absolute change (mg/dl) with statin treatment in African Americans | | | |
|---|---|---|---|
| 12-14 fold | 95% confidence interval | | |
| change | low | average | high |
| 1.0 | −4 | −1 | +0.5 |
| 1.5 | −1 | 0 | +1.0 |
| 2.0 | 0 | +2.0 | +5.0 |

Example 10

Prediction of Estimated Change in HDL Cholesterol Upon Administration of Statin to a Patient Through Assessment of 12-14 HMGCR Expression—in Caucasian Americans Based on the data in Examples 1-5, an algorithm using change in HMGCR(12-14) was designed to facilitate prediction of the change in HDL cholesterol in Caucasian Americans. The algorithm based on measured HMGCR(12-14) expression levels is as follows:

Change in HDL-cholesterol in mg/dl=12.85+(−6.22) (12-14 fold change)

where "12-14 fold change" is a numerical value indicating the change in HMGCR(12-14) expression following exposure of a patient's cells to statin (where baseline is HMGCR(12-14) expression prior to drug exposure).

Using the algorithm immediately above, the magnitude in response in HDL cholesterol following statin administration can be predicted. For example, a patient with a measured 12-14 fold change of 2.0 would be expected to have an increase of HDL-cholesterol of 0.41 mg/dl on statin therapy. As the mean HDL-cholesterol increase is 2.17 mg/dl, then this individual would experience a 81.1% decrease in the ability of statin treatment to raise HDL-cholesterol over normal expectations. In terms of overall cardiovascular disease (CVD) risk, raising HDL-cholesterol by 0.5 mg/dl translates into a 2-3% decrease in CVD risk. Thus, this individual would have only a 2-3% reduction of CVD risk on statin treatment as compared to the 4-6% seen in the average person taking statin.

The algorithm above used to predict absolute change in HDL cholesterol can be executed so as to provide guidance to the clinician or other health practitioner as to the relevance of different observed fold changes in HMGCR(12-14) expression in response to statin (compared to a baseline HMGCR (12-14) expression in the absence of the drug):

| HDL-Cholesterol - predicted absolute change (mg/dl) with statin treatment in Caucasian Americans | | | |
|---|---|---|---|
| 12-14 fold | 95% confidence interval | | |
| change | low | average | high |
| 1.0 | +1 | +3 | +6.0 |
| 1.5 | 0 | +2 | +4.0 |
| 2.0 | −5 | −1 | +2.0 |

Example 11

Prediction of Estimated Change in HDL Cholesterol Upon Administration of Statin to a Patient Through Assessment of 12-13 HMGCR Expression—in African Americans Based on the data in Examples 1-5, an algorithm using either change in HMGCR(12-14) was designed to facilitate prediction of the change in HDL cholesterol. The algorithm based on measured HMGCR(12-13) expression levels is as follows:

Change in HDL-cholesterol in mg/dl=−5.72+(5.7)(12-13 fold change)

where "12-13 fold change" is a numerical value indicating the change in HMGCR(12-13) expression following exposure of a patient's cells to statin (where baseline is HMGCR(12-13) expression prior to drug exposure).

Using the algorithm immediately above, the magnitude in response in HDL cholesterol following statin administration can be predicted. For example, a patient with a measured 12-13 fold change of 2.0 would be expected to have an increase of HDL-cholesterol of 5.68 mg/dl on statin therapy. As the mean HDL-cholesterol increase is 0.96 mg/dl, then this individual would experience a 591.7% increase in the ability of statin treatment to raise HDL-cholesterol over normal expectations. In terms of overall cardiovascular disease (CVD) risk, raising HDL-cholesterol by 0.5 mg/dl translates into a 2-3% decrease in CVD risk. Thus, this individual would have a 20-30% decrease in CVD risk on statin treatment as compared to the 4-6% decrease seen in the average person taking statin.

The algorithm above used to predict absolute change in HDL cholesterol can be executed so as to provide guidance to the clinician or other health practitioner as to the relevance of different observed fold changes in HMGCR(12-13) expression in response to statin (compared to a baseline HMGCR (12-13) expression in the absence of the drug):

| HDL-Cholesterol - predicted absolute change (mg/dl) with statin treatment in African Americans | | | |
|---|---|---|---|
| 12-13 fold | 95% confidence interval | | |
| change | low | average | high |
| 1.0 | −5 | −3 | 0 |
| 1.5 | −1 | 0 | +1.0 |
| 2.0 | 0 | +2.0 | +5.0 |

Example 12

Prediction of Estimated Change in HDL Cholesterol Upon Administration of Statin to a Patient Through Assessment of 12-13 HMGCR Expression—in Caucasian Americans Based on the data in Examples 1-5, algorithms using either change in HMGCR(12-14) or change in HMGCR(12-13) were designed to facilitate prediction of the change in HDL cholesterol. The algorithm based on measured HMGCR(12-13) expression levels is as follows:

Change in HDL-cholesterol in mg/dl=6.92+(−2.0)(12-13 fold change)

where "12-13 fold change" is a numerical value indicating the change in HMGCR(12-13) expression following exposure of a patient's cells to statin (where baseline is HMGCR(12-13) expression prior to drug exposure).

Using the algorithm immediately above, the magnitude in response in HDL cholesterol following statin administration can be predicted. For example, a patient with a measured 12-13 fold change of 2.0 would be expected to have an increase of HDL-cholesterol of 2.92 mg/dl on statin therapy. As the mean HDL-cholesterol increase is 2.17 mg/dl, then this individual would experience a 34.5% increase in the ability of statin treatment to raise HDL-cholesterol over normal expectations. In terms of overall cardiovascular disease (CVD) risk, raising HDL-cholesterol by 0.5 mg/dl translates into a 2-3% decrease in CVD risk. Thus, this individual would have a 6-9% decrease in risk of CVD on statin treatment as compared to the 4-6% seen in the average person taking statin.

The algorithm above used to predict absolute change in HDL cholesterol can be executed so as to provide guidance to the clinician or other health practitioner as to the relevance of different observed fold changes in HMGCR(12-13) expression in response to statin (compared to a baseline HMGCR (12-13) expression in the absence of the drug):

| HDL-Cholesterol - predicted absolute change (mg/dl) with statin treatment in Caucasian Americans | | | |
|---|---|---|---|
| 12-13 fold | 95% confidence interval | | |
| change | low | average | high |
| 1.0 | 0 | +3 | +6.0 |
| 1.5 | 0 | +2 | +5.0 |
| 2.0 | −1 | −1 | +4.0 |

Example 13

Prediction of Estimated Change in Total Cholesterol Upon Administration of Statin to a Patient Based on the data in Examples 1-5, an algorithm was designed to facilitate prediction of the change in total cholesterol:

Change in total cholesterol (mg/dl)=−46.1+(10.8)(HMGCR(12-14) fold change)

where "HMGCR(12-14) fold change" is a numerical value indicating the change in HMGCR(12-14) expression following exposure of a patient's cells to statin (where baseline is HMGCR(12-14) expression prior to drug exposure).

Using the algorithm immediately above, the magnitude in response in total cholesterol following statin administration can be predicted. For example, a patient with a measured HMGCR(12-14) fold change of 2.0 would be expected to have a reduction of total cholesterol of −24.5 mg/dl on statin therapy. As the mean total cholesterol reduction is −58.5 mg/dl, then this individual would experience a 57.8% decrease in the ability of statin treatment to lower total cholesterol over the average individual.

The algorithm used to predict absolute change in total cholesterol can be executed so as to provide guidance to the clinician or other health practitioner as to the relevance of different observed fold changes in HMGCR(12-14) expression in response to statin:

| Total Cholesterol - predicted absolute change (mg/dl) with statin treatment | | | |
|---|---|---|---|
| 12-14 fold change | 95% confidence interval | | |
| | low | average | High |
| 0.5 | −82 | −70 | −60 |
| 1.5 | −65 | −60 | −55 |
| 2.0 | −59 | −50 | −40 |

Example 14

Prediction of Estimated Change in LDL Cholesterol Upon Administration of Statin to a Patient Based on the data in Examples 1-5, an algorithm was designed to facilitate prediction of the change in LDL cholesterol:

Change in LDL-cholesterol in mg/dl=−44.0+(9.2)(HMGCR(12-14) fold change)

where "HMGCR(12-14) fold change" is a numerical value indicating the change in HMGCR(12-14) expression following exposure of a patient's cells to statin (where baseline is HMGCR(12-14) expression prior to drug exposure).

Using the algorithm immediately above, the magnitude in response in LDL cholesterol following statin administration can be predicted. For example, a patient with a measured HMGCR(12-14) fold change of 2.0 would be expected to have a reduction of LDL-cholesterol of −25.6 mg/dl on statin therapy. As the mean LDL-cholesterol reduction is −56.0 mg/dl, then this individual would experience a 54.3% decrease in the ability of statin treatment to lower LDL-cholesterol. In terms of overall cardiovascular disease (CVD) risk, lowering LDL-cholesterol by 1 mg/dl translates into a 1% decrease in CVD risk. Thus, this reduction in LDL-cholesterol would translate to a 25.6% decrease in CVD risk compared to the 56% decrease in risk seen in the average individual.

The algorithm above used to predict absolute change in LDL cholesterol can be executed so as to provide guidance to the clinician or other health as to the relevance of different observed fold change in HMGCR(12-14) expression in response to statin:

| LDL-Cholesterol - predicted absolute change (mg/dl) with statin treatment | | | |
|---|---|---|---|
| 12-14 fold change | 95% confidence interval | | |
| | low | Average | high |
| 0.5 | −78 | −68 | −58 |
| 1.5 | −60 | −58 | −55 |
| 2.0 | −55 | −45 | −35 |

What is claimed is:

1. A method for determining responsiveness of a subject to a 3-hydroxy-3-methylglutaryl coenzyme A reductase (HMGCR) inhibitor therapy, the method comprising:
   contacting a cell of a subject with an HMGCR inhibitor;
   assessing expression of a HMGCR(12-14) isoform in the cell of the subject;
   wherein the expression level of the HMGCR(12-14) in the presence of the HMGCR inhibitor compared to a baseline expression level of the HMGCR(12-14) isoform in the absence of the HMGCR inhibitor is indicative of the subject's responsiveness to the HMGCR inhibitor.

2. The method of claim 1, wherein expression of the HMGCR(12-14) isoform in the cell in the presence of the HMGCR inhibitor which is increased relative to a baseline expression level in the absence of the HMGCR inhibitor indicates the subject will have an overall reduced therapeutic response to the HMGCR inhibitor.

3. The method of claim 1, wherein when HMGCR(12-14) expression levels are to be used to determine response of the subject to the HMGCR inhibitor as assessed by a change in one of total cholesterol, LDL, IDL, ApoA1 or ApoB, the expression level of the HMGCR(12-14) in the presence of the HMGCR inhibitor is measured as $$\frac{\Delta HMGCR(12\text{-}14)}{\Delta tHMGCR}$$

where
   $\Delta HMGCR(12\text{-}14)$ is a change of the expression level of HMGCR(12-14) in the presence of the HMGCR inhibitor relative to the baseline expression level in the absence of the HMGCR inhibitor, and
   $\Delta HMGCR$ is a change of the expression level of total HMGCR in the presence of the HMGCR inhibitor relative to a baseline total HMGCR expression level in the absence of the HMGCR inhibitor.

4. The method of claim 1, wherein an increase in HMGCR (12-14) isoform expression in the presence of the HMGCR inhibitor compared to the baseline expression level is inversely correlated with an expected reduction in total cholesterol in the subject following administration of the HMGCR inhibitor.

5. The method of claim 1, wherein an increase in HMGCR (12-14) isoform expression in the presence of the HMGCR inhibitor compared to the baseline expression level is inversely correlated with an expected reduction in low density lipoprotein (LDL) cholesterol in the subject following administration of the HMGCR inhibitor.

6. The method of claim 1, wherein an increase in HMGCR (12-14) isoform expression in the presence of the HMGCR inhibitor compared to the baseline expression level is inversely correlated with an expected reduction in intermediate density lipoprotein (IDL) cholesterol in the subject following administration of the HMGCR inhibitor.

7. The method of claim 1, wherein an increase in HMGCR (12-14) isoform expression in the presence of the HMGCR inhibitor compared to the baseline expression level is inversely correlated with an expected reduction in apoB in the subject following administration of the HMGCR inhibitor.

8. The method of claim 1, wherein an increase in HMGCR (12-14) isoform expression in the presence of the HMGCR inhibitor over the baseline expression level is directly correlated with an expected increase in apoAI in the subject following administration of the HMGCR inhibitor.

9. A method of treating a subject having or suspected of having a lipid disorder, said method comprising the step of
    contacting a cell from the subject with an 3-hydroxy-3-methylglutaryl coenzyme A reductase (HMGCR) inhibitor;
    assessing expression of a HMGCR(12-14) isoform in the cell of the subject, wherein the expression level of HMGCR(12-14) in the presence of the HMGCR inhibitor compared to a baseline expression level of HMGCR (12-14) in the absence of the HMGCR inhibitor is indicative of the subject's responsiveness to the HMGCR inhibitor; and
    selecting a therapy for the lipid disorder for the subject in accordance with the subject's responsiveness as determined by said assessing so as to provide for at least one of a reduction in total cholesterol, reduction in LDL cholesterol, reduction in IDL cholesterol, reduction in apoB, an increase in HDL cholesterol, or an increase in apoAI;
    wherein administration of the selected therapy provides for treatment of the lipid disorder in the subject.

10. The method of claim 9, wherein a level of expression of the HMGCR(12-14) isoform in the cell in the presence of the HMGCR inhibitor which is increased relative to a baseline expression level in the absence of the HMGCR inhibitor indicates the subject will have overall decreased therapeutic responsiveness to the HMGCR inhibitor.

11. The method of claim 9, wherein
    an increase in HMGCR(12-14) isoform expression in the presence of the HMGCR inhibitor over the baseline expression level is inversely correlated with an expected reduction in total cholesterol in the subject following administration of the HMGCR inhibitor;
    an increase in HMGCR(12-14) isoform expression in the presence of the HMGCR inhibitor compared to the baseline expression level is inversely correlated with an expected reduction in low density lipoprotein (LDL) cholesterol in the subject following administration of the HMGCR inhibitor;
    an increase in HMGCR(12-14) isoform expression in the presence of the HMGCR inhibitor compared to the baseline expression level is inversely correlated with an expected reduction in apoB in the subject following administration of the HMGCR inhibitor; and
    an increase in HMGCR(12-14) isoform expression in the presence of the HMGCR inhibitor compared to the baseline expression level is directly correlated with a change in apoAI.

12. The method of claim 9, wherein HMGCR(12-14) expression is assessed by detection of mRNA encoding an HMGCR(12-14) isoform.

13. A method of classifying a subject according to sensitivity or resistance to a 3-hydroxy-3-methylglutaryl coenzyme A reductase (HMGCR) inhibitor therapy, the method comprising the steps of
    determining an expression level of a HMGCR(12-14) isoform in a cell of a subject, wherein the expression level of the HMGCR(12-14) isoform in the presence of the HMGCR inhibitor compared to an expression level of the HMGCR(12-14) isoform in the absence of the HMGCR inhibitor is indicative of the subject's responsiveness to the HMGCR inhibitor; and
    assigning the subject to a classification according to HMGCR inhibitor responsiveness.

14. A method for determining a subject's suitability for participation in a clinical trial for a cholesterol modulating therapy, said method comprising the step of
    determining an expression level of a 3-hydroxy-3-methylglutaryl coenzyme A reductase (HMGCR) isoform in the cell of the subject, wherein the HMGCR isoform is a HMGCR(12-14) isoform, wherein the expression level of the HMGCR(12-14) in the presence of the HMGCR inhibitor compared to an expression level of the HMGCR(12-14) isoform in the absence of the HMGCR inhibitor is indicative of the subject's responsiveness to the HMGCR inhibitor; and
    wherein the expression level of the HMGCR(12-14) isoform is indicative of the subject's suitability for participation in the clinical trial.

15. A method for screening a candidate agent, the method comprising:
    contacting a mammalian cell with a candidate agent;
    determining an expression level of a HMGCR(12-14) isoform in the cell;
    wherein a candidate agent that facilitates inhibition of HMGCR activity without a significant increase in HMGCR(12-14) isoform expression is identified.

16. The method of claim 15, wherein said contacting is in the presence of a HMGCR inhibitor.

17. The method of claim 16, wherein a candidate agent that provides for decreased HMGCR(12-14) isoform expression in the presence of the HMGCR inhibitor is a candidate for combination therapy with the HMGCR inhibitor.

18. The method of claim 15, wherein a candidate agent that, in the absence of an HMGCR inhibitor, provides for increased HMGCR(12-14) expression is identified.

19. A method for screening a candidate agent, the method comprising:
    contacting a mammalian cell with a candidate agent; and
    determining an expression level of a HMGCR(12-14) isoform in the cell;
    wherein a candidate agent that facilitates an increase in HMGCR(12-14) isoform is identified as an agent that can facilitate an increase in apoAI in a subject.

20. The method of claim 19, wherein said contacting is in the presence of a HMGCR inhibitor.

21. A method for screening a candidate agent, the method comprising:

contacting a mammalian cell with a candidate agent; and determining an expression level of a HMGCR(12-14) isoform, a HMGCR(12-13) isoform or total HMGCR;

wherein a candidate agent that facilitates a change in an expression level of at least one of HMGCR(12-14) isoform, HMGCR(12-13) isoform or total HMGCR is identified as an agent that can facilitate change in HDL cholesterol.

22. The method of claim 21, wherein said contacting is in the presence of a HMGCR inhibitor.

23. A method of modulating high density lipoprotein (HDL) cholesterol levels in a subject, said method comprising the steps of:

contacting a cell from a subject with an 3-hydroxy-3-methylglutaryl coenzyme A reductase (HMGCR) inhibitor;

assessing expression of a HMGCR expression marker in the cell of the subject, where the marker is HMGCR(12-13) isoform, HMGCR(12-14) isoform or total HMGCR;

administering a therapy to modulate HDL cholesterol levels in the subject, wherein the therapy is selected based on the results of said assessing;

wherein said administering provides of modulation of HDL cholesterol levels in the subject.

* * * * *

SEQUENCE LISTING

<160> NUMBER OF SEQ ID NOS: 33

<210> SEQ ID NO 1
<211> LENGTH: 25
<212> TYPE: DNA
<213> ORGANISM: Artificial Sequence
<220> FEATURE:
<223> OTHER INFORMATION: Synthetic primer

<400> SEQUENCE: 1
ctccagtacc taccttacag ggatt                                    25

<210> SEQ ID NO 2
<211> LENGTH: 16
<212> TYPE: DNA
<213> ORGANISM: Artificial Sequence
<220> FEATURE:
<223> OTHER INFORMATION: Synthetic primer

<400> SEQUENCE: 2
gctgctggca cctcca                                              16

<210> SEQ ID NO 3
<211> LENGTH: 18
<212> TYPE: DNA
<213> ORGANISM: Artificial Sequence
<220> FEATURE:

```
<223> OTHER INFORMATION: Synthetic primer
<220> FEATURE:
<221> NAME/KEY: misc_difference
<222> LOCATION: 1
<223> OTHER INFORMATION: 5'-FAM labeled
<220> FEATURE:
<221> NAME/KEY: misc_difference
<222> LOCATION: 18
<223> OTHER INFORMATION: 3'-non-fluorescent quencher labeled

<400> SEQUENCE: 3
caagcaagga gtaattat                                                   18

<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4
gtttgccctc agttccaact caca                                            24

<210> SEQ ID NO 5
<211> LENGTH: 25
<212> TYPE: DNA
<213> ORGANISM: Artificial Sequence
<220> FEATURE:
<223> OTHER INFORMATION: Synthetic primer

<400> SEQUENCE: 5
tgctaagcat atcccagcct acaag                                           25

<210> SEQ ID NO 6
<211> LENGTH: 24
<212> TYPE: DNA
<213> ORGANISM: Artificial Sequence
<220> FEATURE:
<223> OTHER INFORMATION: Synthetic primer

<400> SEQUENCE: 6
attgctctgc agcctctatt ggtg                                            24

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
atgcctcctt tatcactgcg aacc                                            24

<210> SEQ ID NO 8
<211> LENGTH: 23
<212> TYPE: DNA
<213> ORGANISM: Artificial Sequence
<220> FEATURE:
<223> OTHER INFORMATION: Synthetic primer

<400> SEQUENCE: 8
ttccgctcgc accacgatta cta                                             23

<210> SEQ ID NO 9
<211> LENGTH: 24
<212> TYPE: DNA
<213> ORGANISM: Artificial Sequence
<220> FEATURE:
```

<223> OTHER INFORMATION: Synthetic primer

<400> SEQUENCE: 9
agaagcacct tcatgcctct ggtt					24

<210> SEQ ID NO 10
<211> LENGTH: 24
<212> TYPE: DNA
<213> ORGANISM: Artificial Sequence
<220> FEATURE:
<223> OTHER INFORMATION: Synthetic primer

<400> SEQUENCE: 10
gcctgttggt tcgtgcgtga taat					24

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
tgaccaaagt gcagtcggaa ttgg					24

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
agtacatcgt ggccctggtc tt					22

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
gccttcacgc tgtagcagtt ca					22

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
acaacaacct cacagcacct gaac					24

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
ttgaacagct tctctggcga ggtt					24

<210> SEQ ID NO 16

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
tcggcggaac caactgctga t                                            21

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
tcggcggaac caactgctga t                                            21

<210> SEQ ID NO 18
<211> LENGTH: 29
<212> TYPE: DNA
<213> ORGANISM: Artificial Sequence
<220> FEATURE:
<223> OTHER INFORMATION: Synthetic primer

<400> SEQUENCE: 18
ggatcatcca ggtgttaatc aacctttcc                                    29

<210> SEQ ID NO 19
<211> LENGTH: 25
<212> TYPE: DNA
<213> ORGANISM: Artificial Sequence
<220> FEATURE:
<223> OTHER INFORMATION: Synthetic primer

<400> SEQUENCE: 19
ctgtgtctcc atttgttgcc tgctt                                        25

<210> SEQ ID NO 20
<211> LENGTH: 24
<212> TYPE: DNA
<213> ORGANISM: Artificial Sequence
<220> FEATURE:
<223> OTHER INFORMATION: Synthetic primer

<400> SEQUENCE: 20
gcttcgggac aagtacatgt ttgc                                         24

<210> SEQ ID NO 21
<211> LENGTH: 24
<212> TYPE: DNA
<213> ORGANISM: Artificial Sequence
<220> FEATURE:
<223> OTHER INFORMATION: Synthetic primer

<400> SEQUENCE: 21
ttgtgacaaa ctgggctgct ctca                                         24

<210> SEQ ID NO 22
<211> LENGTH: 24
<212> TYPE: DNA
<213> ORGANISM: Artificial Sequence
<220> FEATURE:
<223> OTHER INFORMATION: Synthetic primer

<400> SEQUENCE: 22
```

```
cctgacaaag ctggtccttg tgaa                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic primer

<400> SEQUENCE: 23
caggacctgg gtgtgtacct catc                                              24

<210> SEQ ID NO 24
<211> LENGTH: 25
<212> TYPE: DNA
<213> ORGANISM: Artificial Sequence
<220> FEATURE:
<223> OTHER INFORMATION: Synthetic primer

<400> SEQUENCE: 24
ccaaagcctg agaatgaagg caagt                                             25

<210> SEQ ID NO 25
<211> LENGTH: 23
<212> TYPE: DNA
<213> ORGANISM: Artificial Sequence
<220> FEATURE:
<223> OTHER INFORMATION: Synthetic primer

<400> SEQUENCE: 25
tctccaggtc tgggtcttgg ttt                                               23

<210> SEQ ID NO 26
<211> LENGTH: 26
<212> TYPE: DNA
<213> ORGANISM: Artificial Sequence
<220> FEATURE:
<223> OTHER INFORMATION: Synthetic primer

<400> SEQUENCE: 26
agacctacac caagacttcg catctg                                            26

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
tctgagcgcg caaacttcca                                                   20

<210> SEQ ID NO 28
<211> LENGTH: 23
<212> TYPE: DNA
<213> ORGANISM: Artificial Sequence
<220> FEATURE:
<223> OTHER INFORMATION: Synthetic primer

<400> SEQUENCE: 28
atctccaaat cgggcggaga cta                                               23

<210> SEQ ID NO 29
<211> LENGTH: 24
<212> TYPE: DNA
<213> ORGANISM: Artificial Sequence
<220> FEATURE:
```

```
<223> OTHER INFORMATION: Synthetic primer

<400> SEQUENCE: 29
ccacatccag tttggtgcct tcaa                                      24

<210> SEQ ID NO 30
<211> LENGTH: 24
<212> TYPE: DNA
<213> ORGANISM: Artificial Sequence
<220> FEATURE:
<223> OTHER INFORMATION: Synthetic primer

<400> SEQUENCE: 30
tcttcatcat ctgggccatc agca                                      24

<210> SEQ ID NO 31
<211> LENGTH: 24
<212> TYPE: DNA
<213> ORGANISM: Artificial Sequence
<220> FEATURE:
<223> OTHER INFORMATION: Synthetic primer

<400> SEQUENCE: 31
tcatttctgg gtccgcttct gtct                                      24

<210> SEQ ID NO 32
<211> LENGTH: 26
<212> TYPE: DNA
<213> ORGANISM: Artificial Sequence
<220> FEATURE:
<223> OTHER INFORMATION: Synthetic primer

<400> SEQUENCE: 32
ttgaccctct gaattacagg attcgg                                    26

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ttataattac tccttgcttg                                           20
```